(12) United States Patent
Nakao et al.

(10) Patent No.: US 7,365,164 B2
(45) Date of Patent: Apr. 29, 2008

(54) SCREENING METHOD FOR GENES OF BREWING YEAST

(75) Inventors: Yoshihiro Nakao, Kyoto (JP); Norihisa Nakamura, Kyoto (JP); Yukiko Kodama, Takatsuki (JP); Tomoko Fujimura, Takatsuki (JP); Toshihiko Ashikari, Takatsuki (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 11/499,703

(22) Filed: Aug. 7, 2006

(65) Prior Publication Data

US 2007/0042410 A1 Feb. 22, 2007

Related U.S. Application Data

(62) Division of application No. 10/791,791, filed on Mar. 4, 2004.

(30) Foreign Application Priority Data

Mar. 4, 2003 (JP) .............................. 2003/057677

(51) Int. Cl.
*C07K 14/39* (2006.01)
*C07K 14/395* (2006.01)
(52) U.S. Cl. ..................................................... 530/350
(58) Field of Classification Search ...................... None
See application file for complete search history.

(56) References Cited

U.S. PATENT DOCUMENTS 4,885,357 A * 12/1989 Larkins et al. .............. 530/373
6,326,184 B1  12/2001 Gjermansen et al.

OTHER PUBLICATIONS

Avram et al., "SSU 1 Encodes a Plasma Membrane Protein with a Central Role in a Network of Proteins Conferring Sulfite Tolerance in *Saccharomyces cerevisiae*," *Journal of Bacteriology*, 1997, vol. 179, No. 18, pp. 5971-5974, American Society of Microbiology, Washington, D.C.
Becker et al., "High-Efficiency Transformation of Yeast by Electroporation," *Methods in Enzymology*, 1991, vol. 194, pp. 182-187, Academic Press, Inc., New York.
Blattner et al., "The Complete Genome Sequence of *Escherichia coli* K-12," *Science*, 1977, vol. 277, pp. 1453-1462, American Association for the Advancement of Science, Washington, D.C.
Carter et al., "Improved oligonucleotide site-directed mutagenesis using M13 vectors," *Nucleic Acids Research*, 1985, vol. 13, No. 12, pp. 4431-4443, Oxford University Press, Oxford, England.
Cole et al., "Deciphering the biology of Mycobacterium tuberculosis from the complete genome sequence," *Nature*, 1998, vol. 393, pp. 537-544, Nature Publishing Group, London, England.
Gjermansen, C., "Construction of a Hybrid Brewing Strain of Saccharomyces Carlsbergensis by Mating of Meiotic Segregants," *Carlsberg Res. Commun.*, 1981, vol. 46, pp. 1-11, Copenhagen Valby, Denmark.

Goldstein et al., "Three New Dominant Drug Resistance Cassettes for Gene Disruption in *Saccharomyces cerevisia*," Yeast, 1999, vol. 15, pp. 1541-1553, Wiley & Sons, Chichester, England and New York.
Goto-Yamamoto et al., "SSU1-R, a Sulphite Resistance Gene of Wine Yeast, is an Allele of SSU1 with a Different Upstream Sequence," Journal of Fermentation of Bioengineering, 1988, vol. 86, No. 10, pp. 427-433.
Hansen et al., "Inactivation of MET 10 in brewer's yeast specifically increases $SO_2$ formation during beer production," *Nature Biotechnology*, 1996, vol. 14, Nature America, New York. pp. 1587-1591.
Hansen et al., "Modification of biochemical pathways in industrial yeasts," Journal of Biotechnology, 1996, pp. 1-12, vol. 49, Elsevier Science, Amsterdam, Holland.
Hinnen et al., "Transformation of yeast," *Proc. Natl. Acad. Sci. USA*, 1978, vol. 75, No. 4, pp. 1929-1933, National Academy of Sciences, Washington, D.C.
Hussain et al., "Characterization of PDR4, a *Saccharomyces cerevisiae* gene that confers pleiotropic drug resistance in high-copy number," *Gene*, 1991, vol. 101, pp. 149-152, Elsevier, Amsterdam, Holland.
Ito et al., "Transformation of Intact Yeast Cells Treated with Alkali Cations," *Journal of Bacteriology*, 1983, vol. 153, No. 1, pp. 163-168, American Society for Microbiology, Washington, D.C.
Johannesen, "*Saccharomyces pastorianus* adenosine-5'-phosphosulfate kinase (MET14-CA) gene," GenBank Database Online, 2002, Database Accession No. AY 017216, XP-002285924.
Johannesen et al., "Differential transcriptional regulation of sulfur assimilation gene homologues in the *Saccharomyces carlsbergensis* yeast species hybrid," FEMS Yeast Research, 2002, pp. 315-322, vol. 1, No. 4, Elsevier Science B.V., Amsterdam, Holland.
Joubert et al., "Identification by mass spectrometry to two-dimensional gel electrophoresis-separated proteins extracted from lager brewing yeast," Electrophoresis, vol. 22, 2001, pp. 2969-2982, Wiley-VCH, Weinheim, Germany.

(Continued)

*Primary Examiner*—James Martinell
(74) *Attorney, Agent, or Firm*—Drinker Biddle & Reath LLP

(57) ABSTRACT

Provided herein are a method for selecting a gene participating in the desired brewing character and compiling a database of the whole genome sequence of industrial yeast; identifying a gene participating in a brewing characteristic from the database; functional analysis of the gene; and a DNA array of the whole genome sequences of an industrial yeast. Also provided are a method for yeast breeding; a method of producing an alcoholic beverage with improved quality; and a screening method to identify genes that increase productivity and/or improve flavor in the production of an alcohol or an alcoholic beverage by (A) analyzing a whole industrial yeast genome sequence, (B) comparing the genome sequence with the genome sequence of *S. cerevisiae*, (C) selecting a gene of the industrial yeast encoding having 70 to 97% identity to an amino acid sequence of *S. cerevisiae*; and (D) analyzing the selected gene.

6 Claims, 13 Drawing Sheets

OTHER PUBLICATIONS

Karin et al., "Primary structure and transcription of an amplified genetic locus: The CUP1 locus of yeast," *Proc. Natl. Acad. Sci. USA*, 1984, vol. 81, pp. 337-341, National Academy of Sciences, Washington, D.C.

Korch et al., "A mechanism for sulfite production in beer and how to increase sulfite levels by recombinant genetics," *Yeast and Fermentation*, pp. 201-208, 1991.

Kunkel, T., "Rapid and Efficient site-specific mutagenesis without phenotypic selection," *Proc. Natl. Acad. Sci. USA*, 1985, vol. 82, pp. 488-492, National Academy of Sciences, Washington, D.C.

Lashkari et al., "Yeast microarrays for genome wide parallel genetic and gene expression analysis," Proc. Natl. Acad. Sci. USA, 1997, pp. 13057-13062, vol. 94, National Academy of Sciences, Washington, D.C.

Makino et al., "Complete Nucleotide Sequences of 93-kb and 3.3-kb Plasmids of an Enterohemorrhagic *Escherichia coli* O157:H7 Derived from Sakai Outbreak," DNA Research, 1998, vol. 5, pp. 1-9, Kazusa DNA Research Institute & Universal Academy Press, Tokyo, Japan.

Martini et al., "Deoxyribonucleic Acid Relatedness among Species of the Genus *Saccharomyces* Sensu Stricto," *International Journal of Systematic Bacteriology*, 1985, vol. 35, No. 4, pp. 508-511.

Matasuzaki, *Saccharomyces bayanus* MET14 gene for adenosine-5'-phosphosulfate 3'-phosphotransferase, 2000, Abstract, submitted to the EMBL/GenBank/DDBJ databases. AB 049836.

Olesen et al., "The Dynamics of the *Saccharomyces carlsbergensis* brewing yeast transcriptome during a production-scale lager beer fermentation," *FEM Yeast Research*, 2000, vol. 2, pp. 563-573, Elsevier Science, Amsterdam, Holland.

Park et al., "SSU1 mediates sulphite efflux in *Saccharomyces cerevisiae,*" *Yeast*, 2000, vol. 16, pp. 881-888, John Wiley & Sons, Chichester, England and New York.

Sanger, F., "Determination of Nucleotide Sequences in DNA," Science, 1981, vol. 214, pp. 1205-1215, American Association for the Advancement of Science, Washington, D.C.

Sijen et al., Transcriptional and posttranscriptional gene silencing are mechanistically related, *Current Biology*, 2001, vol. 11, pp. 436-440, Current Biology, London, England.

Tamai et al., "Co-existence of Two Types of Chromosome in the Bottom Fermenting Yeast, *Sacchaomyces cerevisiae*," Yeast, 1998, vol. 10, pp. 923-933, Wiley & Sons, Ltd., Chichester, England & New York.

Waterman, M., "Computer Analysis of Nucleic Acid Sequences," Methods in Enzymology, 1988, vol. 164, pp. 765-793, Academic Press, New York.

Wells et al., "Cassette mutagenesis: an efficient method for generation of multiple mutations at defined sites," *Gene*, 1985, vol. 34, pp. 315-323, Elsevier, Amsterdam, Holland.

Winzeler et al., "Genetic Diversity in Yeast Assessed with Whole-Genome Oligonucleotide Arrays," Genetics, 2003, pp. 79-89, vol. 163, Bethesda, Maryland.

Wodicka et al., "Genome-wide edprssion monitoring in *Saccharomyces cerevisiae*," Nature Biotechnology, 1997, pp. 1359-1367, vol. 15, Nature America, New York.

* cited by examiner

Fig. 1
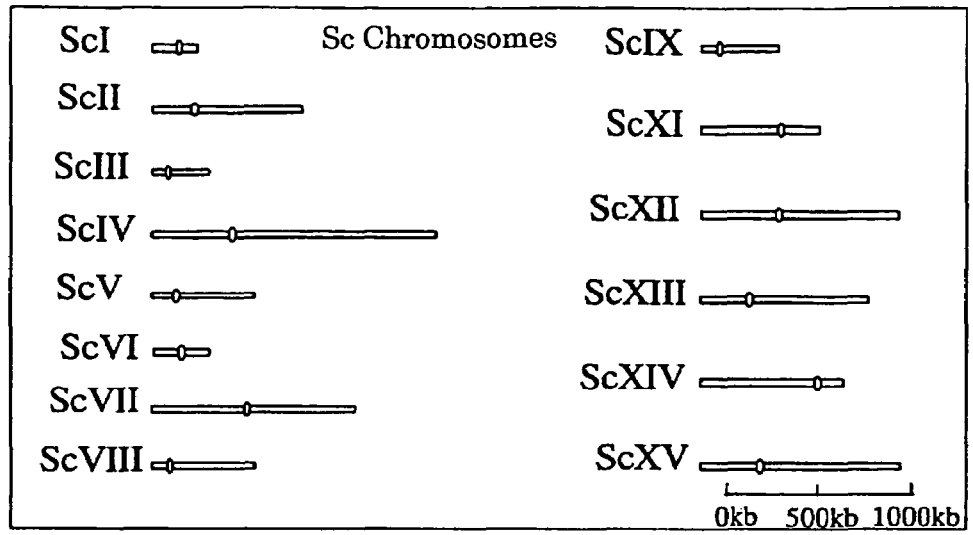
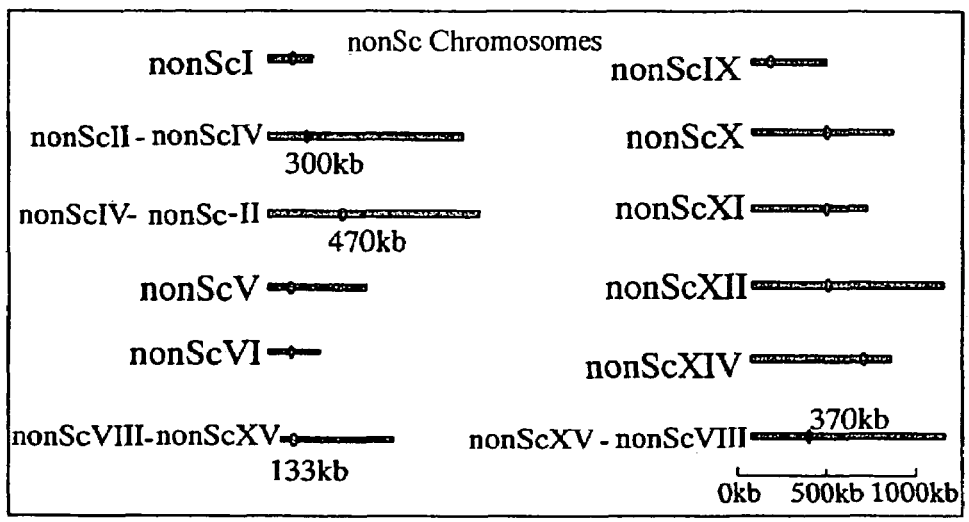
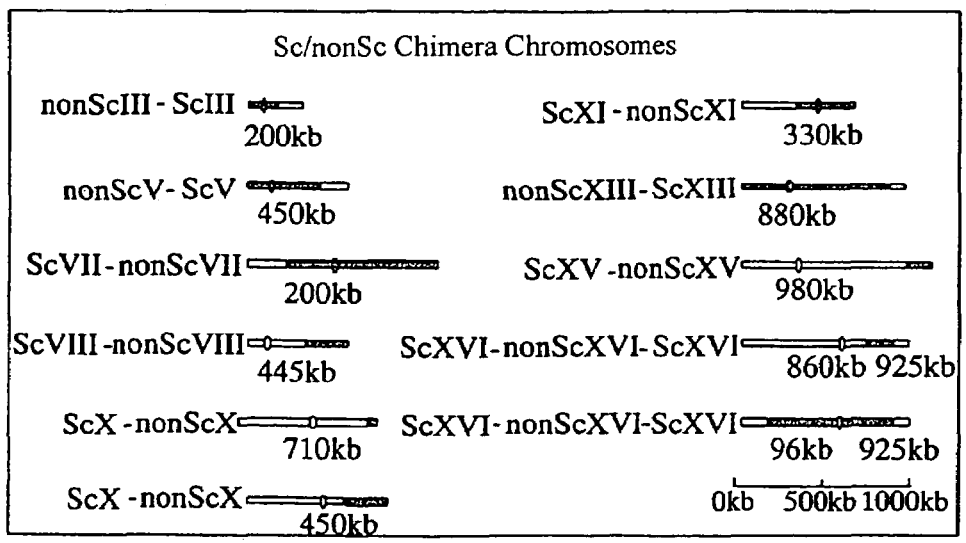

Fig. 7
(a)
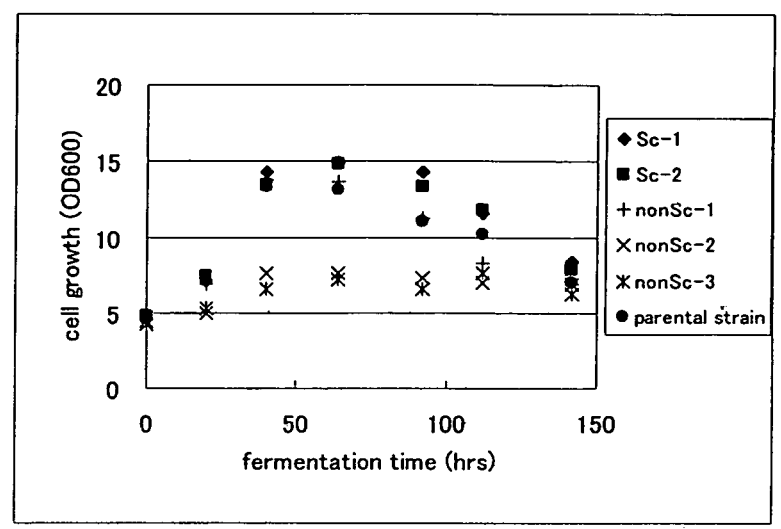
(b)
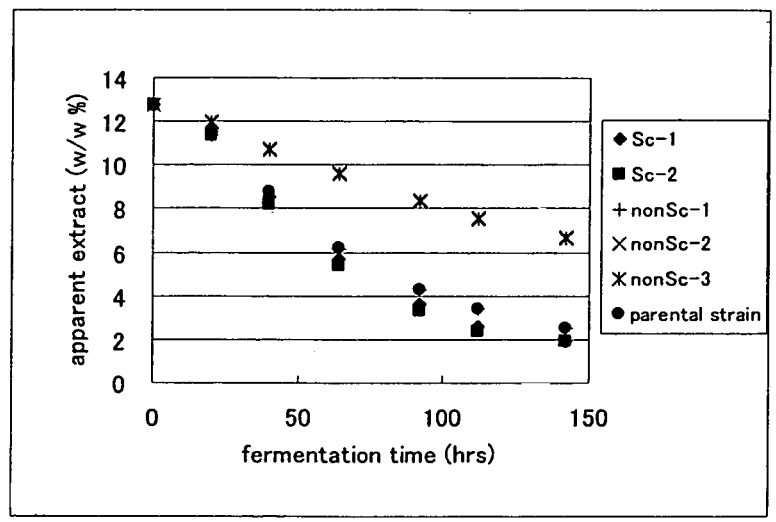
(c)
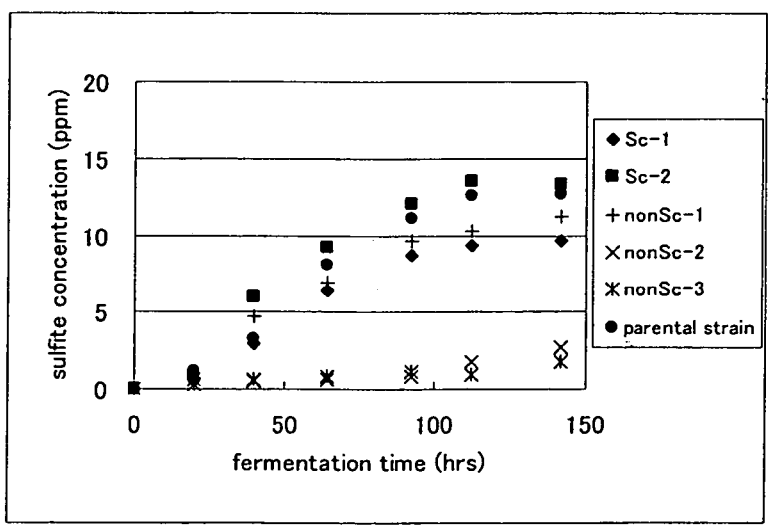

Fig. 8
(a)
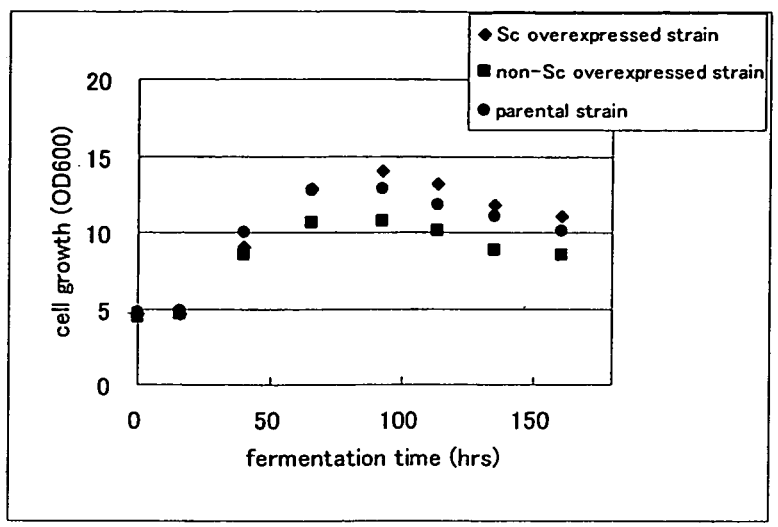
(b)
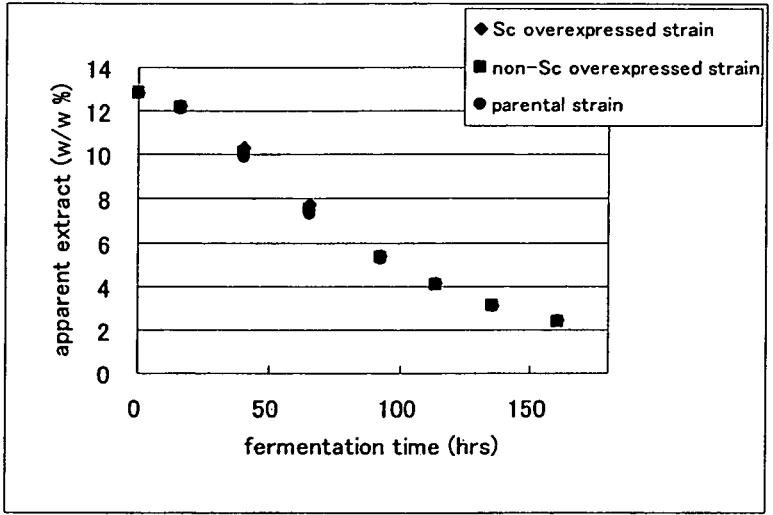
(c)
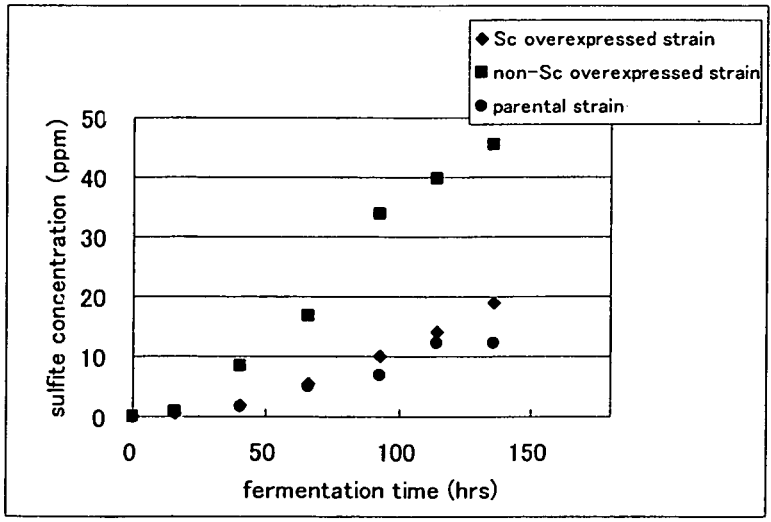

ScSSU1

```
   1 atggttgcca attgggtact tgctcttacg aggcagtttg accccttcat
  51 gtttatgatg gtcatgggtg tcggcatttc atcgaatatt ctatatagct
 101 tcccatatcc tgcaaggtgg ctaagaatat gctcctacat catgtttgct
 151 atcacttgcc ttattttcat tgctgtgcag gcactacaaa tattacattt
 201 gattgtctat attaaggaga aaagcttcag agaatatttt aatgactttt
 251 tcagaaatat gaagcacagt ttattttggg gtacttatcc catggggtta
 301 gttacaatta taaatttctt aggagcactc tcgaaagcga acacgacgaa
 351 gagccccact aattccagaa atttgatgat atttgtttac gtcttgtggt
 401 ggtatgatct cgcagtctgt ctagtaatag cgtggggtat ctcgtttctc
 451 atctggcatg actattactc tttggaaggg attgggaatc atccttcata
 501 taatatcaaa atggcatccg aaaacatgaa aagtgtattg ctactggata
 551 tcattccgct ggttgtcgtc gcttcaagtt gtggaacatt cacaatgtca
 601 gaaatattct tccatgcgtt taatagaaat attcaactga taacgttggt
 651 catatgtgcc ttaacgtggc tgcatgccat tatcttcgtc ttcatactga
 701 ttgcgatata cttctggagt cttatatta ataagatacc accaatgaca
 751 caggttttca ccttattcct gcttttgggc ccgatgggcc aaggaagtty
 801 tggagtctta ttgcttacag ataatataaa aaaatatgcg ggcaaatatt
 851 acccaacaga taacattaca agagaacaag agatattgac tattgcagtt
 901 ccatggtgtt tcaaaattct aggcatggtt tctgctatgg cattgctcgc
 951 tatgggctat tttttcaccg tgatttctgt cgtttcaatc ctgtcgtact
1001 acaataaaaa agagattgaa aacgagacag gaaaagtgaa gagagtttat
1051 accttccaca aaggtttttg ggggatgact ttcccgatgg gtactatgtc
1101 tttaggaaac gaagagttat atgtgcagta taccagtac gttcccttat
1151 atgcatttag agtcctagga accatatacg gcggtgtttg cgtttgttgg
1201 tcaattctat gccttttatg cacattgcat gagtattcta aaaagatgct
1251 gcatgctgcc cgtaaatctt cattattttc agagtcaggt acggaaaaga
1301 cgacagtttc tccgtataac agcattgaaa gcgtggaaga atcaaactcg
1351 gctctagatt ttacgcgttt agcataa    (SEQ ID NO: 34)
```

FIG. 10A

NonScSSU1

```
   1 atggtcgcta gttggatgct cactgccaca agggatttca acccttcat
  51 gtttgtcatg gttattgggg tcggtatttc atcgaatatt ctgtacagct
 101 tcccgtatcc ggcgaggtgg ctgaggatat gctcgtacat catgtttgcc
 151 attacatgtt tgattttcat ctctgtacag gcgctgcagc ttttgcacat
 201 ggtcatctat atcaaagaaa aaagctttag agattacttc aatgaatatt
 251 tcagaagtct gaagtacaat ttattttggg gtacttatcc catgggatta
 301 gtaacaatca taaattttt gggggcgctg tcacaaaaat ttaccacgac
 351 aagccctgcg aatgccaagc acttgatcat ttttgtttac gtcctgtggt
 401 ggtatgacct cgcggtttgt ttagtaaccg cttgggggat ttcattcctc
 451 atctggcaaa agtactactt cgtggacggg gttggaaatc actcttcata
 501 cagttcacga atggcttccg accacatgaa aagcgtactg ttgctagata
 551 tcattccgct ggtcgttgtc gcttcgagcg gtgggacatt tacaatgtca
 601 aaaatattcg gtaccacttt tgataggaat attcaattgc taacactggt
 651 catctgtgcc ctggtttggc tacacgctct tatatttgtc tttattctga
 701 ttacaatata cttctggaat ctttacatca ataagatacc accaatgacg
 751 caggtattta cgttgttctt ggtattgggg ccattgggcc aaggaagttt
 801 tggtattttg ttgcttactg acaatataag aaagtatgta gaaaaatact
 851 acccaaggga aaacatcacc atggaacaag aaatactaac cattatggtt
 901 ccgtggtgtt tcaaggttct gggcatgaca tttgctttgg cattaatcgc
 951 tatgggttac ttctttacgg taatttccct tatttcgatt ttatcatact
1001 acaatgaaag agttgttgac aatgaaacag gcaaagtgaa aaggatctac
1051 actttccata aaggtttctg ggggatgact ttcccgatgg gtaccatgtc
1101 tttgggaaac gaggagctgt atctgcaata caaccagtat gttcccttat
1151 atgcattcag agtcatagct accatatatg gtggtatttg tgtttgctgg
1201 tcaatcttat gcctctcgtg cacgttgtat ggttacctga aaacgattct
1251 ccatgctgcc cgtaaacctt cgtttttatc agaggaaggg acggagaaga
1301 ctgtcaattc tcctttcaac agcatcgaaa gtgtggagga atcaaactcg
1351 gctatcgata gtacatattt aacataa   (SEQ ID NO: 1)
```

FIG. 10B

ScMET14

```
  1 atggctacta atattacttg gcatccaaat cttacttacg acgaacgcaa
 51 ggcattgaga aaacaggacg gttgtactat ttggttaaca ggtctaagtg
101 cgtcaggtaa aagtacaatc gcctgtcgc tagaacagtt actgctccaa
151 aaaaacttgt ctgcatatag attggatggt gacaacattc gttttggatt
201 gaacaaggat ttgggtttct cagaaaagga cagaaatgaa aacattcgta
251 gaattagcga agtttctaag ctatttgctg attcatgtgc tatttcaatc
301 acctcattta tctctccata cagagttgac agagatagag ctcgtgaact
351 acataaggag gctggtttga agttcattga aatatttgtt gatgttccat
401 tagaagtcgc tgagcaaagg gaccctaagg gtttatacaa gaaagctagg
451 gagggtgtaa tcaaggagtt tacaggtatt tctgccccat atgaagcgcc
501 aaaagctcca gagctacatt tgagaaccga ccagaagacg gttgaagaat
551 gtgctaccat tatttatgag tacttaatca gtgaaaaaat catccgtaag
601 catttgtaa  (SEQ ID NO: 35)
```

NonScMET14

```
  1 atggctacta atatcacttg gcatccaaat cttacctacg acgaacgtaa
 51 ggaattaaga aagcaagacg gctgtaccgt ttggttgacc ggtctaagtg
101 cgtcaggaaa aagtacaata gcttgtgcac tggaacaatt actgcttcaa
151 aaaaacttat ctgcttatag gttagatggt gataacattc gttttggttt
201 gaataaggat ttgggcttct cagaaaagga cagaaatgaa aacattcgta
251 gaattagtga agtatccaag ctattcgctg attcgtgtgc tgtatccatc
301 acttcattta tttccccata cagagtcgat agagacagag cccgtgattt
351 acataaggaa gcaggcttga agttcattga aatttttgtt gatgttccat
401 tagaagtcgc tgagcaaaga gaccctaagg gtttgtataa gaaagccaga
451 gaaggtgtga ttaaagagtt cactggtatt tcagctcctt acgaagctcc
501 aaaggcccca gagttgcatt taagaactga ccaaaagact gttgaagaat
551 gtgctgctat catttatgag tacctggtca atgagaagat tatccggaag
601 catctataa  (SEQ ID NO: 2)
```

FIG. 11

Fig. 12
(a)
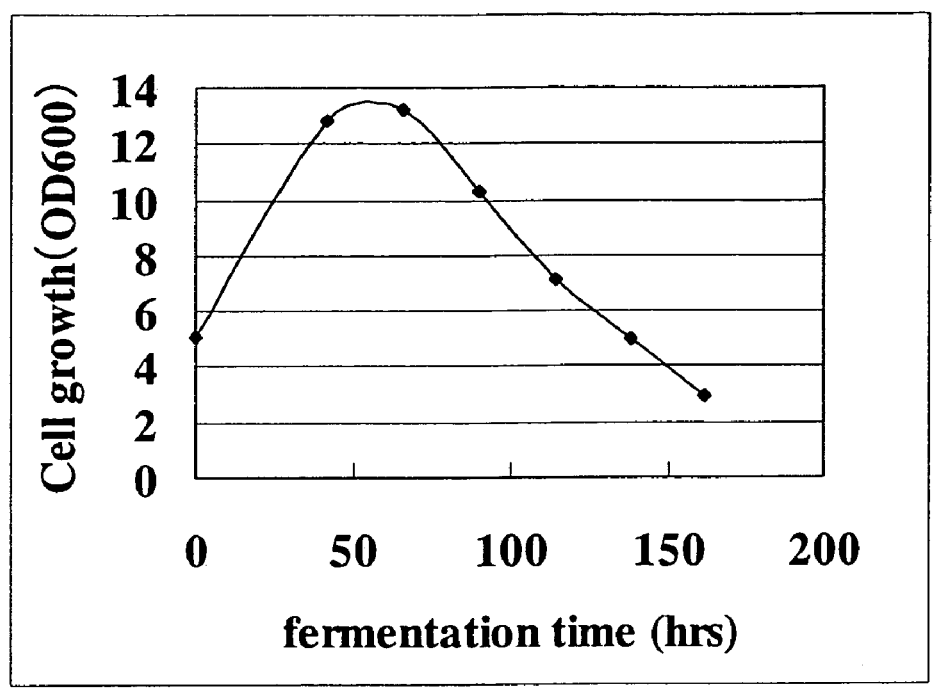
(b)
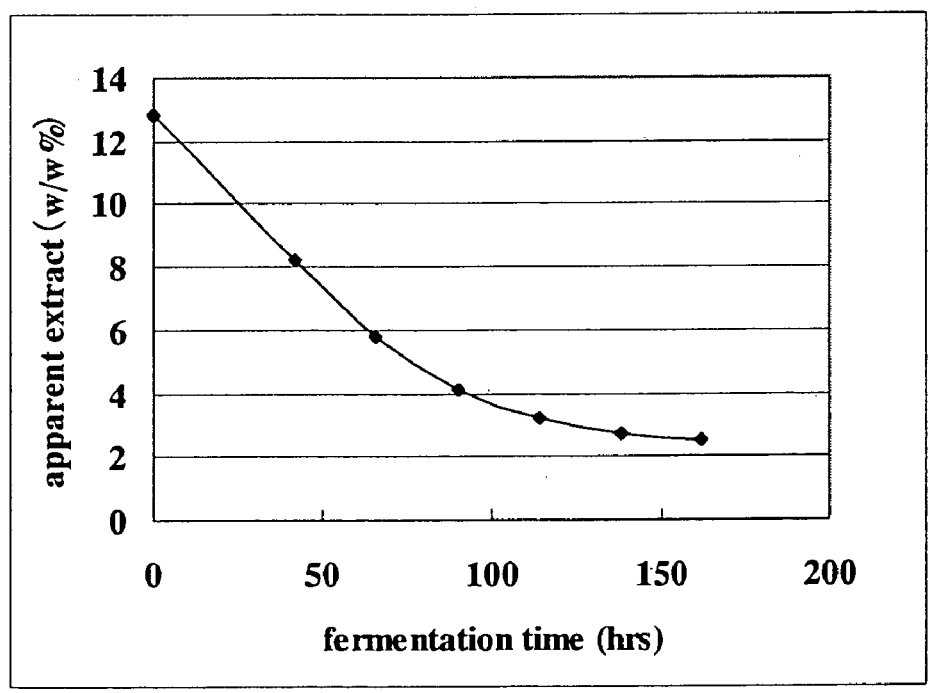

SEQUENCE LISTING

<160> NUMBER OF SEQ ID NOS: 37

<210> SEQ ID NO 1
<211> LENGTH: 1377
<212> TYPE: DNA
<213> ORGANISM: Saccharomyces sp.

<400> SEQUENCE: 1

```
atggtcgcta gttggatgct cactgccaca agggatttca acoctttcat gtttgtcatg      60 gttatggggg tcggtatttc atcgaatatt ctgtacagct tcccgtatcc ggcgaggtgg     120
ctgaggatat gctcgtacat catgtttgcc attacatgtt tgattttcat ctctgtacag     180
gcgctgcagc ttttgcacat ggtcatctat atcaaagaaa aaagctttag agattacttc     240
aatgaatatt tcagaagtct gaagtacaat ttattttggg gtacttatcc catgggatta     300
gtaacaatca taaattttt ggggcgctg tcacaaaaat ttaccacgac aagccctgcg      360
aatgccaagc acttgatcat ttttgtttac gtcctgtggt ggtatgacct cgcggtttgt     420
ttagtaaccg cttgggggat ttcattcctc atctggcaaa agtactactt cgtggacggg     480
```

```
gttggaaatc actcttcata cagttcacga atggcttccg accacatgaa aagcgtactg      540
ttgctagata tcattccgct ggtcgttgtc gcttcgagcg gtgggacatt tacaatgtca      600
aaaatattcg gtaccacttt tgataggaat attcaattgc taacactggt catctgtgcc      660
ctggtttggc tacacgctct tatatttgtc tttattctga ttacaatata cttctggaat      720
ctttacatca ataagatacc accaatgacg caggtattta cgttgttctt ggtattgggg      780
ccattgggcc aaggaagttt tggtattttg ttgcttactg acaatataag aaagtatgta      840
gaaaaatact acccaaggga aaacatcacc atggaacaag aaatactaac cattatggtt      900
ccgtggtgtt tcaaggttct gggcatgaca tttgctttgg cattaatcgc tatgggttac      960
ttctttacgg taatttccct tatttcgatt ttatcatact acaatgaaag agttgttgac     1020
aatgaaacag gcaaagtgaa aaggatctac actttccata aaggtttctg ggggatgact     1080
ttcccgatgg gtaccatgtc tttgggaaac gaggagctgt atctgcaata caaccagtat     1140
gttcccttat atgcattcag agtcatagct accatatatg gtggtatttg tgtttgctgg     1200
tcaatcttat gcctctcgtg cacgttgtat ggttacctga aaacgattct ccatgctgcc     1260
cgtaaacctt cgtttttatc agaggaaggg acggagaaga ctgtcaattc tccttttcaac    1320 agcatcgaaa gtgtggagga atcaaactcg gctatcgata gtacatattt aacataa       1377

<210> SEQ ID NO 2
<211> LENGTH: 609
<212> TYPE: DNA
<213> ORGANISM: Saccharomyces sp.

<400> SEQUENCE: 2
atggctacta atatcacttg gcatccaaat cttacctacg acgaacgtaa ggaattaaga       60
aagcaagacg gctgtaccgt ttggttgacc ggtctaagtg cgtcaggaaa aagtacaata      120
gcttgtgcac tggaacaatt actgcttcaa aaaaacttat ctgcttatag gttagatggt      180
gataacattc gttttggttt gaataaggat ttgggcttct cagaaaagga cagaaatgaa      240
aacattcgta gaattagtga agtatccaag ctattcgctg attcgtgtgc tgtatccatc      300 acttcatttta tttccccata cagagtcgat agagacagag cccgtgattt acataaggaa      360
gcaggcttga agttcattga aatttttgtt gatgttccat agaagtcgc tgagcaaaga       420 gaccctaagg gtttgtataa gaaagccaga gaaggtgtga ttaaagagtt cactggtatt       480
tcagctcctt acgaagctcc aaaggcccca gagttgcatt taagaactga ccaaaagact       540
gttgaagaat gtgctgctat catttatgag tacctggtca atgagaagat tatccggaag       600
catctataa                                                              609

<210> SEQ ID NO 3
<211> LENGTH: 458
<212> TYPE: PRT
<213> ORGANISM: Saccharomyces sp.

<400> SEQUENCE: 3

Met Val Ala Ser Trp Met Leu Thr Ala Thr Arg Asp Phe Asn Pro Phe
  1               5                  10                  15

Met Phe Val Met Val Met Gly Val Gly Ile Ser Ser Asn Ile Leu Tyr
                 20                  25                  30

Ser Phe Pro Tyr Pro Ala Arg Trp Leu Arg Ile Cys Ser Thr Ile Met
             35                  40                  45

Phe Ala Ile Thr Cys Leu Ile Phe Ile Ser Val Gln Ala Leu Gln Leu
         50                  55                  60
```

```
Leu His Met Val Ile Tyr Ile Lys Glu Lys Ser Phe Arg Asp Tyr Phe
 65                  70                  75                  80

Asn Glu Tyr Phe Arg Ser Leu Lys Tyr Asn Leu Phe Trp Gly Thr Tyr
                 85                  90                  95

Pro Met Gly Leu Val Thr Ile Ile Asn Phe Leu Gly Ala Leu Ser Gln
                100                 105                 110

Lys Phe Thr Thr Thr Ser Pro Ala Asn Ala Lys His Leu Ile Ile Phe
                115                 120                 125

Val Tyr Val Leu Trp Trp Tyr Asp Leu Ala Val Cys Leu Val Thr Ala
130                 135                 140

Trp Gly Ile Ser Phe Leu Ile Trp Gln Lys Tyr Tyr Phe Val Asp Gly
145                 150                 155                 160

Val Gly Asn His Ser Ser Tyr Ser Ser Arg Met Ala Ser Asp His Met
                165                 170                 175

Lys Ser Val Leu Leu Leu Asp Ile Ile Pro Leu Val Val Val Ala Ser
                180                 185                 190

Ser Gly Gly Thr Phe Thr Met Ser Lys Ile Phe Gly Thr Thr Phe Asp
                195                 200                 205

Arg Asn Ile Gln Leu Leu Thr Leu Val Ile Cys Ala Leu Val Trp Leu
210                 215                 220

His Ala Leu Ile Phe Val Phe Ile Leu Ile Thr Ile Tyr Phe Trp Asn
225                 230                 235                 240

Leu Tyr Ile Asn Lys Ile Pro Pro Met Thr Gln Val Phe Thr Leu Phe
                245                 250                 255

Leu Val Leu Gly Pro Leu Gly Gln Gly Ser Phe Gly Ile Leu Leu Leu
                260                 265                 270

Thr Asp Asn Ile Arg Lys Tyr Val Glu Lys Tyr Tyr Pro Arg Glu Asn
                275                 280                 285

Ile Thr Met Glu Gln Glu Ile Leu Thr Ile Met Val Pro Trp Cys Phe
290                 295                 300

Lys Val Leu Gly Met Thr Phe Ala Leu Ala Leu Ile Ala Met Gly Tyr
305                 310                 315                 320

Phe Phe Thr Val Ile Ser Leu Ile Ser Ile Leu Ser Tyr Tyr Asn Glu
                325                 330                 335

Arg Val Val Asp Asn Glu Thr Gly Lys Val Lys Arg Ile Tyr Thr Phe
                340                 345                 350

His Lys Gly Phe Trp Gly Met Thr Phe Pro Met Gly Thr Met Ser Leu
                355                 360                 365

Gly Asn Glu Glu Leu Tyr Leu Gln Tyr Asn Gln Tyr Val Pro Leu Tyr
370                 375                 380

Ala Phe Arg Val Ile Ala Thr Ile Tyr Gly Gly Ile Cys Val Cys Trp
385                 390                 395                 400

Ser Ile Leu Cys Leu Ser Cys Thr Leu Tyr Gly Tyr Leu Lys Thr Ile
                405                 410                 415

Leu His Ala Ala Arg Lys Pro Ser Phe Leu Ser Glu Glu Gly Thr Glu
                420                 425                 430

Lys Thr Val Asn Ser Pro Phe Asn Ser Ile Glu Ser Val Glu Glu Ser
                435                 440                 445

Asn Ser Ala Ile Asp Ser Thr Tyr Leu Thr
450                 455

<210> SEQ ID NO 4
<211> LENGTH: 202
```

-continued

```
<212> TYPE: PRT
<213> ORGANISM: Saccharomyces sp.

<400> SEQUENCE: 4

Met Ala Thr Asn Ile Thr Trp His Pro Asn Leu Thr Tyr Asp Glu Arg
 1               5                  10                  15

Lys Glu Leu Arg Lys Gln Asp Gly Cys Thr Val Trp Leu Thr Gly Leu
             20                  25                  30

Ser Ala Ser Gly Lys Ser Thr Ile Ala Cys Ala Leu Glu Gln Leu Leu
         35                  40                  45

Leu Gln Lys Asn Leu Ser Ala Tyr Arg Leu Asp Gly Asp Asn Ile Arg
     50                  55                  60

Phe Gly Leu Asn Lys Asp Leu Gly Phe Ser Glu Lys Asp Arg Asn Glu
 65                  70                  75                  80

Asn Ile Arg Arg Ile Ser Glu Val Ser Lys Leu Phe Ala Asp Ser Cys
                 85                  90                  95

Ala Val Ser Ile Thr Ser Phe Ile Ser Pro Tyr Arg Val Asp Arg Asp
            100                 105                 110

Arg Ala Arg Asp Leu His Lys Glu Ala Gly Leu Lys Phe Ile Glu Ile
        115                 120                 125

Phe Val Asp Val Pro Leu Glu Val Ala Glu Gln Arg Asp Pro Lys Gly
130                 135                 140

Leu Tyr Lys Lys Ala Arg Glu Gly Val Ile Lys Glu Phe Thr Gly Ile
145                 150                 155                 160

Ser Ala Pro Tyr Glu Ala Pro Lys Ala Pro Glu Leu His Leu Arg Thr
                165                 170                 175

Asp Gln Lys Thr Val Glu Glu Cys Ala Ala Ile Ile Tyr Glu Tyr Leu
            180                 185                 190

Val Asn Glu Lys Ile Ile Arg Lys His Leu
        195                 200

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agtcacgacg ttgta                                                    15

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caggaaacag ctatgac                                                  17

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 7
aggcgtatca cgaggccctt tc                                              22

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cttatcgatg ataagcggtc aaacatgag                                       29

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgcaagctcc gtacgttcaa cattcttatg aacggc                               36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcatcatcgt cgtgatcctt ctttggcaaa tgcagg                               36

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcgggtattt tgatggtaaa tctacaagcc ctcggc                               36

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cccagacaca gtttccagta tcatcctcgc agaac                                35

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
```
gagctcatgg tcgctagttg gatgct                                                26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agatctcagc ttcagcccaa tccatt                                                26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gagctcatgg ttgccaattg ggtact                                                26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agatctctcc tacatgaaat gcttgc                                                26

<210> SEQ ID NO 17
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
atggtcgcta gttggatgct cactgccaca agggatttca acccttttcat atcgaatatt         60 ctgtacagct gtttgtcatg gttatggggg tcggtatttc ccttgacagt cttgacgtgc 1        20

<210> SEQ ID NO 18
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgttaaatat gtactatcga tagccgagtt tgattcctcc acactttcga acagtcttct          60
ccgtcccttc tctgataaa tgctgttgaa aggagaattg cgcacttaac ttcgcatctg          120

<210> SEQ ID NO 19
<211> LENGTH: 120
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
atggttgcca attgggtact tgctcttacg aggcagtttg accccttcat gtttatgatg      60
gtcatgggtg tcggcatttc atcgaatatt ctatatagct ccttgacagt cttgacgtgc     120

<210> SEQ ID NO 20
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttatgctaaa cgcgtaaaat ctagagccga gtttgattct tccacgcttt caatgctgtt      60
atacggagaa actgtcgtct tttccgtacc tgactctgaa cgcacttaac ttcgcatctg     120

<210> SEQ ID NO 21
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atggtcgcta gttggatgct cactgccaca agggatttca acccttttcat gtttgtcatg     60 gttatggggg tcggtatttc atcgaatatt ctgtacagct ccggagctta ccagttctca    120

<210> SEQ ID NO 22
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tgttaaatat gtactatcga tagccgagtt tgattcctcc acactttcga tgctgttgaa      60
aggagaattg acagtcttct ccgtcccttc ctctgataaa tcgactctag aggatccaga    120

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tcgaaagcga acacgacgaa                                                  20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgacagaaat cacggtgaaa a                                                21

```
<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tgtcacaaaa atttaccacg ac                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aagggaaatt accgtaaaga ag                                              22

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
atgtttgtcg cacctgtatc t                                               21

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gattagaggc accatcac                                                   18

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctcgagctct cgtgaaattc attgaaacaa atg                                  33

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggatccttat aagatttata gatgcttccg                                      30
```

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
ctcgagctca gaaaagttgg aattatttct cca         33

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
ggatccaatg tacagtaatc ggtcaaatta         30

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
gaatcaatta acttatggtt tctta         25

<210> SEQ ID NO 34
<211> LENGTH: 1377
<212> TYPE: DNA
<213> ORGANISM: Saccharomyces sp.

<400> SEQUENCE: 34

| | |
|---|---|
| atggttgcca attgggtact tgctcttacg aggcagtttg acccctttcat gtttatgatg | 60 |
| gtcatgggtg tcggcatttc atcgaatatt ctatatagct tcccatatcc tgcaaggtgg | 120 |
| ctaagaatat gctcctacat catgtttgct atcgcttgcc ttattttcat tgctgtgcag | 180 |
| gcactacaaa tattcatttt gattgtctat attaaggaga aaagcttcag agaatatttt | 240 |
| aatgactttt tcagaaatat gaagcacagt ttattttggg gtacttatcc catggggtta | 300 |
| gttacaatta taaatttctt aggagcactc tcgaaagcga acacgacgaa gagccccact | 360 |
| aattccagaa atttgatgat atttgtttac gtcttgtggt ggtatgatct cgcagtctgt | 420 |
| ctagtaatag cgtggggtat ctcgtttctc atctggcatg actattactc tttggaaggg | 480 |
| attgggaatc atccttcata taatatcaaa atggcatccg aaaacatgaa aagtgtattg | 540 |
| ctactggata tcattccgct ggttgtcgtc gcttcaagtt gtggaacatt cacaatgtca | 600 |
| gaaatattct tccatgcgtt taatagaaat attcaactga taacgttggt catatgtgcc | 660 |
| ttaacgtggc tgcatgccat tatcttcgtc ttcatactga ttgcgatata cttctggagt | 720 |
| ctttatatta ataagatacc accaatgaca caggttttca ccttattcct gcttttgggc | 780 |
| ccgatgggcc aaggaagtty tggagtctta ttgcttacag ataatataaa aaaatatgcg | 840 |
| ggcaaatatt acccaacaga taacattaca agagaacaag agatattgac tattgcagtt | 900 |
| ccatggtgtt tcaaaattct aggcatggtt tctgctatgg cattgctcgc tatgggctat | 960 |

-continued

```
tttttcaccg tgatttctgt cgtttcaatc ctgtcgtact acaataaaaa agagattgaa      1020
aacgagacag gaaaagtgaa gagagtttat accttccaca aaggttttg ggggatgact       1080 ttcccgatgg gtactatgtc tttaggaaac gaagagttat atgtgcagta taaccagtac     1140
gttcccttat atgcatttag agtcctagga accatatacg gcggtgtttg cgtttgttgg     1200
tcaattctat gccttttatg cacattgcat gagtattcta aaaagatgct gcatgctgcc    1260
cgtaaatctt cattattttc agagtcaggt acggaaaaga cgacagtttc tccgtataac    1320
agcattgaaa gcgtggaaga atcaaactcg gctctagatt ttacgcgttt agcataa       1377
```

<210> SEQ ID NO 35
<211> LENGTH: 609
<212> TYPE: DNA
<213> ORGANISM: Saccharomyces sp.

<400> SEQUENCE: 35

```
atggctacta atattacttg gcatccaaat cttacttacg acgaacgcaa ggcattgaga      60
aaacaggacg gttgtactat ttggttaaca ggtctaagtg cgtcaggtaa aagtacaatc    120
gcctgtgcgc tagaacagtt actgctccaa aaaaacttgt ctgcatatag attggatggt    180
gacaacattc gttttggatt gaacaaggat ttgggtttct cagaaaagga cagaaatgaa    240
aacattcgta gaattagcga agtttctaag ctatttgctg attcatgtgc tatttcaatc    300
acctcattta tctctccata cagagttgac agagatagag ctcgtgaact acataaggag    360
gctggtttga agttcattga aatatttgtt gatgttccat tagaagtcgc tgagcaaagg    420
gaccctaagg gtttatacaa gaaagctagg gagggtgtaa tcaaggagtt tacaggtatt    480
tctgccccat atgaagcgcc aaaagctcca gagctacatt tgagaaccga ccagaagacg    540
gttgaagaat gtgctaccat tatttatgag tacttaatca gtgaaaaaat catccgtaag    600
catttgtaa                                                              609
```

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36

```
gaatcaatta acatatggtt tctta                                              25
```

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37

```
gaatcaatta acatatggtt tctta                                              25
```

SCREENING METHOD FOR GENES OF BREWING YEAST

This application is a divisional application of U.S. application Ser. No. 10/791,791, filed Mar. 4, 2004, which claims priority under 35 U.S.C. § 119 to Japanese Application No. 057677/2003, filed Mar. 4, 2003, both of which are incorporated by reference herein in their entirety.

BACKGROUND OF THE INVENTION

1. Field of the Invention

The present invention relates to a screening method for genes of an industrial yeast used for the production of an alcoholic beverage such as beer or sake, a fuel alcohol, etc. and particularly for genes of brewing yeast used for the production of an alcoholic beverage. More particularly, it relates to a method where, in the production of an alcoholic beverage, DNA sequence information of brewing yeast is compiled in a database so that the gene which participates in increase in productivity and/or improvement in flavor such as stabilization, reinforcement, etc. of the flavor is selected; a method for breeding yeast suitable for the brewing in which expression of a gene is controlled, such as yeast in which the selected gene is disrupted or yeast in which the gene is overexpressed; and a method for the production of an alcoholic beverage using the bred yeast.

2. Description of the Prior Art

Development of techniques for production of fuel alcohols, alcoholic beverages such as beer or sake, etc. has been carried out using industrial yeast. Especially in the production of an alcoholic beverage using brewing yeast, there has seen a brisk development in the techniques for increasing productivity and improving flavor such as stabilization or enhancement of flavor of an alcoholic beverage.

The most consumed alcoholic beverage in the world is beer and the amount of beer produced in the world in 2001 was about 140,000,000 kL. Type of beer is roughly classified into three depending upon type of yeast and fermentation method. The three types are, naturally fermented beer where fermentation is carried out utilizing yeast and microorganisms inhabiting in breweries; ale-type beer where fermentation is carried out using a top fermenting yeast belonging to Saccharomyces cerevisiae (hereinafter, abbreviated as S. cerevisiae) at the temperature of 20 to 25° C. and the following aging period is shortened; and lager-type beer where fermentation is carried out using a bottom fermenting yeast belonging to Saccharomyces pastorianus at the temperature of 6 to 15° C. and then subjected to a low-temperature aging. At present, not less than 90% of the beer produced in the world is a lager-type beer and, therefore, the bottom fermenting yeast that is used for brewing of the lager-type beer has been most widely used in beer brewing.

In the so-called fermentation production where production is carried out using a microorganism including the above-mentioned brewing yeast, it is important that the fermentation process is optimized and that the useful strain is selected and bred, in order to increase productivity and improve quality of the product.

In the case of optimization of beer brewing, there has been conducted a method where an amount of yeast metabolites such as alcohol (e.g. ethanol), ester, organic acid, etc. are monitored, and then temperature, quantity of airflow, content of raw material, etc. are controlled. In such a case, material uptake and excretion by yeast cells and metabolism in the cells are handled as a black box and only very superficial control is carried out. In addition, for the purpose of giving, for example, high flavor to an alcoholic beverage, a process control method for suppressing the amount of oxygen supply during beer brewing or the like has been tried. In such a method, however, growth rate of the yeast itself is reduced due to insufficient oxygen, and adverse effect such as retardation of fermentation and/or deterioration of beer quality may arise. Accordingly, there has been a limit on the improvement in productivity and quality of beer by means of optimization of fermentation processes.

On the other hand, with regard to a method of breeding useful industrial yeast such as useful beer yeast, a technique for selecting desirable strain has been widely used rather than actual breeding. Beer brewing per se has been performed since well before the discovery of microorganisms by Pasteur and, in the beer brewing, a method of selecting more suitable strain of beer yeast from many strains of yeast used in the beer brewery has been traditionally carried out while there have been few cases where beer yeast with good traits is positively bred.

As an example of a positive breeding method, there is a method where artificial mutagenesis by chemicals or radioactive rays is used. However, brewing yeast, particularly a bottom fermenting yeast which is widely used in beer brewing, is in many cases a polyploid. In that case, it is not possible to produce the desired mutant unless mutation takes place in all of the alleles to be mutated. Accordingly, although it is possible to induce desirable mutation in the case of a haploid laboratory yeast, it is substantially impossible in the case of beer yeast which is a polyploid.

In recent years, there has been tried a breeding where mutation or cross-breeding is carried out by using spores isolated from bottom fermenting yeast (c.f., for example, Non-Patent Document 1). However, the bottom fermenting yeast is a polyploid, and has complicated chromosome structure, therefore, isolation of spores having proliferation ability is difficult, and moreover it is almost impossible to obtain a strain with good traits therefrom.

On the other hand, it has recently become possible that desired genes are introduced and expressed in the brewing yeast using a genetic engineering technique, whereby it has become possible to breed yeast with the desired character by using the results of functional analysis of genes and the genes which have been functionally analyzed. However, as compared with the baker's yeast (S. cerevisiae; c.f., for example, Non-Patent Document 2) of which the whole genome sequence is already clarified, the whole genome sequence of the bottom fermenting yeast has not been clarified and there have been only a very few findings about the gene participating in brewing character specific to bottom fermenting yeast and about the function of the said gene in beer brewing.

In recent years, transcriptome analysis has been conducted using DNA microarray where DNA fragments or nucleotide oligomers, each of which has a partial sequence of structural gene or internal region of the chromosome are fixed on solid support. For example, Olesen, et al. conducted a comprehensive genetic expression analysis of bottom fermenting yeast during the brewing using GeneFilters (manufactured by Research Genetics Co.) (c.f., for example, Non-Patent Document 3). However, since the whole genome sequence of bottom fermenting yeast has not been clarified yet, it is ambiguous that what gene is monitored for its expression precisely. As a result, such information is quite insufficient to apply to metabolic analysis of bottom fermenting yeast, and to breeding of useful yeast, and to control of beer brewing process.

At present, the whole genome sequences of more than 100 species of microorganisms have been determined (c.f., for example, Non-Patent Document 6) including *S. cerevisiae*, *Escherichia coli* (c.f., for example, Non-Patent Document 4) and *Mycobacterium tuberculosis* (c.f., for example, Non-Patent Document 5). On the basis of the determined DNA sequences, genes of these microorganisms are identified and function of an enormous number of genes have been predicted without conducting genetic, biochemical and molecular biological experiments. However, industrial yeast such as brewing yeast which has high ploidy and complicated chromosome structure, and thus an assembly (an operation for connecting the DNA sequences) is presumed to be difficult. Therefore, the whole genome sequence of bottom fermenting yeast which contains two different types of genome (c.f., for example, Non-Patent Document 7) has not been reported yet.

In the production of specific alcohols or alcoholic beverages, there is a technique to increase concentration of sulfite in the product for control of flavor. Sulfite is known as a compound which has anti-oxidative activity, and has been widely used as an antioxidant in the fields of food, beverage and pharmaceuticals, and also in an alcoholic beverage. For example, in the case of wine that requires a long aging period, sulfite plays an important role for the preservation of its quality. It is also known that, in beer brewing, the quality preservation period becomes long in accordance with the increase in concentration of sulfite contained in the product. Thus, when the amount of sulfite in the product is increased, it is possible to prepare a product that has excellent flavor stability and a long quality preservation period.

The simplest way to increase the amount of sulfite in the product is addition of sulfite. In Japan, so far as wine is concerned, it is permitted by the Ministry of Health, Labor and Welfare to add sulfite to an extent of not more than 350 ppm in terms of residual sulfite concentration. In that case, however, since sulfite is categorized as food additives, it is not appropriate to add sulfite to beer when a negative image of consumers to food additives is taken into consideration.

However, the yeast used in brewing produces hydrogen sulfide by the reduction of sulfate in the medium in order to synthesize sulfur-containing metabolites such as sulfur-containing amino acids. Sulfite is an intermediate metabolite of this pathway. If sulfite is efficiently excreted outside the cells during fermentation period, the amount of sulfite both in the wort and in the product can be increased.

There are two methods for increasing sulfite concentration in the wort during fermentation. One is control of fermentation process and another is breeding of brewing yeast. As for control of fermentation process, amount of sulfite produced during fermentation is inversely proportional to the concentration of dissolved oxygen and, therefore, there has attempted, a method where the concentration of dissolved oxygen is reduced so that amount of sulfite is increased and at the same time the oxidation of sulfite is suppressed. However, in that method, growth rate of yeast is reduced due to lack of oxygen, which has negative effects such as retardation of fermentation and deterioration of quality. Therefore that method is not practical.

On the other hand, as mentioned above, a genetic engineering technique has been developed for breeding brewing yeast. For example, there are some reports focused on sulfur metabolism of yeast. Sulfite ($SO_2$) is an intermediate product of sulfur-containing amino acid and vitamin synthesis and is produced via a pathway of sulfate ion ($SO_4^{2-}$)→APS (adenyl sulfate)→PAPS (phosphoadenylyl sulfate)→sulfite ion ($SO_3^{2-}$) where the sulfate ion is incorporated from outside of the cells. There is an attempt that copy numbers of MET 3 gene participating in the reaction of sulfate ion ($SO_4^{2-}$)→APS (adenylyl sulfate) and of MET 14 gene participating in the reaction of APS (adenylyl sulfate)→PAPS (phosphoadenylyl sulfate) are increased to improve the ability of the yeast for the production of sulfite (c.f., for example, Non-Patent Document 8). There is another example of an attempt where reduction of sulfite ion ($SO_3^{2-}$) is inhibited by disruption of MET 10 gene whereby amount of sulfite produced by the yeast is increased (c.f., for example, Non-Patent Document 9). According to such attempts, amount of sulfite produced by an MET 10 gene disruptant is increased to an extent of not less than ten-fold of the parental strain, but on the other hand, some retardation in fermentation and increase in the amounts of acetaldehyde and 1-propanol in the beer are noted, which has become a problem for the practical use.

Accordingly, although development of breeding methods for industrial yeast such as brewing yeast using genetic engineering have been in progress, it is the current status that, due to insufficient genomic information of brewing yeast, selection of the gene participating in a brewing character of brewing yeast, analysis of function of protein encoded by the gene and utilization of those findings for breeding have not been sufficiently carried out.

Thus, a method for breeding yeast which shows the desired character without deterioration of fermentation speed and product quality has not been established yet and there has been a big demand for the development of such a method not only in the brewing industry but also in the industries where yeast is used.

(Non-Patent Document 1) C. Gjermansen: "Construction of a hybrid brewing strain of *Saccharomyces carlsbergensis* by mating of meiotic segregants", Carlsberg Res. Commun., volume 46, pages 1 to 11 (1981).

(Non-Patent Document 2) A. Goffeau, et al.: "The Yeast Genome Directory", Nature, volume 387, pages 5 to 105 (1997).

(Non-Patent Document 3) K. Olesen, et al.: "The dynamics of the *Saccharomyces carlsbergensis* brewing yeast transcriptome during a production-scale lager beer fermentation", FEMS Yeast Research, volume 2, pages 563 to 573 (2000).

(Non-Patent Document 4) F. R. Blattner, et al.: "The Complete Genome Sequence of *Escherichia coli* K-12", Science, volume 277, pages 1453-1462 (1997).

(Non-Patent Document 5) S. T. Cole, et al.; "Deciphering the biology of *Mycobacterium tuberculosis* from the complete genome sequence", Nature, volume 393, pages 537-544 (1998).

(Non-Patent Document 6) The National Center for Biotechnology Information, retrieved from the Internet: <URL: http://www.ncbi.nlm.nih.gov/PMGifs/Genomes/micr.html>.

(Non-Patent Document 7) Y. Tamai et al.: "Co-existence of two types of chromosome in the fermenting yeast, *Sacchaomyces cerevisiae*", Yeast, volume 10, pages 923-933 (1998).

(Non-Patent Document 8) C. Korch, et al.: Proc. Eur. Brew. Conv. Congress, Lisbon, pages 201-208 (1991).

(Non-Patent Document 9) J. Hansen, et al.: "Inactivation of MET 10 in brewer' s yeast specifically increases $SO_2$ formation during beer production", Nature Biotech., volume 14, pages 1587-1591 (1996).

(Non-Patent Document 10) T. Sijen, et al.: "Transcriptional and post transcriptional gene silencing are mechanistically related", Curr. Biol., volume 11, pages 436-440 (2001).

(Non-Patent Document 11) N; Goto, et al.: "SSU1-R, a sulphite resistance gene of wine yeast, is an allele of SSU 1 with a different upstream sequence", J. Ferment. Bioeng., volume 86, pages 427-433 (1998).

(Non-Patent Document 12) D. Avram, et al.: "SSU 1 encodes a plasma membrane protein with a central role in a network of proteins conferring sulfite tolerance in *Saccharomyces cerevisiae*", J. Bacteriol., volume 179, pages 5971-5974 (1997).

(Non-Patent Document 13) H. Park, et al.; "SSU 1 mediates sulphite efflux in *Saccharomyces cerevisiae*", Yeast, volume 16, pages 881-888 (2000).

SUMMARY OF THE INVENTION

An object of the present invention is to provide a method of selecting gene participating in the desired brewing character, which is achieved in such a manner that a database compiling the whole genome sequence (hereinafter, may be abbreviated as genomic DB) of industrial yeast, particularly brewing yeast used for an alcoholic beverage such as beer, is prepared; gene that the brewing yeast possesses is selected from the database; functional analysis of the gene is carried out by disruption or overexpression. Another object is to provide a breeding method of the yeast showing the brewing character which the said gene participates in and also a method of producing an alcohol or an alcoholic beverage where productivity and quality are improved using the said yeast. Still another object is to provide genes mentioned above and peptides encoded by the said genes.

It has been known that brewing yeast widely used for industrial purpose is a polyploid and especially, bottom fermenting yeast is an allopolyploid which is composed of at least two kinds of genomes. One of the genomes is thought to be a genome derived from *S. cerevisiae* of which the whole genome sequence has been clarified, while the source of another genome(s) has not been clarified yet.

The present inventors have determined the whole genome sequence of the bottom fermenting yeast in order to find unidentified genes displaying essential functions for excellent brewing. The amino acid sequences of the bottom fermenting yeast were then compared with those registered in the genomic DB for *S. cerevisiae*, and functions of proteins encoded by genes of the brewing yeast were estimated. As a result, it has been clarified that the genes of the bottom fermenting yeast are roughly classified into Sc type genes showing nearly 100% amino acid identity to *S. cerevisiae* and non-Sc type genes showing around 70 to 97% identify. Moreover, it has been clarified that the bottom fermenting yeast has complicated chromosome structure consists of Sc-type chromosomes, non-Sc-type chromosomes and Sc/non-Sc-type chimera chromosomes. Structure of the whole chromosomes of the bottom fermenting yeast is shown in FIG. 1. On the basis of genomic information clarified by the present invention, the present inventors have found such an unexpectedly complicated structure of chromosomes, and developed a screening method for the genes of bottom fermenting yeast. To be more specific, there has been achieved a screening method for genes participating in brewing characters specific to the brewing yeast, which is characterized in that (A) the whole genome sequence of industrial yeast, particularly bottom fermenting yeast which is one of the brewing yeasts, is analyzed, (B) the genome sequence is compared with the whole genome sequence of *S. cerevisiae*, (C) genes of the bottom fermenting yeast encoding amino acid sequences which have 70 to 97% identities to the amino acid sequences encoded by genes of *S. cerevisiae* are selected and (D) functional analysis of the selected genes are carried out, whereby the brewing character given to the yeast by the genes are identified. The present inventors have repeatedly carried out intensive investigations on the basis of those findings and accomplished the present invention.

Thus, the present invention relates to:

(1) A screening method for genes participating in increase in productivity and/or improvement in flavor in the production of an alcohol or an alcoholic beverage, characterized in that, (a) the whole genome sequence of industrial yeast is analyzed, (b) these sequence is compared with that of *Saccharomyces cerevisiae*, (c) gene of the industrial yeast encoding an amino acid sequence having 70 to 97% identity to an amino acid sequence encoded by the gene of *Saccharomyces cerevisiae* is selected and (d) functional analysis of the selected gene is carried out, whereby the character given to the yeast by the gene is identified;

(2) A screening method according to the above (1), wherein a DNA array is used for the functional analysis in (d) of the above (1).

(3) A method according to the above (2), wherein a DNA array, in which one or more of oligonucleotides comprising the following DNA sequence or its complementary DNA sequence is adhered to a solid support, is used;

DNA sequence (1) having 10 to 30 nucleotides existing in an open reading frame of the whole genome sequence of an industrial yeast and (2) not existing in the region other than the region of said 10 to 30 nucleotides sequence in the whole genome sequence;

(4) A method according to the above (2), wherein a DNA array, in which one or more of oligonucleotides hybridizing in a stringent condition to the oligonucleotides defined in the above (3) is/are adhered to a solid support, is used;

(5) A method according to the above (2), wherein a DNA array, in which one or more of oligonuclaeotides comprising the following DNA sequence or its complementarty DNA sequence is adhered to a solid support, is used;

DNA sequence (1) having 10 to 30 nucleotides existing in a non-coding region of the whole genome sequence of an industrial yeast and (2) not existing in the region other than the region of said 10 to 30 nucleotides sequence in the whole genome sequence;

(6) A method according to the above (2), wherein a DNA array, in which one or more of oligonucleotides hybridizing in a stringent condition to the oligonucleotides defined in the above (5) is/are adhered to a solid support, is used;

(7) A method according to the above (2), wherein a DNA array, in which oligonucleotides selected from two or more groups of the following 4 groups consisting of one or more of oligonucleotides defined in the above (3), one or more of oligonucleotides defined in the above (4), one or more of oligonucleotides defined in the above (5), and one or more of oligonucleotides defined in the above (6) are adhered to a solid support, is used;

(8) The screening method according to any of the above (1) to (7), wherein the industrial yeast is brewing yeast;

(9) The screening method according to any of the above (1) to (8), wherein the brewing yeast is beer yeast;

(10) Gene which is obtained by the screening method according to the above (1);

(11) The gene according to the above (10), which is characterized by that, when the gene mentioned in the above (10) is expressed in yeast, the concentration of sulfite in a culture medium of the yeast increases;

(12) DNA which comprises a DNA sequence represented by SEQ ID NO: 1 or 2, and DNA which hybridizes to the said DNA under stringent condition;

(13) DNA which encodes a polypeptide having an amino acid sequence represented by SEQ ID NO: 3 or 4, and DNA which encodes polypeptide having an amino acid sequence in which one to several amino acid residue(s) is/are deficient and/or substituted and/or added in an amino acid sequence represented by SEQ ID NO: 3 or 4;

(14) A recombinant vector containing the gene or the DNA mentioned in any of the above (9) to (12);

(15) The recombinant vector according to the above (9), wherein promoter and/or terminator are/is placed adjacent to the gene or the DNA mentioned in any of the above (10) to (13);

(16) The recombinant vector according to the above (15), wherein the promoter is a promoter which shows constitutive expression;

(17) The recombinant vector according to the above (15) or (16), wherein the promoter is a promoter of glyceraldehyde-3-phosphate dehydrogenase gene;

(18) A transformant containing the gene or the DNA or the recombinant vector mentioned in any of the above (10) to (17);

(19) The transformant according to the above (18), wherein the transformant belongs to yeast of genus *Saccharomyces*;

(20) A polypeptide encoded by the gene or the DNA mentioned in any of the above (10) to (13) or a polypeptide having an amino acid sequence in which one to several amino acid residue(s) is/are deficient and/or substituted and/or added in an amino acid sequence in the said polypeptide;

(21) A polypeptide having an amino acid sequence represented by SEQ ID NO: 3 or 4 or a polypeptide having an amino acid sequence in which one to several amino acid residue(s) is/are deficient and/or substituted and/or added in the amino acid sequence represented by SEQ ID NO: 3 or 4;

(22) A method for the production of an alcohol or an alcoholic beverage, characterized in that, the transformant mentioned in the above (18) or (19) is used;

(23) A breeding method of yeast which is suitable for the production of an alcohol or an alcoholic beverage, characterized in that, expression of the gene mentioned in the above (10) or (11) or gene on the DNA mentioned in the above (12) or (13) is controlled;

(24) The breeding method according to the above (23), wherein the yeast belongs to the genus *Saccharomyces*;

(25) Yeast obtained by the breeding method according to the above (23) or (24);

(26) A method for the production of an alcohol or an alcoholic beverage using the yeast mentioned in the above (25);

(27) An alcohol or an alcoholic beverage which is produced using the method for the production of an alcohol or an alcoholic beverage according to the above (26);

(28) A DNA array, in which one or more of oligonucleotides comprising the following DNA sequence or its complementary DNA sequence is adhered to a solid support;

DNA sequence (1) having 10 to 30 nucleotides existing in an open reading frame of the whole genome sequence of an industrial yeast and (2) not existing in the region other than the region of said 10 to 30 nucleotides sequence in the whole genome sequence;

(29) A DNA array, in which one or more of oligonucleotides hybridizing in a stringent condition to the oligonucleotides defined in the above (28) is/are adhered to a solid support;

(30) A DNA array, in which one or more of oligonuclaeotides comprising the following DNA sequence or its complementarty DNA sequence is adhered to a solid support;

DNA sequence (1) having 10 to 30 nucleotides existing in a non-coding region of the whole genome sequence of an industrial yeast and (2) not existing in the region other than the region of said 10 to 30 nucleotides sequence in the whole genome sequence;

(31) A DNA array, in which one or more of oligonucleotides hybridizing in a stringent condition to the oligonucleotides defined in the above (30) is/are adhered to a solid support; and

(32) A DNA array, in which oligonucleotides selected from two or more groups of the following 4 groups consisting of one or more of oligonucleotides defined in the above (28), one or more of oligonucleotides defined in the above (29), one or more of oligonucleotides defined in the above (30), and one or more of oligonucleotides defined in the above (31) are adhered to a solid support.

BRIEF DESCRIPTION OF THE DRAWING

FIG. 1 shows total chromosome structures of bottom fermenting yeast. A white bar represents an Sc type chromosome while a black bar represents a non-Sc type chromosome. An ellipse represents a centromere. Roman numerals show chromosome numbers for the corresponding *S. cerevisiae*. In a drawing which shows a non-Sc chromosome, a part marked out in black shows that ligation takes place at the region. For example, in nonScII-nonScIV, it is shown that nonScII and nonScIV are ligated at the part marked out in black (300 kb)).

FIG. 7 shows the fermentation profiles of SSU1 disruptants and parental strain (BH96) . a) shows yeast growth (OD 600), b) shows the change of apparent extract (w/w %) and c) shows sulfite concentration (ppm).

FIG. 8 shows the fermentation profiles of SSU1 overexpressed strains and parental strain (BH225) . a) shows yeast growth (OD 600), b) shows the change of apparent extract (w/w %) and c) shows sulfite concentration (ppm).

FIG. 10 shows DNA sequences of ScSSU1 (FIG. 10A, SEQ ID NO: 33) and non-ScSSU1 (FIG. 10B, SEQ ID NO: 1).

FIG. 11 shows DNA sequences of ScMET4 (SEQ ID NO: 34) and non-ScMET4 (SEQ ID NO: 2).

FIG. 12 shows the fermentation profiles of strain 34/70. a) shows yeast growth (OD 600) and b) shows the change of apparent extract (w/w %).

DETAILED DESCRIPTION OF THE INVENTION

Figure 2:
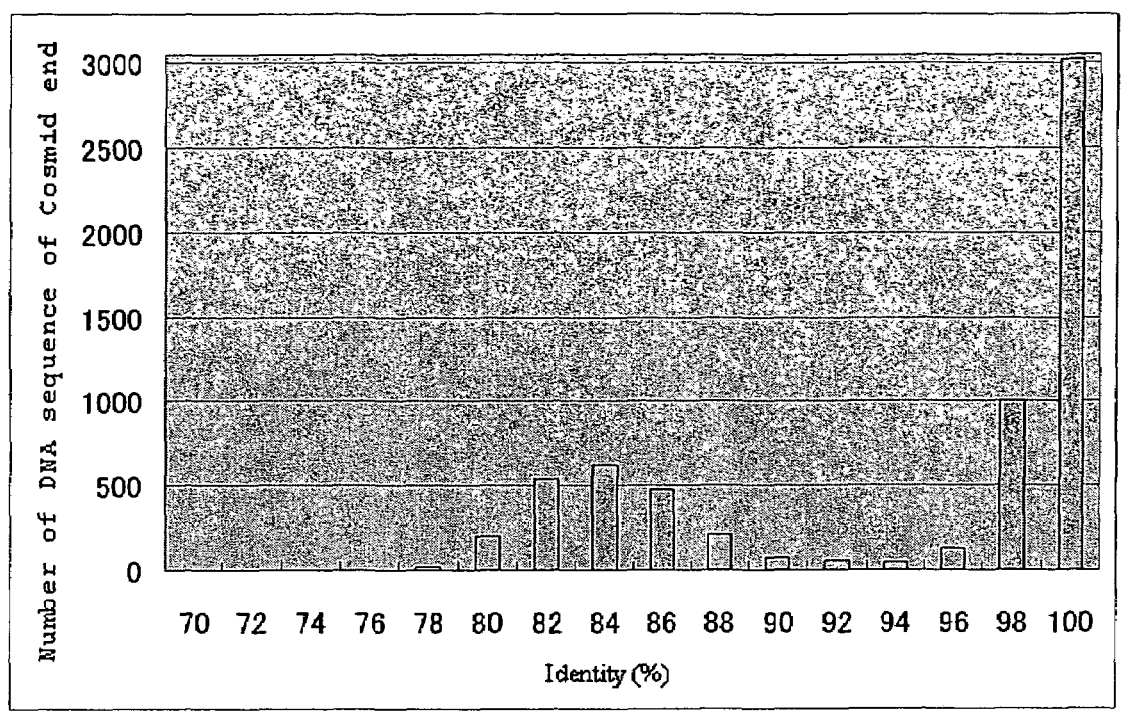
FIG. 2 shows a distribution of identify of the DNA sequence at both ends of 3648 cosmids prepared from the genomic DNA of strain 34/70 with the genome sequence of *S. cerevisiae*. The X-axis shows the identity to *S. cerevisiae* and, for example, 84% on the X-axis shows an identity of more than 82% and not more than 84%. The Y-axis shows the numbers of cosmid end sequences showing the identity.

An object of the present invention is to provide a method for the selection of gene participating in the desired brewing character in such a manner that a database compiling the data of the whole genome sequence of industrial yeast, particularly of a brewing yeast used for alcoholic beverages such as beer is prepared; gene participating in a brewing character that the brewing yeast specifically possesses is selected from the database; and functional analysis of the gene is carried out by disruption or overexpression, and to provide a DNA array (in which oligonucleotide(s) selected based on the database compiling the data of the whole genome sequences of an industrial yeast or, particularly, of a brewing yeast (is/are adhered on a solid plate). Another object is to provide a method for breeding of yeast achieving the brewing character which the gene participates in, and also a method for the production of an alcohol or an alcoholic beverage in which productivity and quality are improved using the yeast. Still another object is to provide a gene which is specific to the brewing yeast and a peptide encoded by the gene.

Means for achieving the above objects is a screening method for genes participating in increase in productivity and/or improvement in flavor in the production of an alcohol or an alcoholic beverage, characterized in that, (A) the whole genome sequence of industrial yeast is analyzed, (B) the genome sequence is compared with the whole genome sequence of S. cerevisiae, (C) gene of the industrial yeast encoding an amino acid sequence having 70 to 97% identity to an amino acid sequence encoded by the gene of S. cerevisiae is selected and (D) functional analysis of the gene is carried out, whereby the character which is given to the yeast by the gene is identified.

With regard to the industrial yeast in the present invention, brewing yeast for beer, wine, sake, etc. and yeasts used for the production of fuel alcohols are exemplified. To be more specific, yeast of genus Saccharomyces, etc. may be listed, and in the present invention beer yeasts such as Saccharomyces pastorianus Weihenstephan 34/70, BH 84, NBRC 1951, NBRC 1952, NBRC 1953, NBRC 1954, etc. may be used. It is also possible to use whisky yeasts such as S. cerevisiae NCYC 90, etc., wine yeasts such as Kyokai wine yeast No. 1, No. 3, No. 4, etc., sake yeasts such as Kyokai sake yeast No. 7, No. 9, etc. and the like.

The screening method for genes in accordance with the present invention is characterized in that (A) the whole genome sequence of industrial yeast, particularly bottom fermenting yeast which is one of the brewing yeasts, is analyzed, (B) the genomic DNA sequence is compared with the whole genome sequence of S. cerevisiae, (C) gene of the bottom fermenting yeast encoding an amino acid sequence which has 70 to 97% identity to an amino acid sequence encoded by the gene of S. cerevisiae is selected and further (D) functional analysis of that selected gene is carried out, whereby the brewing character given to the yeast by the gene is identified.

It is also possible to breed yeast having an excellent brewing character when the gene obtained by the screening method of the present invention is used for carrying out an expression control in such a way that the gene is overexpressed in the yeast, and/or the gene is disrupted. Accordingly, the gene which is obtained by a screening method of the present invention, peptide which is encoded by the gene, a breeding method of an industrial yeast using the gene, yeast which is obtained by the breeding method, and a method for the production of an alcohol or an alcoholic beverage using the yeast are also within a scope of the present invention.

(A) Determination of the Whole Genome Sequence of Industrial yeast

Determination of the whole genome sequence of an industrial yeast includes the steps of (a) genomic DNA is prepared from yeast, (b) shotgun library and (c) cosmid library are prepared from those genomic DNA, (d) DNA fragments to be used for determination of DNA sequence are prepared from those library clones, (e) DNA sequence of the library DNA fragments is determined by a sequence reaction and (f) the sequences of those DNA fragments are assembled to reconstruct the whole genome DNA sequence.

There is no particular limitation for the methods used for (a) to (f) and the method may be conducted according to the known means, while preferred method for each of them is mentioned below.

(a) Preparation such as extraction, purification, etc. of the genomic DNA is preferably carried out in accordance with the known methods, for example, in "Yeast, a practical approach (IRL Press, 6.2.1, p. 228)" and "Seibutuka-gakujikkennhou, No. 39, Experiments in Yeast Molecular Genetics (edited by Yasuharu Oshima, Gakkai Shuppan Center, pages 84 to 85, 1996)". The specific examples of the preferred method for the preparation of DNA are mentioned below.

Yeast cells for the preparation of genomic DNA are cultured by a common method. With regard to a medium, any of natural and synthetic media may be used so far as the medium contains carbon source, nitrogen source, inorganic salt, etc. which are able to be metabolized by the yeast, whereby cultivation of the microorganism can be efficiently carried out. For example, YPD medium (2% (w/w) glucose, 1% (w/w) yeast extract and 2% (w/w) polypeptone) may be used. With regard to a method of incubation, incubation by shaking at about 25 to 35° C. through the night is recommended.

After the cultivation, cells are recovered from the culture medium by centrifugation. The resulting cell pellet is washed with a washing solution. Example of the washing solution is buffer A (50 mM sodium phosphate, 25 mM EDTA and 1% (v/v) β-mercaptoethanol; pH 7.5), etc. Preparation of the genomic DNA from the washed cells may be carried out according to a common preparation method of genomic DNA where cell walls are lysed using Zymolyase and SDS; protein, etc. are removed using a phenol and phenol/chloroform solution; and genomic DNA is precipitated using ethanol or the like. To be more specific, the following method may be exemplified.

Cultivated cells are washed and resuspended in buffer A, then about 5 to 10 mg of Zymolyase 100T (Seikagaku Kogyo) are added and the mixture is gently shaken at about 25 to 40° C. for about 30 minutes to 2 hours. After the shaking, buffer containing SDS such as buffer B (0.2 M Tris-HCl, 80 mM EDTA and 1% SDS; pH 9.5) is added thereto and the mixture is allowed to stand at about 60 to 70° C. for about 30 minutes to lyse the cells. After that, the cell lysate is cooled on ice, mixed with 5 M potassium acetate and allowed to stand on ice for about 60 minutes further. The resulting solution is centrifuged (for example, at 5,000 g for 10 minutes at 15° C.) to take supernatant. The same volume of ethanol is added to the supernatant to precipitate DNA and the mixture is immediately centrifuged (for example, at 5,000 g for 10 minutes at 15° C.) to obtain DNA. The resulting precipitate is washed with 70% (v/v) ethanol, subjected to natural drying and dissolved in a solution such as TE buffer (10 mM Tris-HCl and 1 mM EDTA; pH 8.0) to give a crude genomic DNA solution. Cesium chloride and bisbenzimide are added to and dissolved in the crude genomic DNA solution, the mixed solution is subjected to an ultracentrifugal separation (for example, at 100,000 g for 17 hours at 25° C.), irradiation with UV light is conducted so that the DNA bands are visualized and the lower band is recovered. Bisbenzimide is removed by extracting the recovered DNA solution with isopropanol which is saturated with cesium chloride solution, then 4-fold by volume of 0.3 M sodium acetate are added to the recovered aqueous layer followed by mixing and the DNA is precipitated by ethanol and recovered by centrifugation. The recovered DNA is treated with RNase and extracted with phenol/chloroform and DNA is purified from the recovered aqueous layer by precipitation with ethanol again. The precipitate recovered by centrifugation is washed with 70% (v/v) ethanol, subjected to natural drying and dissolved in a TE buffer to prepare the genomic DNA solution.

(b) Preparation of a Shotgun Library

As to a method for the preparation of a genomic DNA library using the genomic DNA of yeast prepared in the above (a), a method mentioned in "Molecular Cloning, A Laboratory Manual, Third Edition (2001)" (hereinafter, abbreviated as "Molecular Cloning, Third Edition") may be used and, with regard to a method for the preparation of a shotgun library which is particularly suitable for the determination of the whole genome sequence, the following method may be exemplified.

A TE buffer is added to the genomic DNA prepared in (a) and the genomic DNA is fragmented using Hydroshear (manufactured by GeneMachines) or the like. Terminal of the genome fragment is blunted using a DNA Blunting Kit (manufactured by Takara Shuzo) or the like, and fractionated by means of an agarose gel electrophoresis. Then, genome fragments of about 1.5 to 2.5 kb are excised from the gel and a buffer for the elution of DNA such as an MG-elution buffer (0.5 mol/L ammonium acetate, 10 mmol/L magnesium acetate, 1 mmol/L EDTA and 0.1% SDS) or the like is added to the gel followed by shaking at about 25 to 40° C. through the night to elute DNA. The DNA eluate is treated with phenol/chloroform and precipitated with ethanol to give a genomic library insert. All of the above-mentioned insert and an appropriate vector such as pUC 18 SmaI/BAP (manufactured by Amersham Biosciences) are subjected to ligation using T4 ligase (manufactured by Takara Shuzo) at about 10 to 20° C. for about 20 to 50 hours. The ligation reaction product is precipitated with ethanol and the resulting recombinant vector DNA is dissolved in an appropriate amount of TE buffer. By means of electroporation or the like, the recombinant vector DNA is transformed to *Escherichia coli* such as an Electro Cell DH5α strain (manufactured by Takara Shuzo). It is recommended that the electroporation is carried out under the condition mentioned in the attached experimental manual.

The transformants into which recombinant vector containing the genomic DNA fragments is inserted are selected on an appropriate selective medium. For example, when pUC 18 SmaI/BAP is used as a vector, the transformants form white colonies on an LB plate medium (an LB medium (10 g/L of bactotryptone, 5 g/L of yeast extract and 10 g/L of sodium chloride; pH 7.0) which contains 1.6% of agar) containing about 0.01 to 0.1 mg/mL of ampicillin, about 0.1 mg/mL of X-gal and about 1 mmol/L of isopropyl-β-D-thiogalactopyranoside (IPTG) upon incubation through the night at about 30 to 37° C. and, therefore, the selection is easy. The transformants are cultured in LB medium containing about 0.1 mg/mL of ampicillin through the night at about 30 to 37° C. using a 384-well titer plate, a 50% aqueous solution of glycerol in the same volume as the LB is added thereto and the mixture is stirred to give a glycerol stock. Usually, the glycerol stock can be preserved at about −80° C.

(c) Preparation of a Cosmid Library

The genomic DNA prepared in (a) is subjected to a partial digestion using an appropriate restriction enzyme such as Sau3AI (manufactured by Takara Shuzo). It is possible to insert the DNA fragment digested by Sau3AI into a BamHI site of a cosmid vector such as Super CosI vector (manufactured by Stratagene). The treatment with the restriction enzyme and the ligation may be carried out according to the protocol attached thereto. The ligated product obtained by such a method is subjected to a packaging using, for example, Gigapack III Gold (manufactured by Stratagene), and according to the manual for the experimental procedure attached thereto, it is introduced into *Escherichia coli* such as an XL1-Blue MR strain (manufactured by Stratagene). That is spread on an LB plate medium containing ampicillin and incubated through the night at about 30 to 37° C. to get transformants. The resultant transformants are cultured in LB medium containing about 0.1 mg/mL of ampicillin through the night at about 30 to 37° C. using a 96-well titer plate, a 50% aqueous solution of glycerol in the same volume as the LB is added thereto and the mixture is stirred to give a glycerol stock. Usually, the glycerol stock can be preserved at about −80° C.

(d) Preparation of DNA Fragment for Determination of DNA Sequence

The whole genome sequence of brewing yeast can be determined mainly using the whole genome shotgun method. The DNA fragment of which DNA sequence is determined can be prepared by a PCR using the shotgun library prepared in the above (b). To be specific, clone of the genome shotgun library is inoculated using a replicator (manufactured by Gene Solution) to a 384-well titer plate where about 50 µl each of an ampicillin-containing LB medium is placed to each well and cultured without shaking through the night at about 30 to 37° C. The culture is transferred using a replicator (manufactured by Gene Solution) or the like to a 384-well reaction plate (manufactured by AB Gene) where about 10 µl each of a reaction solution for PCR (TaKaRa Ex Taq manufactured by Takara Shuzo) is placed, and PCR is carried out according to a protocol by Makino, et al. (DNA Research, volume 5, pages 1 to 9 (1998)) or the like using a GeneAmp PCR System 9700 (manufactured by Applied Biosystems) or the like, whereupon amplification of the inserted fragment is carried out.

Excessive primer and nucleotide are removed using a kit for the purification of PCR products (manufactured by Amersham Bioscience), etc. and a sequence reaction is carried out using the sample as a template.

Cosmid DNA from the cosmid library of (c) can be prepared by the following method. That is, clone derived from cosmid library is inoculated to each well of a 96-well plate where about 1.0 mL each of an ampicillin-containing appropriate medium such as a 2×YT medium (1.6% bactotryptone, 1% yeast extract and 0.5% sodium chloride; pH 7.0) is placed and cultured with shaking through the night at about 30 to 37° C. Cosmid DNA from the said culture can be prepared using KURABO PI-1100 AUTOMATIC DNA ISOLATION SYSTEM (manufactured by KURABO) according to a manual of KURABO or the like, and they can be used as templates for sequencing reaction.

(e) Sequencing Reaction

A Sequencing reaction can be carried out using a commercially available sequence kit, etc. Preferred examples of the present invention are shown below.

A sequence reaction mixture can be prepared as follows. The PCR product or cosmid DNA prepared in the above (d) is mixed with about 2 µl of DYEnamic ET Terminator Sequencing Kit (manufactured by Amersham Bioscience) and appropriate primers to give about 8 µl of reaction mixture. An M13 forward (M13-21) primer and an M13 reverse (M13RV) primer (manufactured by Takara Bio), etc. are used for the sequence reaction of a PCR product derived from shotgun DNA, while a forward primer such as SS-cos F.1 (SEQ ID NO: 7) and a reverse primer such as SS-cos R.1 (SEQ ID NO: 8), etc. are used for cosmid DNA. Amounts of the primer and the DNA fragment are about 1 to 4 pmole and about 50 to 200 ng, respectively.

A dye terminator sequence reaction of about 50 to 70 cycles can be carried out using the reaction solution and GeneAmp PCR System 9700 (manufactured by Applied Biosciences). When a commercially available kit such as DYEnamic ET Terminator Sequencing Kit is used, a cycle parameter follows a manual attached thereto. Purification of the sample is carried out according to the manual of Millipore using MultiScreen HV plate (manufactured by Millipore), etc. The purified reaction product is precipitated with ethanol and the resulting precipitate is dried and stored in a dark place of about 4° C. The dried product is analyzed using commercially available sequencer and analyzer such as MegaBACE 1000 Sequencing System (manufactured by Amersham Bioscience) and ABI PRISM 3700 DNA Analyzer (manufactured by Applied Biosystems), etc. according to the manuals attached thereto.

(f) Reconstruction of Genomic Sequence by Means of Assembly (A Process Whereby the Order of Multiple Sequenced DNA Fragments is Determined)

Reconstruction of genomic DNA can be carried out from sequence information of DNA fragments obtained in the above (4). All operations of the reconstruction of genomic DNA sequence can be carried out on an UNIX® platform. Base call can be conducted by a software such as phred (The University of Washington) or the like, masking of vector sequence can be carried out by a software such as Cross Match (The University of Washington) or the like and assembly can be carried out by a software such as Phrap (The University of Washington) or the like. Contig obtained as a result of assembly can be analyzed using a graphical editor such as consed, a graphical editor (The University of Washington) or the like. A series of works from base call to assembly can be carried out en bloc utilizing phredPhrap, a script attached to the consed.

(B) Comparison of the Whole Genome Sequence of Brewing Yeast with that of *S. cerevisiae*

Comparison of the whole genome sequence obtained in (A) with that of *S. cerevisiae* includes (g) Preparation of a comparative database compiling the comparison data of each of DNA sequences of both ends of cosmid and shotgun clone and contig with *S. cerevisiae* genome sequence, and mapping of them on *S. cerevisiae* genome sequence.

(g) Preparation of a comparative database compiling the comparison data of each of DNA sequences of both ends of cosmid and shotgun clone and a DNA sequence of contig with genomic DNA sequence of *S. cerevisiae*, and mapping of them on *S. cerevisiae* genome sequence.

Widely used industrial yeast such as bottom fermenting yeast (*S. pastorianus*) has been regarded as a natural hybrid of *S. cerevisiae* and its closely related species (such as *S. bayanus*) "Int. J. Syst. Bacteriol. volume 35, pages 508-511 (1985)". In view of the above, DNA sequences of the both ends of cosmid clone prepared in (e) are subjected to a homology searching against *S. cerevisiae* genome sequence by a homology searching algorithm, whereupon the homologous region and the identity of each DNA sequence to *S. cerevisiae* genome sequence can be determined, thus database can be prepared. An example of identity percentages distribution graph of cosmid DNA sequence corresponding to *S. cerevisiae* genome DNA sequence is shown in FIG. 2. The DNA sequence of cosmid is roughly classified into a DNA sequence group showing more than 94% identity to *S. cerevisiae* genome sequence and a DNA sequence group showing around 84% identity thereto. Accordingly, a DNA sequence showing more than 94% identity is named an Sc-type DNA sequence derived from *S. cerevisiae* while a DNA sequence showing around 84% identity is named a non-Sc-type DNA sequence derived from a closely-related species of *S. cerevisiae* and, gene with the Sc type DNA sequence or the non-Sc type DNA sequence is named Sc type gene or non-Sc type gene, respectively.

Similarly, a comparative database of the DNA sequence of both ends of shotgun clone prepared in (e) with genomic DNA sequence of *S. cerevisiae* is prepared. On the basis of the information obtained from the prepared comparative database, a mapping of cosmid clone and shotgun clone on *S. cerevisiae* genome sequence is carried out (refer, for example, to FIG. 3). A comparative database of the DNA sequence of the contig prepared in (f) with *S. cerevisiae* genome sequence is also prepared and mapping is carried out. Although the mapping technique is nearly the same as that mentioned above, when contigs linked by paired forward-reverse DNA sequence from the same cosmid and shotgun clone, those contigs are linked (refer, for example, to FIG. 4).

(C) Selection of the Gene of Bottom Fermentation Yeast Encoding an Amino Acid Sequence Having 70 to 97% Identity to an Amino Acid sequence encoded by the gene of *S. cerevisiae*

A stage for the selection of the gene of bottom fermenting yeast encoding an amino acid sequence having 70 to 97% identity to an amino acid sequence encoded by the gene of *S. cerevisiae* includes (h) a process of identification of ORF (open reading frame) and assignment of function.

(h) Identification of ORF and Assignment of its Function

Identification of ORF in the DNA sequence assembled in (f) is carried out. Preferred examples are specifically mentioned below. With regard to a certain length DNA sequence (such as not less than 150 base) embraced by initiation codon and termination codon, there can be carried out identification of ORF existing in a DNA sequence assembled in (f) using a program, such as ORF finder (Retrieved from Internet: URL:http://www.ncbi.nih.gov/gorf/gorf.html>) or the like for the identification of ORF for six kinds of reading frames including complementary sequence.

Assignment of function of protein encoded by the identified ORF can be carried out using a homology searching such as BLAST (Retrieved from Internet: <URL:http://www.ncbi.nlm.nih.gov/BLAST>) the like to an amino acid sequence of ORF of *S. cerevisiae* that has been registered and published in the *Saccharomyces* Genome Database (Retrieved from Internet: <URL:http://genome-www.standford.edu/*Saccharomyces*/>).

On the other hand, it is possible to analyze the chromosomal structure of a brewing yeast by DNA microarray-based comparative genomic hybridization and PCR.

Yeast genomic DNA is prepared using a Quiagen Genomic Tip 100/G (#10243) and Qiagen Genomic DNA Buffer Set (#19060) according to the manual attached to the kit. The DNA (10 μg) is digested with DNase I (manufactured by Invitrogen) according to a method of Winzeler, et al. (Science, volume 281, pages 1194-1197 (1998)), biotinylated using a terminal transferase (manufactured by Roche) and hybridized to a DNA microarray (Affymetrix Gene Chip Yeast Genome S98 Array). Hybridization and detection of the signal intensity of microarray are carried out using a Gene Chip Analysis Basic System and analysis software (Microarray Suite 5.0) manufactured by Affymetrix.

The signal of each probe hybridized with the DNA of brewing yeast is normalized to that of the haploid laboratory yeast strain S288C using an analysis software (Microarray Suite 5.0) and shown as signal log ratio ($2^n$). Signal log ratios were lined following genes order in each chromosome using a spreadsheet program (Microsoft Excel 2000) and the signal log ratios are shown in bar graphs (refer, for example, to FIG. 5). The non-Sc type genes do not hybridize to the *S. cerevisiae* array, therefore, the Sc type gene dosage affect the signal log ratio and the points where the signal log ratios show vigorous changes are considered to be translocation sites between Sc type and non-Sc type chromosome.

The chimera chromosome structure can be confirmed by PCR where a genomic DNA derived from brewing yeast is used as a template and Sc type and non-Sc type shotgun sequences is used as primers.

PCR is carried out using a Takara PCR Thermal Cycler SP according to the attached manual using a Takara LA Taq™ and a buffer attached thereto.

As a result of the PCR, it is confirmed by 0.8% agarose electrophoresis that a certain length of DNA fragment is amplified from the brewing yeast. When a genomic DNA of *S. cerevisiae* which is a laboratory strain is used as a template for the PCR, no amplification of DNA fragment is detected. If DNA sequences of the both ends of the DNA fragment amplified from the brewing yeast are further confirmed, it is consistent with the genome sequences determined by a shotgun method and it can be confirmed that, within such region, translocation between Sc type and non-Sc type chromosome takes place, whereupon a chimera chromosome is formed.

(D) Functional Analysis of Genes Derived from the Bottom Fermenting Yeast

The stage of functional analysis of gene includes (i) selection of the gene, (i') cloning of the gene, (j) functional analysis of the gene by disruption and (k) functional analysis of the gene by overexpression.

(i) Selecting of the Gene

There is no particular limitation for the methods used for the selection of gene(s) for functional analysis, while preferred methods are, for example, a method using the assignment of the function obtained in the above (h) and a method using a DNA microarray as described below. The method using DNA microarray is, for example, gene expression analysis to identify genes, which show characteristic expression profile under some conditions, or comparative genomic hybridization to identify genes, which have different copy numbers or different DNA sequences, by detecting deference of signal intensities of probes.

(i') Cloning of the Gene

Genes selected in the above (i) can be obtained from the bottom fermentaing yeast according to a common method mentioned, for example, in Molecular Cloning, Third Edition. That is, oligonucleotides having sequences adjacent to the gene are synthesized and a common PCR cloning method is carried out using a genomic DNA prepared from a bottom fermenting yeast as a template, whereupon the selected gene can be isolated and obtained. With regard to DNA sequences obtained as such, for example, by SEQ ID NO: 1 or NO: 2 may be listed.

When the gene is named, for example, a gene ①, the gene ① or primer for amplifying the gene ① by a PCR method may be also synthesized using a polynucleotide synthesizer on the basis of the above-mentioned sequence information. In addition, gene ① means not only a DNA fragment having the same DNA sequence as gene ① but also a DNA fragment hybridizing to the above gene under stringent condition. The DNA fragment which hybridizes under stringent condition means a DNA fragment which is obtained by a colony hybridization method, a plaque hybridization method, a southern blot hybridization method or the like, using the DNA fragment containing the sequence of the gene ① identified in the above as a probe. To be specific, a DNA fragment which shows at least not less than 60% identity to a DNA sequence of the gene ①, preferably not less than 80% identity thereto and, more preferably, not less than 95% identity thereto may be listed. The hybridization may be carried out according to a method mentioned in "Molecular Cloning, Third Edition", "Current Protocols in Molecular Biology, John Wiley & Sons (1987-1997) (hereinafter, abbreviated as Current Protocols in Molecular Biology), "DNA Cloning 1: Core Techniques, A Practical Approach, Second Edition, Oxford University (1995)", and the like.

To be more specific, shotgun clone containing full-length of the above-mentioned gene ① can be retrieved using the comparative database obtained in (g) and, on the basis of homology and positional information, etc. When there is no clone containing full-length of the gene in the shotgun library, a DNA fragment encoding the full length of the gene is prepared by a PCR method. For example, a DNA fragment containing the above-mentioned gene is obtained using synthetic DNA primer pair represented by SEQ ID NO: 13 and SEQ ID NO: 14, etc. Similarly, PCR is carried out using a primer pair designed on the basis of the published information of SGD and using genomic DNA of S. cerevisiae or bottom fermenting yeast as a template, whereupon the full length of the Sc type gene corresponding to the non-Sc type gene is prepared. For example, using synthetic oligonucleotides of SEQ ID NO: 15 and NO: 16 as the primer pair, the DNA fragment containing the Sc type gene can be obtained.

Sc or non-Sc type DNA fragment prepared as mentioned above is inserted into, for example, pCR 2.1-TOPO vector attached to a TA cloning kit (Invitrogen) using a TA cloning kit or the like, whereupon a recombinant vector TOPO/Sc gene and TOPO/non-Sc gene containing the DNA fragment having the Sc and the non-Sc type gene, respectively, are able to be prepared. DNA sequences of the Sc and non-Sc type DNA fragments can be confirmed by a Sanger's method "F. Sanger, Science, volume 214, page 1215, 1981".

(j) Functional Analysis of the Gene by Disruption

According to a method of the document "Goldstein, et al., Yeast, volume 15, page 1541, (1999)", it is possible to prepare a DNA fragment for gene disruption by PCR where a plasmid containing a drug-resistance gene (such as pFA 6a (G418$^r$), pAG 25 (nat1)) is used as a template. As a primer pair for the PCR, non-ScSSU1_for (SEQ ID NO: 17)/non-ScSSU1_rv (SEQ ID NO: 18) or the like is used for the non-ScSSU1 disruption, while for the Sc SSU1 disruprion, ScSSU1_for (SEQ ID NO: 19)/ScSSU1_rv (SEQ ID NO: 20) or the like is used. For the non-Sc type gene disruption, it is also possible to use a plasmid such as pPGAPAUR (AUR1-C) and a primer pair such as non-ScSSU1_for +pGAPAUR (SEQ ID NO: 21)/non-ScSSU1_rv+AURI-C (SEQ ID NO: 22).

A bottom fermenting yeast is transformed with the DNA fragment for the gene disruption prepared by the above-mentioned method. The transformation may follow a method mentioned in the Japanese Patent Laid-Open Gazette No. 07/303,475. Further, the concentration of the drug for the selection of transformants may be appropriately determined by investigating the sensitivity of the yeast used as a host.

With regard to the transformant prepared here, it is confirmed that each of the drug-resistance genes is introduced and the said gene is disrupted correctly using a Southern analysis. To be specific, the genomic DNA extracted from the parental strain and the transformant are firstly digested by an appropriate restriction enzyme to distinguish Sc and non-Sc type gene (for example, at 37° C. for 18 hours), then fractionated with 1.5% agarose gel electrophoresis and transferred to a membrane. After that, they are hybridized to a probe specific to an Sc-type or a non-Sc type gene for example at 55° C. for 18 hours according to a protocol of Alkphos Direct Labelling Reagents (Amersham) and a signal is detected by CDP-Star.

The function of the gene obtained in (i') can be confirmed by fermentation test using a parental strain and SSU1 disruptants prepared in the above (j) and comparison of their fermentation character. Fermentation test can be carried out, for example, using wort under the following condition.

Original extract: about 10 to 15%
Fermentation scale: 1 to 3 liters
Dissolved oxygen concentration: about 8 to 10 ppm
Fermentation temperature: about 15° C.
Pitching rate: about 4 to 6 g of wet yeast cells/L Wort is periodically sampled and monitored in cell growth (OD 600), apparent extract, the concentration of the substance participating in the function of the gene obtained in (i'), etc. is analyzed. For example, when the function of the gene obtained in (i') participates in discharge of sulfite, the sulfite concentration in the wort during the fermentation is analyzed. Quantitative analysis of sulfite is carried out in such a manner that sulfite is captured in a hydrogen peroxide solution by means of distillation under an acidic condition and subjected to titration with an alkali (Revised Method for BCOJ Beer Analysis by the Brewing Society of Japan).

(k) Functional Analysis of the Gene by Overexpression

A DNA fragment containing the full-length of the non-Sc type gene is excised by an appropriate restriction enzyme from the plasmid TOPO/non-Sc gene prepared in (i'). It is inserted into a cloning site of a vector for gene expression such as pNI-NUT to construct a vector (pYI-non-Sc type gene) for overexpression of the non-Sc type gene. The vector pNI-NUT contains URA3 as a homologous recombination site and nourseothricin-resistance gene (nat1) and ampicillin-resistance gene (Amp$^r$) as selective markers. On the other hand, a vector for overexpression of the Sc type gene (pNI-Sc type gene) has a structure where the above-mentioned pYI-non-Sc type gene is substituted by the corresponding Sc type gene. For overexpression of the Sc or non-Sc type gene introduced here, it is preferred to be driven by promoter and terminator of constitutively expressing gene, for example, glyceraldehyde-3-phosphate dehydrogenase gene (TDH3).

A bottom fermenting yeast is transformed using the overexpression vector, which is prepared by the above-mentioned method. The transformation is carried out by the method mentioned in the Japanese Patent Laid-Open Gazette No. 07/303,475 and transformants are selected on an appropriate selective medium. Confirmation of the overexpression may be carried out by RT-PCR method, etc. Extraction of the total RNA may be carried out using an RNeasy Mini Kit (Qiagen) or the like, according to the manual of "for total RNA isolation from yeast" attached to the kit. For example, it is possible to use ScSSU1_for 331 (SEQ ID NO: 23) /ScSSU1_982rv (SEQ ID NO: 24) and non Sc-SSU1_for 329 (SEQ ID NO: 25) /non Sc-SSU1_981rv (SEQ ID NO: 26) as specific primer pairs for the amplification of Sc and non-ScSSU1 gene, respectively. To amplify the constitutively expressed gene, for example PDA1, as an internal standard, PDA1_for 1 (SEQ ID NO: 27)/PDA1_730rv (SEQ ID NO: 28) etc. may be used as a specific primer pair. PCR product is fractionated with 1.2% agarose gel electrophoresis and detected with ethidium bromide staining. The overexpression of the said gene in the transformant is confirmed by comparison of quantity of the PCR products.

The functional analysis of the gene obtained in (i') can be carried out by a fermentation test using the parental strain and the overexpressed strain prepared in the above (k). Fermentation test may be carried out under the condition mentioned in (j).

According to the same method mentioned in (j), the wort is periodically sampled and monitored in the cell growth (OD600), apparent extract and the concentration of the substance participating in the function of the gene obtained in (i').

With regard to the DNA which is obtained by the screening method of the present invention, a DNA containing the DNA sequence of the non-Sc type gene obtained in the above and a DNA which hybridizes to the said DNA under stringent condition may be listed.

The DNA obtained by the screening method of the present invention includes single-stranded and double-stranded DNAs although they are non-limitative. A DNA which hybridizes to the DNA containing a DNA sequence of the non-Sc type gene obtained in the above under stringent condition includes a degenerated mutant of codon of the protein encoded by the said gene. A degenerated mutant means a polynucleotide fragment encoding the same amino acid sequence by degeneration of codon, although in terms of a DNA sequence, it is different from a DNA sequence of the non-Sc type selected by the present invention.

Specific examples thereof are a DNA with a sequence as shown by SEQ ID NO: 1 or 2, a DNA which hybridizes to the said DNA under stringent condition, etc. The DNA which hybridizes under stringent condition means a DNA which is prepared by a colony hybridization method, a plaque hybridization method, a southern blot hybridization method or the like using a DNA fragment with the sequence of the non-Sc type identified hereinabove as a probe.

Hybridization may be carried out according to a method mentioned in "Molecular Cloning, Third Edition", "Current Protocols in Molecular Biology", "DNA Cloning 1: Core Techniques, A Practical Approach, Second Edition, Oxford University (1995)", etc. Specific examples of the hybridizable DNA is a DNA which shows at least not less than 60% identity, preferably a DNA which shows not less than 80% identity and, more preferably, a DNA which shows not less than 95% identity to a DNA sequence as shown in SEQ ID NO: 1 or 2 when calculation is conducted using a parameter of the default setting (initial setting) by a software for homology searching such as FASTA, BLAST, Smith-Waterman "Meth. Enzym., volume 164, page 765 (1988)", etc.

An example of the DNA obtained by the screening method of the present invention is a DNA encoding a polypeptide comprising an amino acid sequence as shown by SEQ ID NO: 3 or 4 or a DNA which hybridizes to the said DNA under stringent condition.

An example of the polypeptide which is encoded by the DNA obtained by the screening method of the present invention is a polypeptide encoded by the DNA containing the DNA sequence of ORF obtained in the above and a polypeptide encoded by the DNA which is hybridized to the said DNA under stringent condition or a polypeptide comprising an amino acid sequence as shown by SEQ ID NO: 3 or 4.

Further, a polypeptide comprising an amino acid sequence where one or more amino acid residue(s) is/are deficient and/or substituted and/or added in the amino acid sequence of the said polypeptide and has substantially same activity as the activity of the said polypeptide is also included in the present invention. The expression reading "substantially same activity as the activity of the said polypeptide" means the same activity as the activity which is represented by enzymatic activity or the function inherent to the polypeptide before the deficiency, substitution or addition. The said polypeptide can be prepared by a site-specific mutation introduction which is mentioned in "Molecular Cloning, Third Edition", "Current Protocols in Molecular Biology", "Nuc. Acids. Res., volume 10, page 6487 (1982)", "Proc. Natl. Acad. Sic. USA, volume 79, page 6409 (1982)", "Gene, volume 34, page 315 (1985)", "Nuc. Acids. Res., volume 13, page 4431 (1985)", "Proc. Natl. Acad. Sci. USA, volume 82, page 488 (1985)", etc. For example, it is able to be prepared by introducing a site-specific mutation into a DNA encoding a polypeptide comprising an amino acid sequence as shown in SEQ ID NO: 3 or 4. Although there is no particular limitation for the number of the amino acid residue(s) which is/are deficient and/or substituted and/or added, the number is within such an extent that is able to be deficient and/or substituted and/or added by known methods such as the above-mentioned site-specific mutation method and is one to several tens, preferably 1 to 20, more preferably 1 to 10 and, still more preferably, 1 to 5.

The DNA of one or more amino acid residue(s) is/are deficient and/or substituted and/or added in the amino acid sequence of the polypeptide of the present invention means that there is/are one or more deficiency (ies) and/or substitution(s) and/or addition(s) of one or more amino acid residue(s) in any one or more position(s) of the amino acid sequence in the same sequence. Those deficiency (ies) and/or substitution(s) and/or addition(s) may take place at the same time and the substituted or added amino acid residue may be either naturally occurring type or a non-naturally occurring type. Examples of the amino acid residue of a natural type are L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine and L-cysteine, etc.

Examples of the amino acid residue which is able to be substituted each other will be shown below. Amino acid residues in the same group may be substituted each other.

Group A: leucine, isoleucine, norleucine, valine, norvaline, alanine, 2-aminobutanoic acid, methionine, O-methylserine, tert-butylglycine, tert-butylalanine and cyclohexylalanine.

Group B: aspartic acid, glutamic acid, isoaspartic acid, isoglutamic acid, 2-aminoadipic acid and 2-aminosuberic acid.

Group C: asparagine and glutamine.

Group D: lysine, arginine, ornithine, 2,4-diaminobutanoic acid and 2,3-diaminopropionic acid.

Group E: proline, 3-hydroxyproline and 4-hydroxyproline.

Group F: serine, threonine and homoserine.

Group G: phenyl alanine and tyrosine.

For the purpose that the resulting mutated polypeptide has the substantially same activity as the activity of the polypeptide before the mutation, it is preferred that the mutated one has at least 60% or more, usually 80% or more or, particularly, 95% or more of identity to the amino acid sequence of the polypeptide before the mutation when calculation is carried out using a parameter of the default setting (initial setting) by a software for the analysis such as BLAST and FASTA.

It is also possible to produce the polypeptide of the present invention by a chemical synthetic method such as Fmoc method (fluorenylmethyloxycarbonyl method), tBoc method (tert-butyloxycarbonyl method), etc. It is further possible to chemically synthesize by using a peptide synthesizers manufactured by Advanced ChemTech, Perkin-Elmer, Pharmacia, Protein Technology Instrument, Synthecell-Vega, PerSeptive, Shimadzu, etc.

When the method of the present invention is used, it is possible to determine the whole genome sequence of industrial yeast, to identify the useful genes of industrial yeast and to assign the functions of the said genes. There are many cases where the genes in industrial yeast are industrially useful and, when the genes are classified on the basis of the assigned functions, character of the yeast is clarified and precious information for breeding of industrial yeast is able to be obtained. For example, when the industrial yeast is a brewing yeast, then a gene participating in increase in productivity and improvement in flavor in the production of alcoholic beverage is identified and, in case the gene is disadvantageous for the increase of productivity or for the improvement of flavor, the gene expression is suppressed by a gene disruption, an antisense method or an RNAi method (c.f., for example, Non-Patent Document 10), whereupon a yeast which shows an excellent brewing character can be bred. In case the gene is advantageous for the increase of productivity, improvement of flavor, etc., then for example the gene is overexpressed in the yeast, whereupon brewing yeast which shows an excellent brewing character, which is industrially useful, can be bred.

An example where the gene obtained by the screening method of the present invention is used to breed useful yeast is shown as follows.

As already mentioned above, when the sulfite concentration in a product is increased, it is possible to make a product with excellent flavor stability. Therefore, if the gene obtained by the screening method of the present invention contributes to production and efflux of sulfite, it is now possible that a transformant is cultivated and expressed the said gene to make a product with excellent flavor stability as a result of the increase in the concentration of sulfite in the product.

It has been known that a bottom fermenting yeast reduces sulfate ion ($SO_4^{2-}$) taken from outside of the cell to sulfite ion ($SO_3^{2-}$). However, sulfite inhibits glyceroaldehyde-3-phosphate dehydrogenase and reduces the concentration of intracellular ATP, therefore, yeast has a function of discharging sulfite so that excessive sulfite should not be accumulated in the cell. SSU1 is a gene, which has been isolated and shown complement the sulfite-sensitive mutation (c.f., for example, Non-Patent Document 11). SSU1 gene product comprises 485 amino acid residues, and the structural analysis suggests that it is a transporter with 9 to 10 membrane-spanning domains (c.f., for example, Non-Patent Document 12). Further, as a result of experiment using a SSU1 overexpressed strain, it has been already proved that the SSU1 gene product participates in discharge of sulfite (c.f., for example, Non-Patent Document 13).

Bottom fermenting yeast usually has a high production ability of sulfite, while top fermenting yeast rarely produces it. By using a screening method of the present invention, it is possible to select non-ScSSU1 gene which is specific to bottom fermenting yeast in addition to ScSSU1 gene which exists in both top and bottom fermenting yeast. Similarly, in the case of MET14 gene, which encodes a protein participating in the production of sulfite, it is also possible to select a non-ScMET14 which is specific to bottom fermenting yeast. Functions of, for example, non-ScSSU1 and non-ScMET14 greatly participate in a high production ability of sulfite, which is specific to bottom fermenting yeast, and it is effective to intensify those non-ScSSU1 gene, non-ScMET14, etc. in order to breed yeast which shows higher production ability of sulfite.

Breeding methods of yeast where those non-ScSSU1 gene and non-ScMET14 are intensified are specifically mentioned in the Examples.

With regard to yeast used as a host in the introduction of gene selected by the screening method of the present invention, there is no particular limitation so far as it is yeast which is usable for brewing, and any yeast which is widely used as a brewing yeast at present such as beer yeast including BH 84, NBRC 1951, NBRC 1952, NBRC 1953 and NBRC 1954 may be used. Further, whisky yeasts (such as *S. cerevisiae* NCYC 90), wine yeasts (such as wine yeast Kyokai No. 1, No. 3, No. 4, etc.) and sake yeasts (such as sake yeast Kyokai No. 7, No. 9, etc.) may be also used.

With regard to a vector used for the introduction of gene into the above-mentioned host, there is no particular limitation so far as it is a vector which can express gene in the yeast, and any of plasmid of a multicopy (YEp type), a single-copy plasmid (YCp type) and a chromosomal DNA-integrating plasmid (YIp type) may be utilized. An example of a YEp vector is YEp 51 (J. R. Broach, et al., Experimental Manipulation of Gene Expression, Academic Press, New York, 83, 1983), etc. an example of a YCp vector is YCp 50 (M. D. Rose, et al., Gene, volume 60, page 237, 1987), etc.; and an example of a YIp vector is YIp 5 (K. Struhl, et al., Proc. Natl. Acad. Sci. USA, volume 76, page 1035, 1979), etc. Those plasmids are put into the market and are easily available.

The above-mentioned vector may have other sequence for controlling expression of gene in yeast such as, promoter, operator, enhancer, silencer, ribosome binding sequence, terminator, etc. With regard to a promoter and a terminator for a constitutive expression of a gene, there is no particular limitation but any combination may be used so far as it functions in a brewing yeast and is independent from sulfite concentration in the product. As to a promoter for example, it is possible to use a promoter for glyceraldehyde-3-phosphate dehydrogenase (TDH3) gene, a promoter for phosphoglycerate kinase (PGK1) gene, etc. Those promoters have been known, and PGK1 gene, for example, is mentioned in detail in publicly known documents such as M. F. Tuite, et al., EMBO J., volume 1, page 603 (1982) and is easily available.

It is not necessary that the above-mentioned other sequences which regulate the expression of the introduced gene are particularly provided from vector so far as the DNA obtained by the screening method of the present invention includes them. When such other sequences are not contained in the said DNA, it is preferred that other sequences are prepared separately and ligated to the said DNA. Alternatively, even in the case of higher expression level or specific regulation of expression is required, other sequences appropriate for such a purpose are ligated to the said DNA.

A method for the transformation of the above vector to a host may follow known procedures. For example, the following methods may be used; an electroporation method "Meth. Enzym., volume 194, page 182 (1990)", a spheroplast method "Proc. Natl. Acad. Sci. USA, volume 75, page 1929 (1978)", a lithium acetate method "J. Bacteriology, volume 153, page 163 (1983)", a method mentioned in "Proc. Natl. Acad. Sci. USA, volume 75, page 1929 (1978)", etc.

To be more specific, a host is cultivated in a standard yeast nutrient medium (such as YEPD medium "Genetic Engineering, vol. 1, Plenum Press, New York, 117 (1979)", etc.) so that the absorbance at 600 nm becomes 1 to 6. Cells are collected by centrifugation, washed and subjected to a pre-treatment with an alkali metal ion or, preferably, lithium ion in a concentration of about 1M to 2M. After the cells are incubated at about 30° C. for about 60 minutes, they are incubated together with DNA to be introduced (about 1 to 20 μg) at about 30° C. for about 60 minutes. Polyethyleneglycol or, preferably, polyethyleneglycol of about 4,000 daltons is added as the final concentration will be about 20% to 50%. After the incubation is carried out at about 30° C. for about 30 minutes, the cells are subjected to a heating treatment at about 42° C. for about 5 minutes. Preferably, the cell suspension is washed with a standard yeast nutrient medium and placed in a predetermined amount of a fresh standard yeast nutrient medium, then incubated at about 30° C. for about 1 hour. After the incubation, it is spread on an appropriate selective medium plate.

Besides the above, as for a general cloning technique, "Molecular Cloning, Third Edition", "Methods in Yeast Genetics, A Laboratory Manual (Cold Spring Harbor Laboratory Press, Cold Spring Harbor, N.Y.)", etc. were referred to.

With regard to a selective marker used for the transformation, it is not possible to utilize an auxotrophic marker in the case of brewing yeast and, therefore, G 418-resistance gene (G 418$^r$), copper-resistance gene (CUP 1) "M. Marin, et al., Proc. Natl. Acad. Sci. USA, volume 81, page 337, 1984", serulenin-resistance gene (fas2m, PDR 4) ("Atsushi Inogoshi, et al., Seikagaku, volume 64, page 660, 1992", "M. Hussain, et al., Gene, volume 101, page 149, 1991", etc. are applicable.

The brewing yeast bred according to the present invention is not different from a parental strain in terms of growth and fermentation ability of yeast. Accordingly, materials, facilities for the production, production control, etc. may be entirely the same as those in the conventional methods, which is an important aspect of the present invention. However, it goes without saying that, conditions such as fermentation period may be changed on a case-by-case, if desired. For example, when a brewing yeast in which discharging ability of sulfite is intensified and an alcoholic beverage is produced using such yeast, only the content of sulfite in the product changes, and there is no difference from the case where a parental strain is used, in terms of growth and fermentation ability of the yeast. Accordingly, materials, facilities for the production, production control, etc. may be entirely the same as those in the conventional methods, and there is no increase in the cost of production of an alcoholic beverage in which sulfite content increases and of which flavor is improved.

(E) Production of a DNA Array of this Invention

A DNA array of this invention can be produced based on the DNA sequence information of the ORFs obtained in the above (f). Examples include a DNA array comprising a solid support to which at least one of a polynucleotide comprising the DNA sequence obtained above items (f), a polynucleotide which hybridizes with the polynucleotide under stringent conditions, and a polynucleotide comprising 10 to 200 continuous nucleotides in the DNA sequence of the polynucleotide is adhered; and a DNA array comprising a solid support to which at least one of a polynucleotide encoding a polypeptide comprising the amino acid sequence obtained as above (h), a polynucleotide which hybridizes with the polynucleotide under stringent conditions, and a polynucleotide comprising 10-200 continuous bases in the DNA sequence of the polynucleotides, a polynucleotide comprising intergenic DNA sequence between two ORFs deduced from the above (h) is adhered.

DNA arrays of the present invention include substrates known in the art, such as a DNA chip, polynucleotide array and a DNA microarray and a DNA macroarray, or the like, and comprises a solid support and plural polynucleotides of fragments thereof which are adhered to the surface of the solid support. As the polynucleotids or oligonucleotides adhered to the solid support, the polynucleotides or oligonucleotides of the present invention obtained in the above items (f) and (h) can be used. The analysis described below can be efficiently performed by adhering the polynucleotides or oligonucleotids to the solid support at a high density, though a high fixation density is not always necessary. Apparatus for achieving a high density, such as an arrayer robot or the like, is commercially available from Takara Shuzo (GMS417 Arrayer), and the commercially available product can be used. Also, the oligonucleotide of the present invention can be synthesized directly on the solid support by the photolithography method or the like (Nat. Genet. 21, 20-24 (1999)). In this method, a linker having a protective group which can be removed by light irradiation is first adhered to a solid support, such as slide glass or the like. Then, it is irradiated with light through a mask (a photolithograph mask) permeating light exclusively at a definite part of the adhesion part. Next, an oligonucleotide having a protective group which can be removed by light irradiation is added to the part. Thus, a ligation reaction with the nucleotide arises exclusively at the irradiated part. By repeating this procedure, oligonucleotides, each having a desired sequence, different from each other can be synthesized in respective parts. Usually, the oligonucleotides to be synthesized have a length of 10 to 30 nucleotides. There is no particular limitation for the methods used for the production of DNA array and the method may be conducted according to the known means, while preferred method for each of them is mentioned below.

(1) Production of a DNA Array (1)-1 Solid Support

Any materials of which the polynucleotids or fragments can be adhere to the surface can be used as the solid supports for the invention DNA array. There is no particular limitation for the material and shape used for the solid support, while preferred materials are some resinoids, such as polycarbonate, plastics or the like, as a material and a plate-like and film-like as a solid.

(1)-2 Selection a Oligonucleotide

The example of oligonucleotides to be fixed on the plate of a DNA array of this invention are as follows. Based on the DNA sequences of ORFs obtained in the above (h) and/or intergenic DNA seqqeunces deduced from the above (h), unique and complementary probes (PM Probe; Perfect Match Probe) against whole genome sequence of brewing yeast can be designed using a certain method of probe production, such as GeneChip® (Affymetrix) technology or the like. Examples of these probes are (i) an oligonucleotide having 10 to 30 nucleotides existing in an open reading frame of the whole genome sequence of an industrial yeast and not existing in the region other than the region of said 10 to 30 nucleotides sequence in the whole genome sequence, (ii) an oligonucleotide having an DNA sequence complementary to the DNA sequence of oligonucleotide described in (i), (iii) an oligonucleotide hybridizing in a stringent condition to the oligonucleotides described in (i) and (ii). The other examples of these probes are (iv) an oligonucleotide having 10 to 30 nucleotides existing in a non-coding region of the whole genome sequence of an industrial yeast and not existing in the region other than the region of said 10 to 30 nucleotides sequence in the whole genome sequence, (v) an oligonucleotide having an DNA sequence complementary to the DNA sequence of oligonucleotide described in (iv), (vi) an oligonucleotide hybridizing in a stringent condition to the oligonucleotides described in (iv) and (v). Nucleotides number of these oligonucleotides are not limited, but 10 to 30 nucleotides are preferable. 11-50 probes an each locus can be designed with focus on 3' prime side of each locus, as the use of sets of probes for each locus can provide redundancy in the detection and analysis of the data, can mitigate the potentially confounding effects of occasional cross-hybridization, and can make it so all probes do not have to hybridize identically in order to obtain quantitative information. To further increase the sensitivity and specificity of detection, each PM probe can be designed with a closely related mismatch probe (MM probe) that is identical to PM probe with the exception of a mismatched base, i.e. base 13. The preferable length of oligonucleotide which is used in this invention is 26 base, but no particular limitation for the length of oligonucleotide.

(l)-3 Adhering Oligonucleotides to Solid Support

There is no particular limitation for the methods used for adhering oligonucleotides to solid support, and the method may be conducted according to the known means, while preferred method is mentioned below. For example, all of designed PM and MM probes as above ((l)-2) can be adhered to the surface of solid support to produce a DNA array using a certain method, such as GeneChip® technology or the like.

There is no particular limitation for the methods used for analysis using DNA maicroarray, while preferred methods for each of them is mentioned below, i.e., the example of gene expression analysis to identify genes, which show characteristic expression profile under some conditions, classification of industrial yeast, detection of nucleotide polymorphism and selection of genes for functional analysis are mentioned below.

(m) Gene Expression Analysis

Gene expression analysis of brewing yeast can be carried put using the DNA array of this invention produced according to the method described in (l). It is possible to identify the highly inducible or reducible gene(s) according to change of not only medium but also environment using the DNA array. It is also possible to identify the specific gene(s) for lager brewing yeast in brewing using the DNA array. But it is not limited for these examples.

Gene expression analysis includes culturing of a industrial yeast, preparation of mRNA, synthesis of labeled cRNA (or cDNA), hybridization, and data analysis. There is no particular limitation for the methods of gene expression analysis, while preferred methods for each of them is mentioned below.

(m)-1 Culturing a Industrial Yeast in a Various Condition

Industrial yeast can be cultivated under various conditions for any purpose. For example, the cultivation for identification of genes which respond to the change of composition of culture medium can be carried out as mentioned below. Industrial yeast can be grown overnight in a Zinc replete medium, such as LZMM medium+40 µM zinc sulfate at 30° C. with shaking. LZMM medium contains 0.17% yeast nitrogen base w/o amino acids (manufactured by DIFCO), 0.5% ammonium sulfate, 20 mM sodium citrate (pH 4.2), 125 µM MnCl2, 10 µM FeCl2, 2% maltose, 10 mM EDTA (pH 8.0), or the like. Cells are harvested and washed three times with sterile distilled water. An adequate amount of cells, are inoculated to an optical density (OD600) of 0.25, or the like, in 1) zinc depleted medium (LZMM medium) or the like, 2) zinc replete medium (LZMM+40 µM zinc sulfate) or the like, 3) oxidative stress medium (LZMM+40 µM zinc sulfate+2mMH2O2) or the like, 4) carbon starvation medium (deleting maltose from above LZMM+40 µM zinc sulfate) or the like. Cells are grown at 30° C. for 6 hours or the like and harvested for RNA preparation. Cells withdrawn from fermentation tube under beer fermenting condition can be used for the following experiments.

(m)-2 Preparation of mRNA

Preparations of total RNA can be carried out using an RNeasy® Mini Kit (manufactured by QIAGEN) or the like according to a manual. Preparations of Poly (A)+mRNA from total RNA are carried out using an Oligotex Direct mRNA kit (manufactured by QIAGEN) or the like according to a manual. There is no particular limitation for the methods used for preparation of mRNA and the method may be conducted according to the known means.

(m)-3 Synthesis of Labeled cRNA

Synthesis of Labeled cRNA can be carried out using a BioArray HighYield RNA Transcript Labeling Kit (manufactured by Affymetrix) or the like according to a manual. Biotin can be used for labeling. There is no particular limitation for the methods used for syntheses of Labeled cRNA and the method may be conducted according to the known means.

(m)-4 Hybridization

5 µg of Biotin-Labeled cRNA, 1.7 µl of 3 nM Control Oligonucleotide B2 (manufactured by Affymetrix), 5 µl of 20× Eukaryotic Hybridization Controls (manufactured by Affymetrix), 1 µl of 10 mg/ml Herring Sperm DNA (manufactured by Affymetrix), 1 µl of 50 mg/ml Acetylated BSA (manufactured by Affymetrix), 50 µl of 2× Hybridization buffer (manufactured by Affymetrix), and water (manufactured by Affymetrix) to give final volume of 100 µl are mixed and hybridized to the DNA array according to a Technical Mannual of Affymetrix. After 16 hours of hybridization, hybridization cocktail are removed and the DNA array is washed using the a GeneChip® Fludics Station (manufactured by Affymetrix) or the like, and stained with a Streptavidin Phycoerythrin (300 µl of 2× MES Stain Buffer (manufactured by Affymetrix), 24 µl of 50 mg/ml acetylated BSA (manufactured by Affymetrix), 6 µl of 1 mg/ml StreptAvidin-Phycoerythrin (manufactured by Affymetrix), 270 µl of Water (manufactured by Affymetrix)) according to a Technical Mannual of Affymetrix. There is no particular limitation for the methods used for hybridization and the method may be conducted according to the known means.

(m)-5 Data Analysis

Data analysis of the DNA array can be carried out using a commercially available software (for example, a GCOS (GeneChip Operating Software) manufactured by Affymetrix; GeneSpring manufactured by Silicon Genetics; ImaGene manufactured by Takara Shuzo; Array Gauge manufactured by Fuji Photo Film; ImageQuant manufactured by Amersham Pharmacia Biotech, or the like) according to a Technical Manual. Genes which show characteristic expression profile can be identified and selected for functional analysis.

Furthermore, the identified gene can be used as a gene marker to figure out condition of the yeast cells during fermentation.

There is no particular limitation for the methods used for analysis of data and the method may be conducted according to the known means.

(n) Classification of Industrial Yeast

It is possible to classify industrial yeast using a DNA array mentioned above. Preparation of yeast genomic DNA and hybridization to a DNA array may be carried out as described before. Detection of the signal intensity of array is carried out using a Gene Chip Analysis Basic System and analysis soft ware (GCOS; GeneChip Operating Software 1.0) manufactured by Affymetrix. The percentage of probes, to which the DNA of brewing yeast hybridizes, is calculated and the identity between strain 34/70 and the tested strain is estimated. Industrial yeast strains can be classified on the basis of the identity.

(o) Detection of Nucleotide Polymorphism

It is possible to detect nucleotide polymorphism of a industrial yeast by comparative genomic hybridization with the DNA array mentioned above. The sets of oligonucleotides for each probe consist of Perfect Match oligonucleotide (PM) which is identical to the sequence of strain 34/70 and MisMatch oligonucleotide (MM) which contains a single base mismatch, for example, in the central position of the oligonucleotide. It is possible to detect nucleotide polymorphism from the gene whose signal intensity in MM is higher (for example, more than 5-fold) than that in PM.

(p) Selection of Genes for Functional Analysis

From the results of comparative genomic hybridization analysis, a gene which has probe sets showing low signal intensities may be lost or have different sequence from that of strain 34/70. In contrast, a gene which has probe sets showing high signal intensities may be high in copy number. Such genes can be selected for functional analysis because the locus may contribute to the difference of fermentation character between strain 34/70 and the tested strain. The genes which have nucleotide polymorphism detected by the method mentioned above can be also selected for functional analysis.

EXAMPLES

Details of the present invention are mentioned with the following Examples although the present invention is not limited to the following Examples.

Example 1

Preparation of Chromosomal DNA of
*Saccharomyces pastorianus* Weihenstephan 34/70
(Hereinafter, Abbreviated as Strain 34/70)

Preparation of chromosomal DNA was carried out by a method mentioned in "Yeast, a practical approach (IRL Press) 6.2.1 (pages 228-229)", which was partially modified. Cells were inoculated and grown in 200 mL of YPD medium (2% glucose, 1% yeast extract and 2% polypeptone) at 30° C. until absorbance of the culture at 660 nm became 4. Cells were collected by centrifugation and washed with buffer A (50 mM sodium phosphate, 25 mM EDTA and 1% (v/v) β-mercaptoethanol; pH 7.5), resuspended in 25 mL of buffer A, and 7 mg of Zymolyase 100T (Seikagaku Kogyo) was added thereto and the mixture was mildly shaken at 37° C. for 60 minutes. To this was added 25 mL of buffer B (0.2M Tris-HCl, 80 mM EDTA and 1% SDS; pH 9.5), then the mixture was allowed to stand at 65° C. for 30 minutes, cooled on ice, mixed with 12 mL of 5M potassium acetate and allowed to stand on ice for further 60 minutes. The resulting solution was centrifuged at 5,000 g for 10 minutes at 15° C. To the recovered supernatant was added the same volume of ethanol to precipitate DNA, and the mixture was immediately centrifuged at 5,000 g for 10 minutes at 15° C. to collect the precipitate. The resulting precipitate was washed with 70% (v/v) ethanol, subjected to natural drying and dissolved in 5 mL of TE buffer (10 mM Tris-HCl and 1 mM of EDTA; pH 8.0) to give a crude DNA solution. Cesium chloride (4.06 g) and 840 μg of bisbenzimide (Hoechst 33258) were added and dissolved in 3.5 mL of the crude DNA solution, the mixture was subjected to centrifugal separation at 100,000 g for 17 hours at 25° C. and exposed to UV light to make DNA bands visible, whereupon the band of the lower layer was recovered. The recovered DNA solution was extracted with isopropanol which was saturated with a cesium chloride solution to remove bisbenzimide (Hoechst 33258). To the recovered aqueous layer was added 4-fold by volume of 0.3 M sodium acetate followed by mixing, and then 3-fold by volume of ethanol was added thereto to precipitate the DNA, which was recovered by centrifugation. The recovered DNA was dissolved in TE buffer containing 75 μg/mL of RNase, kept at 37° C. for 5 minutes, and extracted with phenol/chloroform for three times and the aqueous layer was further subjected to precipitation with ethanol. The precipitate recovered by centrifugation was washed with 70% (v/v) ethanol, subjected to natural drying and dissolved in TE buffer to prepare a chromosomal DNA solution.

Example 2

Preparation of a Shotgun Library

The concentration of the genome solution of strain 34/70 prepared in Example 1 was adjusted to 1 mg/mL using a TE buffer and 0.1 mL thereof was treated with a Hydroshear (manufactured by GeneMachines; speed: 6; cycle: 20) to fragment the genomic DNA. The ends of the genomic fragment were blunted using a DNA Blunting Kit (manufactured by Takara Shuzo), fractionated by 0.8% agarose electrophoresis, and a genomic fragment of 1.5 to 2.5 kb was excised from the gel and DNA was eluted. The DNA eluate was treated with phenol/chloroform and precipitated with ethanol to give a genome library insert. All the above insert and 0.5 μg of pUC 18 SmaI/BAP (manufactured by Amersham Biosciences) were subjected to ligation at 15° C. for 15 hours using T4 ligase (manufactured by Takara Shuzo).

The ligation reaction product was precipitated with ethanol and dissolved in 10 μL of a TE buffer. A ligation solution (1 μL) was inserted into 40 μL of *Escherichia coli* Electro Cell DH5α (manufactured by Takara Shuzo) by means of electroporation under the condition mentioned in the attached experimental manual. The resulting product was spread on an LB plate medium containing 1.6% of agar (the LB medium (1% bactotryptone, 0.5% yeast extract and 1% sodium chloride; pH 7.0)) containing 0.1 mg/mL of ampicillin, 0.1 mg/mL of X-gal and 1 mmol/L of isopropyl-β-D-thiogalactopyranoside (IPTG), and incubated through the night at 37° C.

The transformants obtained from colonies formed on the said plate medium were subjected to cultivation without shaking through the night at 37° C. in a 384-well titer plate to which 50 μL of an LB medium containing 0.1 mg/mL of ampicillin was added, and then 50 μL of a 50% aqueous solution of glycerol was added thereto followed by stirring and the mixture was used as a glycerol stock.

Example 3

Preparation of a Cosmid Library

About 0.1 mg of the genome DNA obtained in Example 1 was partially digested with Sau3AI (manufactured by Takara Shuzo). Insertion of the fragment into a BamHI site of Super Cos I vector (manufactured by Stratagene) was carried out according to a manual. A ligated product prepared by this method was subjected to packaging using Gigapack III Gold (manufactured by Stratagene) and introduced into *Escherichia coli* XL1-Blue MR strain (manufactured by Stratagene) according to a manual. It was spread on an LB plate medium containing 0.1 mg/mL of ampicillin and incubated through the night at 37° C. The resulting transformants were cultured through the night at 37° C. in an LB medium (each well: 50 μL) containing 0.1 mg/mL of ampicillin using a 96-well titer plate, and then 50 μL of 50% glycerol solution was added thereto followed by stirring and the mixture was used as a glycerol stock.

Example 4

Determination of DNA Sequence (4-1) Preparation of DNA Fragment

The whole genome sequence of strain 34/70 was determined mainly using the whole genome shotgun method. A DNA fragment of which DNA sequence is to be determined by that method was prepared by a PCR method from the shotgun library prepared in the above Example 2. To be specific, clones derived from the whole genome shotgun library were inoculated using a replicator (manufactured by Gene Solution) to a 384-well titer plate where 50 µL of an LB medium containing 0.1 mg/mL of ampicillin was placed to each well and cultivated without shaking through the night at 37° C. The said culture liquid was transferred to a 384-well reaction plate (manufactured by AB Gene) containing 10 µL of reaction mixture for PCR (TaKaRa Ex Taq manufactured by Takara Shuzo) using a replicator (manufactured by Gene Solution) and PCR was carried out according to a protocol by Makino, et al. "DNA Research, volume 5, pages 1 to 9 (1998)" using a GeneAmp PCR System 9700 (manufactured by Applied Biosystems) to amplify the inserted fragment. After that, excessive primer and nucleotide were removed by a PCR product purification kit (manufactured by Amersham Bioscience) and a sequence reaction was carried out using the purified PCR sample as a template.

A DNA fragment from the cosmid library of the above Example 3 was prepared according to the following method. That is, clones derived from the whole cosmid library were inoculated to each well of a 96-well plate to which 1.0 mL each of a 2×YT medium (1.6% bactotrypsin, 0.1% yeast extract and 0.5% sodium chloride; pH 7.0) containing 50 µg/mL of ampicillin was placed and subjected to shake culture at 30° C. through the night. A cosmid DNA was prepared from the said culture using KURABO PI-1100 AUTOMATIC DNA ISOLATION SYSTEM (manufactured by KURABO) according to a manual of KURABO, and was used as a template for a sequence reaction.

(4-2) Sequence Reaction

A sequence reaction mixture was prepared as follows. The PCR product or cosmid DNA prepared in the above (4-1) was mixed with about 2 µl of DYEnamic ET Terminator Sequencing Kit (manufactured by Amersham Bioscience) and appropriate primers to give about 8 µl of reaction mixture. An M13 forward (M13-21) primer and an M13 reverse (M13RV) primer (manufactured by Takara Bio), were used for the sequence reaction of a PCR product derived from shotgun DNA, while a forward primer SS-cos F. 1 (SEQ ID NO: 7) and a reverse primer SS-cos R.1 (SEQ ID NO: 8) were used for cosmid DNA. Amounts of the primer and the DNA fragment were 3.2 pmol and 50 to 200 ng, respectively. The said reaction solution was subjected to dye terminator sequence reaction of 60 cycles using a GeneAmp PCR System 9700. Cycle parameter followed a manual attached to the DYEnamic ET Terminator Sequencing Kit. Purification of the sample was carried out using a Multi Screen HV Plate (manufactured by Millipore) according to a manual of Millipore. The purified reactant was stored in a dark place at 4° C. The said purified reactant was analyzed using a Mega BACE 1000 Sequencing System (manufactured by Amersham Bioscience) and ABI PRISM 3700 DNA Analyser (manufactured by Applied Biosystems) according to manuals attached thereto. The data on 332,592 sequences obtained by the Mega BACE 1000 Sequencing System and on 13,461 sequences obtained by the 3700 DNA Analyser were transferred to a server Enterprise 6500 (manufactured by Sun Microsystems) and preserved. The data on 346,053 sequences corresponded to about 7-fold of the whole genome size.

A list of the primers for the PCR used in the Example is shown in Table 3.

Example 5

Assembly (A Process Whereby the Order of Multiple Sequenced DNA Fragments is Determined)

All works for reconstruction of genomic DNA sequence from sequence information for DNA fragment of the 346,053 sequences obtained in the above Example 4 were carried out on a UNIX® platform. Base call was carried out by phred (The University of Washington), masking of vector sequence was carried out using Cross_Match (The University of Washington) and assembly was carried out using Phrap (The University of Washington). The contigs obtained as a result of the assembly were analyzed using a graphical editor consed (The University of Washington). A series of works from base call to assembly was carried out all together utilizing a script phredPhrap attached to the consed.

Example 6

Preparation of a Comparative Database with the Whole Genome Sequence of *S. cerevisiae*

*S. pastorianus* is believed to be a natural hybrid of *S. cerevisiae* with its closely-related species "Int. J. Syst. Bacteriol., volume 35, pages 508 to 511 (1985)". Therefore, a DNA sequence (comprising 10,044 bases) of both ends of the cosmid DNA clone obtained in (4-2) was subjected to a homology searching by a homology searching algorithm to the genome sequence of *S. cerevisiae*, whereupon for each DNA sequence alignment of homologous region on the genome sequence of *S. cerevisiae* and the identity thereof were determined to prepare a database. An identity distribution chart for cosmid DNA sequence with the corresponding genomic DNA sequence of *S. cerevisiae* is shown in FIG. 2. The DNA sequence of cosmids was roughly classified into a DNA sequence group showing not less than 94% identity to the genomic DNA sequence of *S. cerevisiae* and a DNA sequence group showing approximately 84% identity thereto. The DNA sequence group showing not less than 94% identity was named DNA sequence of Sc type derived from *S. cerevisiae* and the DNA sequence group showing approximately 84% identity was named DNA sequence of non-Sc type derived from genome of closely related species. Similarly, a comparative database (Table 1) was prepared for the DNA sequence of both ends of shotgun clone obtained in (4-1) with the genomic DNA sequence of *S. cerevisiae*. Table 1 shows an example of the comparative database of DNA sequence of both ends of 3,648-cosmid clone with the genomic DNA sequence of *S. cerevisiae*. Table 1 shows the homologous region and the identity of forward sequence and reverse sequence of cosmid subjected to the DNA sequence determination on each genomic DNA sequence of *S. cerevisiae*.

TABLE 1

| | Forward Chain | | | | | | Reverse Chain | | | | | |
|---|---|---|---|---|---|---|---|---|---|---|---|---|
| | | | Matched S. cerevisiae Genomic Base Sequence Information | | | | | | Matched S. cerevisiae Genomic Base Sequence Information | | | |
| Name of Cosmid | Sequence Length (bases) | Identical Length (bases) | Chromosome No. | Initiation Position (bases) | Termination Position (bases) | Identity (%) | Sequence Length (bases) | Identical Length (bases) | Chromosome No. | Initiation Position (bases) | Termination Position (bases) | Identity (%) |
| SSL052_A06 | 627 | 625 | XVI | 15,940 | 16,565 | 98.7 | 626 | 625 | XVI | 52,979 | 52,354 | 98.7 |
| SSL023_D02 | 346 | 341 | XVI | 16,784 | 17,125 | 87.3 | 633 | 629 | XVI | 66,017 | 65,388 | 90.5 |
| SSL015_E09 | 630 | 625 | XVI | 39,030 | 39,655 | 89.5 | 615 | 614 | XVI | 81,655 | 81,041 | 97.9 |
| SSL029_B08 | 664 | 660 | XVI | 45,916 | 45,256 | 99.3 | 650 | 647 | XVI | 8,504 | 9,151 | 98.8 |
| SSL028_G10 | 656 | 655 | XVI | 47,609 | 45,954 | 98.3 | 646 | 641 | XVI | 10,359 | 11,000 | 98.0 |
| SSL008_E01 | 622 | 620 | XVI | 46,362 | 45,982 | 93.4 | 589 | 587 | XVI | 86,022 | 85,435 | 98.3 |
| SSL030_G05 | 632 | 631 | XVI | 47,013 | 47,644 | 99.2 | 618 | 617 | XVI | 87,004 | 86,387 | 99.5 |
| SSL032_H10 | 646 | 645 | XVI | 52,076 | 51,431 | 98.1 | 637 | 636 | XVI | 13,273 | 13,909 | 98.7 |
| SSL041_G05 | 635 | 634 | XVI | 52,979 | 52,345 | 99.4 | 619 | 618 | XVI | 9,825 | 10,443 | 99.4 |
| SSL031_D08 | 659 | 658 | XVI | 52,297 | 52,955 | 99.2 | 638 | 637 | XVI | 92,295 | 91,658 | 99.1 |
| SSL069_F11 | 417 | 414 | XVI | 55,053 | 55,467 | 88.5 | 788 | 787 | XVI | 97,115 | 96,328 | 94.4 |
| SSL005_A10 | 647 | 645 | XVI | 65,233 | 64,588 | 99.2 | 527 | 516 | XVI | 21,537 | 22,053 | 81.8 |
| SSL014_G07 | 628 | 627 | XVI | 65,229 | 65,856 | 99.8 | 621 | 620 | XVI | 103,674 | 103,054 | 99.2 |

Figure 3:
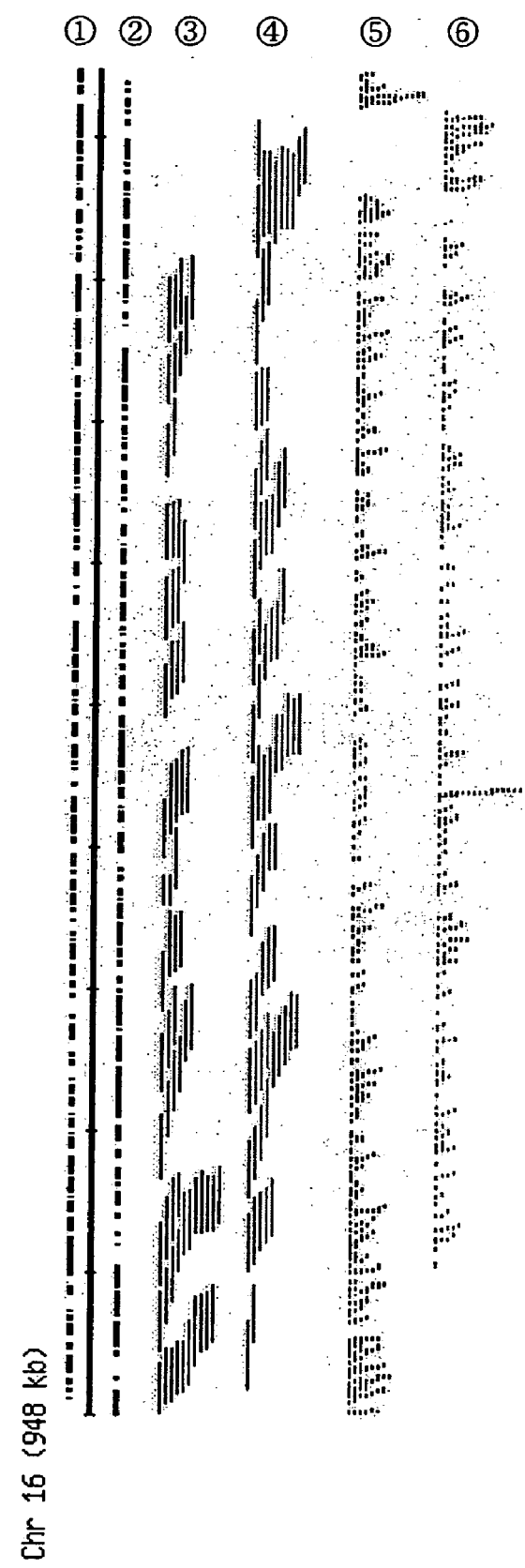
FIG. 3 shows a mapping example of cosmid and shotgun clones to genome sequence of *S. cerevisiae*. ① and ② show genes existing on Watson strand and Crick strand on the chromosome XVI of *S. cerevisiae*, respectively. ③ and ④ show Sc type and non-Sc type DNA fragments inserted in cosmid clones, respectively. ⑤ and ⑥ show Sc type and non-Sc type DNA fragments inserted in shotgun clones, respectively.
Figure 4:
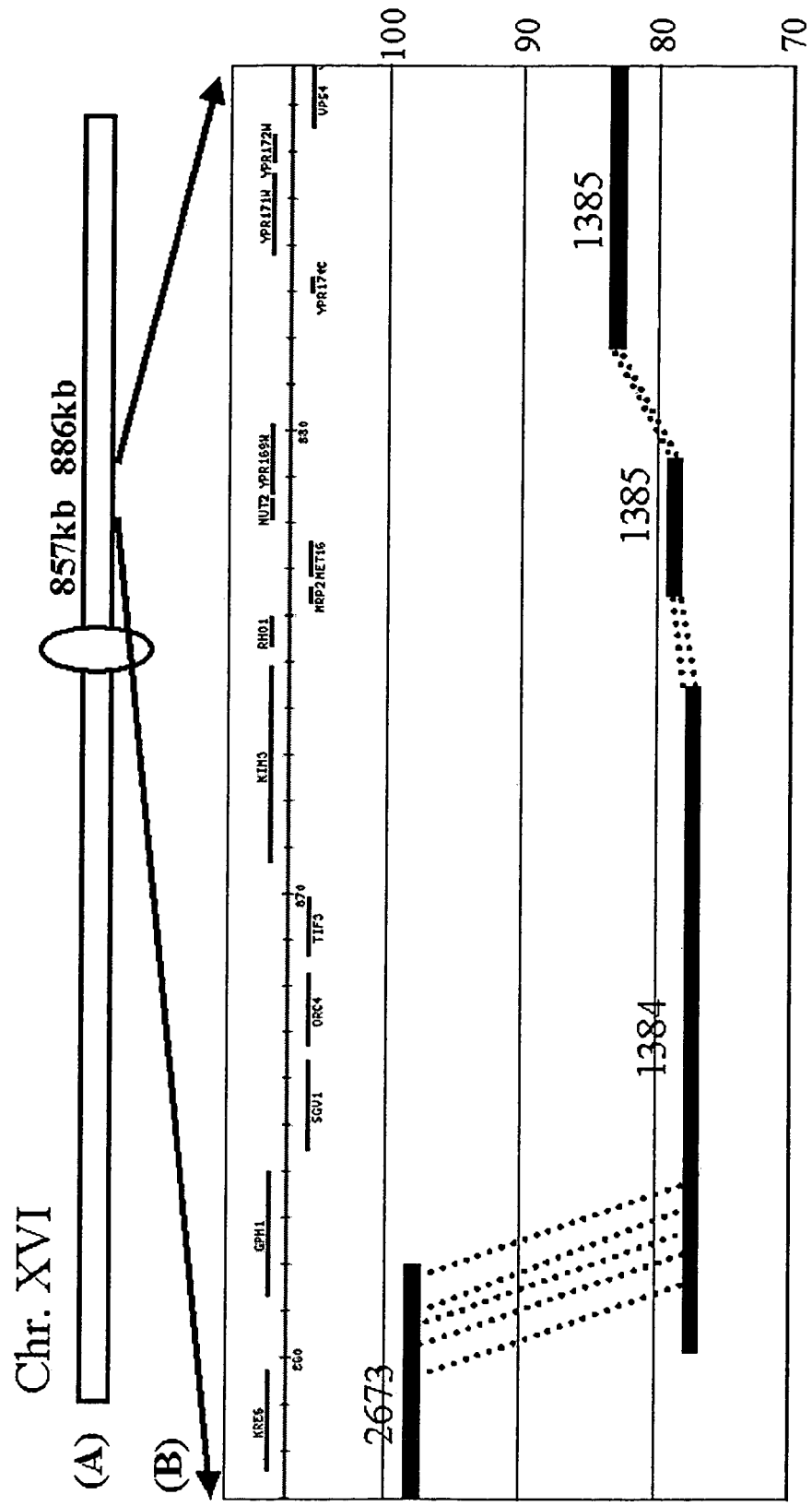
FIG. 4 shows a mapping example of contigs to the genome sequence of *S. cerevisiae*. (A) is a schematic depiction of Chromosome XVI of *S. cerevisiae*. (B) is a drawing where the parts of 857 to 886 kb of the Chromosome XVI of *S. cerevisiae* is enlarged. Y-axis indicates % identity of contigs against *S. cerevisiae* genome sequence. X-axis indicates position of contigs against *S. cerevisiae* genome sequence. Contigs (solid lines) are connected with the forward-reverse links (dot lines) from the shotgun and cosmid reads, respectively.

On the basis of the information obtained by the prepared comparative database, mapping of cosmid clone and shotgun clone on S. cerevisiae genome sequence was carried out (FIG. 3). In addition, a comparative database (Table 1) of contig DNA sequence obtained in Example 5 with S. cerevisiae genome sequence was prepared, then mapping was carried out. Although the means for the mapping was almost the same as the above-mentioned method, if forward and reverse sequence of cosmid and shotgun clones were present in different contigs, these contigs we connected by forward-reverse link (FIG. 4).

Example 7

Identification and Assignment of Function of ORF

Identification of ORF (open reading frame) in the DNA sequence assembled in Example 5 was carried out. The examples are specifically shown below. Identification of ORF existing in the DNA sequence assembled in Example 5 was carried out using a available program using ORF finder (Retrieved from Internet: <URL:http://www.ncbi.nih.gov/gorf/gorf.html>for identification of ORF for six kinds of reading frames in the sequence with the length of not less than 150 bases from initiation codon to termination codon including its complementary sequence. Assignment of function of the extracted ORF was carried out by homology searching of amino acid sequence of ORFs of S. cerevisiae that have been registered at the SGD and published. Table 2 shows examples of the ORF name of S. cerevisiae corresponding to the result of assignment of function of ORF existing in the non-Sc genome. From the left side of the table, name of the ORF existing on the brewing yeast, ORF length in polynucleotide, ORF length in polypeptide, name of the ORF of S. cerevisiae determined by homology searching, identity, coincided length and functions of the gene are shown.

TABLE 2

| Name of ORF | ORF Length (bp) | ORF Length (aa) | Name of Homologous Gene | Identity (%) | Coincided Length (aa) | Functions |
|---|---|---|---|---|---|---|
| nonSc-ATF2 | 1638 | 545 | ATF2 | 71 | 535 | alchhol O-acetyltransferase |
| nonSc-THI3 | 1305 | 434 | THI3 | 94 | 431 | transcriptional activator |
| nonSc-FUS3 | 435 | 144 | FUS3 | 90 | 139 | MAP kinase |
| nonSc-ILV5 | 1188 | 395 | ILV5 | 97 | 395 | ketol-acid reductoisomerase |
| nonSc-MET2 | 1461 | 486 | MET2 | 93 | 486 | homoserine O-acetyltransferase |
| nonSc-MET10 | 3108 | 1035 | MET10 | 87 | 1035 | sulfite reductase (NADPH) |
| nonSc-MET14 | 609 | 202 | MET14 | 97 | 202 | adenylsulfate kinase |
| nonSc-MET16 | 786 | 261 | MET16 | 92 | 261 | phosphoadenylyl-sulfate reductase |
| nonSc-TPI1 | 747 | 248 | TPI1 | 96 | 248 | triosephosphate isomerase |
| nonSc-MET3 | 1536 | 511 | MET3 | 94 | 511 | sulfate adenylyltransferase (ATP) |
| nonSc-MET10 | 3108 | 1035 | MET10 | 87 | 1035 | sulfite reductase (NADPH) |
| nonSc-SAM1 | 1149 | 382 | SAM1 | 97 | 382 | methionine adenosyltransferase |
| nonSc-SSU1 | 1377 | 458 | SSU1 | 78 | 457 | sulfite transporter |

Example 8

Analysis of Chromosome Structure by DNA Microarray-Based Comparative Genomic Hybridization and PCR Preparation of genomic DNA from yeast was carried out using Qiagen Genomic Tip 100/G (#10243: manufactured by Qiagen) and Qiagen Genomic DNA Buffer Set (#19060: manufactured by Qiagen) according to the manuals attached to the kits. The DNA (10 μg) was digested with DNase I (manufactured by Invitrogen) according to a method of Winzeler, et al. "Science, volume 281, pages 1194 to 1197 (1998)", biotinylated by a terminal transferase (manufactured by Roche) and hybridized to a DNA microarray (Affymetrix Gene Chip Yeast Genome S98 Array: produced by Affymetrix). Hybridization and detection of signal intensity of array were carried out using a Gene Chip Analysis Basic System manufactured by Affymetrix.

Figure 5:
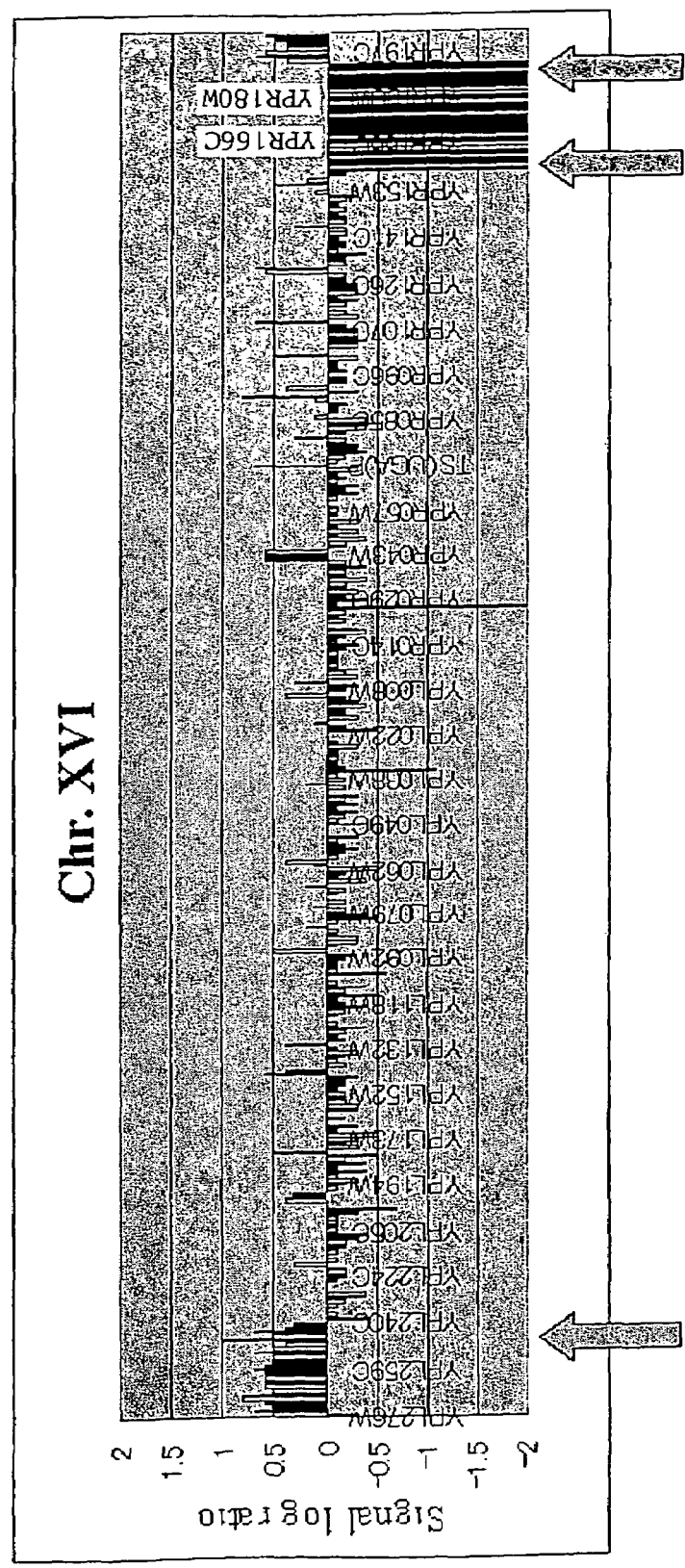
FIG. 5 shows the result of DNA microarray-based comparative genomic hybridization. The genomic DNA of strain 34/70 was hybridized to a DNA microarray (Affymetrix Gene Chip Yeast Genome S98 Array) and the signal of each ORF (open reading frame) was normalized to that of the haploid strain S288C and shown as Signal Log Ratio (2"). Signal Log Ratios were lined following genes order in Chromosome XVI. The non-Sc type genes do not hybridize to this Sc type array, therefore, the points (indicated by arrows) where the Signal Log Ratios show vigorous changes were considered to be translocation sites.

The signal of each probe hybridized with the DNA of strain 34/70 is normalized to that of the haploid laboratory yeast strain S288C using an analysis soft ware (Microarray Suite 5.0: manufactured by Affymetrix) and shown as signal log ratio (2"). Signal log ratios were lined following genes order in each chromosome using a spreadsheet program (Microsoft Excel 2000) and the signal log ratios are shown in bar graphs as shown in FIG. 5. The non-Sc type genes do not hybridize to the S. cerevisiae array, therefore, the Sc type gene dosage affect the signal log ratio and the points where the signal log ratios show vigorous changes are considered to be translocation sites between Sc type and non-Sc type chromosome.

On the basis of genome sequence of strain 34/70 determined by a shotgun method, the chimera chromosome structure was confirmed by PCR where two pairs of primers having DNA sequences in which one side is Sc type while the other side is a non-Sc type (XVI-1(L)cer-95894 (SEQ ID NO: 9) /XVI-1(R)nonSc-106302rv (SEQ ID NO: 10) and XVI-2(L)cer-859737 (SEQ ID NO: 11)/XVI-2(R)nonSc-864595rv (SEQ ID NO: 12) were designed and the genomic DNA derived from strain 34/70 was used as a template. Two examples of translocation of chromosome XVI are shown as follows.

The PCR was carried out using Takara LA Taq™ and a buffer attached thereto in accordance with the attached manual by a Takara PCR Thermal Cycler SP.

As a result of the PCR, it was confirmed by a 0.8% agarose electrophoresis that, a DNA fragment in the predicted length was amplified from strain 34/70, while when genomic DNA of the experimental strain S. cerevisiae X2180-1A was used as a template for the PCR, amplification of the DNA fragment was not detected. Furthermore, when DNA sequence of both ends of the DNA fragment amplified from strain 34/70 was confirmed, it was consistent with the genome sequence determined by a shotgun method and it was confirmed that, within such a region, translocation between Sc type and non-Sc type chromosome took place.

Figure 6:
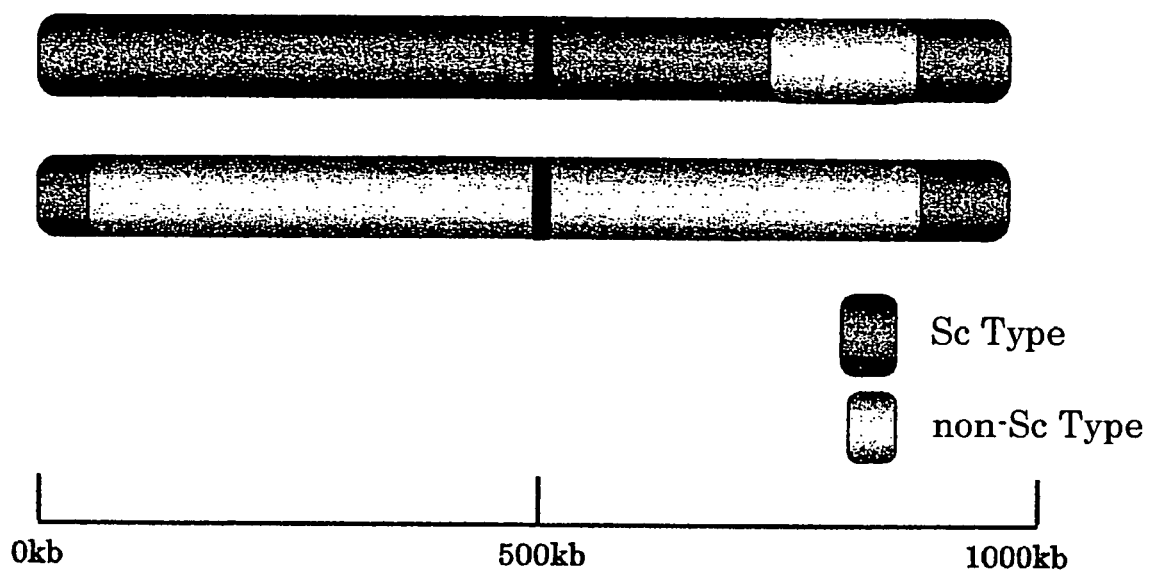
FIG. 6 shows the structure of the Chromosome XVI of strain 34/70 deduced from DNA microarray and PCR analysis.

From the above result, it is estimated that at least two kinds of chromosomes were present in the chromosome XVI as shown in FIG. 6. According to the same technique, ligation between Sc chromosome and non-Sc chromosome (or inverse thereof) or, in other words, the region where the existence of chimera chromosome structure was suggested was confirmed. Such chimera chromosome structure of the Sc chromosome and non-Sc chromosome was confirmed in at least 13 places in the total chromosomes of strain 34/70 (FIG. 1).

As a result of genome analysis, it was found that chromosome structure of bottom fermenting yeast was very complicated and there were at least 37 kinds of chromosomes in strain 34/70.

Example 9

Cloning of SSU1 Genes of Strain 34/70

The shotgun clone containing non-ScSSU1 gene was retrieved using a comparative database obtained in Example 6. There was SSS103_G08 which contained about 2.4 kb of fragment containing full-length of non-ScSSU1 ORF, where identity of forward and reverse sequence of shotgun clone to those of S. cerevisiae were 62.9% and 82.9%, respectively.

SSS103-G08 was selected from a library of genomic DNA, then full length of non-ScSSU1 was prepared by PCR. Synthetic DNAs of SacI-non-Sc-SSU1_for 1 (SEQ ID NO: 13) and BglII-non-Sc-SSU1_rv1460 (SEQ ID NO: 14) were used as primers. As a result of such a combination, base numbers 1 to 1460 of nonScSSU1 was amplified to give a SacI-BglII fragment of about 1.5 kb.

With regard to an ScSSU1 gene, the full length gene was obtained by PCR using a primer pair designed on the basis of the information of SGD using the genomic DNA of strain 34/70 as a template. Synthetic DNAs of SacI-ScSSU1_for 1 (SEQ ID NO: 15) and BglII-ScSSU1_rv1406 (SEQ ID NO: 16) were used as primers. As a result of such a combination, base numbers 1 to 1406 of ScSSU1 gene was amplified to give a SacI-BglII fragment of about 1.4 kb.

ScSSU1 and non-ScSSU1 genes obtained as above were inserted using TA cloning kit (Invitrogen) into pCR 2.1-TOPO vector attached to the kit, and they were named TOPO/ScSSU1 and TOPO/non-ScSSU1, respectively. Sequences of the resulting ScSSU1 and non-ScSSU1 genes were confirmed by a method of Sanger "F. Sanger, Science, volume 214, page 1215, 1981" (FIG. 10).

Example 10

Disruption of each SSU1 Gene

According to a method mentioned in the document "Goldstein, et al., Yeast, volume 15, page 1541 (1999)", DNA fragments for gene disruption were prepared by PCR using a plasmid containing a drug-resistance marker (pFA6a (G418"), pAG 25 (nat1)) as a template. As a primer for the PCR, non-Sc-SSU1_for (SEQ ID NO: 17) /non-Sc-SSU1_rv (SEQ ID NO: 18) was used for disruption of non-ScSSU1 gene, while for disruption of ScSSU1 gene, ScSSU1_for (SEQ ID NO: 19)/ScSSU1_rv (SEQ ID NO: 20) was used. For disruption of non-ScSSU1 gene, a plasmid pPGAPAUR (AUR1-C) and a primer non-Sc-SSU1_for +pGAPAUR (SEQ ID NO: 21) /non-Sc-SSU1_rv+AURI-C (SEQ ID NO: 22) were further used. As such, two and three kinds of DNA fragments were prepared for ScSSU1 and non-ScSSU1 gene disruption, respectively.

The bottom fermenting yeast BH 96 was transformed using the DNA fragment for gene disruption prepared with the method above. The transformation was carried out by a method mentioned in the Japanese Patent Laid-Open Gazette No. 07/303,475 and concentrations of the drugs were 300 mg/L for geneticin, 50 mg/L for nourseothricin and 1 mg/L for aureobasidin A.

With regard to the transformants prepared, gene disruption was confirmed by Southern analysis. Firstly, the genomic DNA extracted from parental strain and disruptant was subjected to restriction enzyme treatment (at 37° C. or 18 hours) using NcoI for the confirmation of ScSSU1 gene disruption and HindIII for the confirmation of non-ScSSU1 gene disruption, and then fractionated by 1.5% agarose gel electrophoresis and transferred to a membrane. After that, hybridization was carried out (at 55° C. for 18 hours) with a probe specific to the ScSSU1 or non-ScSSU1 following a protocol of the Alkphos Direct Labelling Reagents (Amersham) and signals were detected by CDP-Star.

Each of the strains where gene disruption was confirmed was named as follows.
Sc-1 (ScSSU1/Scssu1::G418$^r$)
Sc-2 (Scssu1::G418$^r$/Scssu1::nat1)
non-Sc-1 (non-ScSSU1/non-ScSSU1/non-Scssu1::G418$^r$)
non-Sc-2 (non-ScSSU1/non-Scssu1::G418$^r$/non-Scssu1::nat1) non-Sc-3
(non-Scssu1::G418$^r$/non-Scssu1::nat1/non-Scssu1::AUR1-C)

Example 11

Quantitative Analysis of Sulfite Production in a Fermentation Test

Fermentation test using parental strain and disruptant Sc-1 to non-Sc-3 prepared in Example 10 was carried out under the following condition.
 Original extract: 12.75%
 Fermentation scale: 2 liters
 Dissolved oxygen concentration: about 9 ppm
 Fermentation temperature: 15° C.
 Pitching rate: 10 g of wet yeast cells/2 L of wort Wort was periodically sampled and monitored in cell growth (OD 600) (FIG. 7-(a)), apparent extract (FIG. 7-(b)) and sulfite concentration (FIG. 7-(c)). Quantitative analysis of sulfite in wort was carried out in such a method by which sulfite is captured in a hydrogen peroxide solution by means of distillation in an acidic condition and subjected to titration with an alkali (Revised Method for BCOJ Beer Analysis by the Brewing Society of Japan).

As a result, sulfite production in the wort by ScSSU1 disruptant was nearly the same as that produced by the parental strain, while it significantly decreased by non-ScSSU1 disruptant. It was suggested that non-ScSSU1 gene which is specific to bottom fermenting yeast greatly contributes to sulfite production in wort.

At the same time, growth rate and extract-consuming rate were significantly decreased in the non-ScSSU1 disruptant, and it supported that excessive sulfite in cells causes inhibition of cell growth.

Example 12

Overexpression of each SSU1 Gene

From the plasmid TOPO/non-ScSSU1 mentioned in Example 9, a fragment of about 1.5 kb including the full length of non-ScSSU1 ORF was excised by a treatment with restriction enzymes (SacI-BglII). Then this fragment was inserted into a plasmid pNI-NUT which was similarly treated with restriction enzymes (SacI-BglII) to construct a non-ScSSU1 overexpression vector pYI-non-ScSSU1. The vector pNI-NUT contains URA3 as a homologous recombination site and nourseothricin-resistance gene (nat1) and ampicillin-resistance gene (Amp$^r$) as selective markers. On the other hand, the ScSSU1 overexpression vector pNI-ScSSU1 has a structure where the non-ScSSU1 gene of the above-mentioned pYI-non-ScSSU1 is substituted with the SSU1-R of about 2 kb derived from S. cerevisiae"J. Ferment. Bioeng., volume 86, page 427 (1998)". For overexpression of each SSU1 gene, promoter and terminator of glyceraldehyde-3-phosphate dehydrogenase gene (TDH3) were used.

Bottom fermenting yeast BH225 was transformed by a overexpression vector prepared following the above-mentioned method. Transformation was carried out by a method mentioned in the Japanese Patent Laid-Open Gazette No. 07/303,475 and selected on YPD plate medium containing 50 mg/L of nourseothricin.

Confirmation of the overexpression was carried out by RT-PCR. Extraction of total RNA was carried out using an RNeasy Mini Kit (Qiagen), according to the manual of "for total RNA isolation from yeast" attached the kit. ScSSU1_for 331 (SEQ ID NO: 23)/ScSSU1_982rv (SEQ ID NO: 24) were used as ScSSU1-specific primers; non-ScSSU1_for 329 (SEQ ID NO: 25)/non-ScSSU1_981rv (SEQ ID NO: 26) were used as non-ScSSU1-specific primers; and PDA1_for 1 (SEQ ID NO: 27)/PDA1_730rv (SEQ ID NO: 28) were used as specific primers for constitutively expressed gene PDA1 used as an internal standard. PCR product was fractionated by 1.2% agarose electrophoresis, stained with an ethidium bromide solution and signal value of each SSU1 gene of transformant was normalized with a signal value of PDA 1 and compared with that of the parental strain. The overexpressed strains confirmed as such, were named as ScSSU1 overexpressed strain and non-ScSSU1 overexpressed strain.

Example 13

Quantitative Analysis of Sulfite Production in a Fermentation Test

Fermentation tests using parental strain and each of the SSU1 overexpressed strains obtained in the Example 12 were carried out under the following condition.
 Original extract: 12.83%
 Fermentation scale: 2 liters
 Dissolved oxygen concentration: about 9 ppm
 Fermentation temperature: 12° C.
 Pitching rate: 10 g of wet yeast cells/2 L of wort As in Example 11, Wort was periodically sampled and monitored in cell growth (OD 600) (FIG. 8-(a)), apparent extract (FIG. 8-(b)) and sulfite concentration (FIG. 8-(c)). With regard to the sulfite production, it was only slightly higher in Sc SSU1 overexpressed strain (19 ppm at the end of the fermentation) as compared with that of the parental strain (12 ppm at the same stage), while non-Sc SSU1 overexpressed strain showed a significant increase (45 ppm at the same stage). At the same time, there was no difference in the growth rate and in the extract-consuming rate between the parental strain and the overexpressed strains.

From the above result, by overexpression of the gene encoding the sulfite-discharging pump specific to the bottom fermenting yeast shown in the present invention, it is possible to to increase sulfite concentration in beer without changing the fermentation process and the fermentation period. As a result, it is now possible to produce an alcoholic beverage with excellent flavor stability and a longer quality preservation period.

Example 14

Cloning of MET14 Gene of Strain 34/70

DNA sequence of non-Sc MET14 gene was retrieved from the comparative database obtained in Example 6. A shotgun clone SSS 134_021 containing about 1.9 kb (full-length) of non-Sc MET14 gene was obtained; its forward and reverse DNA sequence identity to *S. cerevisiae* were 79.0% and 56.0%, respectively.

The shotgun clone 134_021 was selected from a shotgun library and the full length non-Sc MET14 gene was obtained by PCR. As a primer pair, synthetic DNAs of SacI-nonSc-MET14_for-21 (SEQ ID NO: 29) and BamHI-nonSc-MET14_rv618 (SEQ ID NO: 30) were used (Table 3). As a result of such a combination, a non-Sc MET14 gene (about 0.6 kb) embraced by SacI and BamHI restriction sites was obtained.

The Sc MET14 and non-Sc MET14 genes obtained as above were inserted using a TA cloning kit (manufactured by Invitrogen) into pCR 2.1-TOPO vector attached to the kit, and they were named TOPO/ScMET14 and TOPO/nonSc-MET14, respectively.

DNA sequences of the resulting Sc MET14 and non-Sc MET14 genes were checked by a method by Sanger "Science, volume 214, page 1215 (1981)" (FIG. 11).

Example 15

Over Expression of each MET14 Gene in Sc SSU1 Overexpressed Strain

A fragment of about 0.6 kb containing Sc MET14 or non-Sc MET14 mentioned in Example 14 was inserted into the multi-cloning site of the expression vector pUP3GLP (Japanese Patent Laid-Open Gazette No. 2000/316,559) to

TABLE 3

| SEQ ID No | Sequence Name | 5'-Base Sequence-3' |
|---|---|---|
| 5 | M13 for | agtcacgacg ttgta |
| 6 | M13 rv | caggaaacag ctatgac |
| 7 | SS-cosF. 1 | aggcgtatca cgaggccctt tc |
| 8 | SS-cosR. 1 | cttatcgatg ataagcggtc aaacatgag |
| 9 | XVI-1(L) cer-95894 | cgcaagctcc gtacgttcaa cattcttatg aacggc |
| 10 | XVI-1(R) nonSc-106302rv | gcatcatcgt cgtgatcctt ctttggcaaa tgcagg |
| 11 | XVI-2(L) cer-859737 | gcgggtattt tgatggtaaa tctacaagcc ctcggc |
| 12 | XVI-2(R) nonSc-864595rv | cccagacaca gtttccagta tcatcctcgc agaac |
| 13 | SacI-nonScSSU1_for1 | gagctcatgg tcgctagttg gatgct |
| 14 | BglII-nonScSSU1_rv1460 | agatctcagc ttcagcccaa tccatt |
| 15 | SacI-ScSSU1_for1 | gagctcatgg ttgccaattg ggtact |
| 16 | BglII-ScSSU1_rv1406 | agatctctcc tacatgaaat gcttgc |
| 17 | nonScSSU1_for | atggtcgcta gttggatgct cactgccaca agggatttca acccttcat atcgaatatt ctgtacagct gtttgtcatg gttatggggg tcggtatttc ccttgacagt cttgacgtgc |
| 18 | nonScSSU1_rv | tgttaaatat gtactatcga tagccgagtt tgattcctcc acactttcga acagtcttct ccgtcccttc ctctgataaa tgctgttgaa aggagaattg cgcacttaac ttcgcatctg |
| 19 | ScSSU1_for | atggttgcca attgggtact tgctcttacg aggcagtttg acccttcat gtttatgatg gtcatgggtg tcggcatttc atcgaatatt ctatatagct ccttgacagt cttgacgtgc |
| 20 | ScSSU1_rv | ttatgctaaa cgcgtaaaat ctagagccga gtttgattct tccacgcttt caatgctgtt atacggagaa actgtcgtct tttccgtacc tgactctgaa cgcacttaac ttcgcatctg |
| 21 | nonScSSU1_for + pGAPAUR | atggtcgcta gttggatgct cactgccaca agggatttca acccttcat gtttgtcatg gttatggggg tcggtatttc atcgaatatt ctgtacagct ccggagctta ccagttctca |
| 22 | nonScSSU1_rv + AUR1-C | tgttaaatat gtactatcga tagccgagtt tgattcctcc acactttcga tgctgttgaa aggagaattg acagtcttct ccgtcccttc ctctgataaa tcgactctag aggatccaga |
| 23 | ScSSU1_for331 | tcgaaagcga acacgacgaa |
| 24 | ScSSU1_982rv | cgacagaaat cacggtgaaa a |
| 25 | nonScSSU1_329 | tgtcacaaaa atttaccacg ac |
| 26 | nonScSSU1_981rv | aagggaaatt accgtaaaga ag |
| 27 | PDA1_for1 | atgtttgtcg cacctgtatc t |
| 28 | PDA1_730rv | gattagaggc accatcac |
| 29 | SacI-nonSc-MET14_for-21 | ctcgagctct cgtgaaattc attgaaacaa atg |
| 30 | BamHI-nonSc-MET14_rv618 | ggatccttat aagatttata gatgcttccg |
| 31 | SacI-ScMET14_for | ctcgagctca gaaaagttgg aattatttct cca |
| 32 | BamHI-ScMET14_rv | ggatccaatg tacagtaatc ggtcaaatta |

With regard to an Sc MET14 gene, a full length of the structural gene was obtained by PCR using a primer pair designed on the basis of the information of SGD and using genomic DNA of strain 34/70 as a template. Synthetic DNAs of SacI-ScMET14_for (SEQ ID NO: 31) and BamHI-ScMET14_rv (SEQ ID NO: 32) were used as primers. As a result of such a combination, a Sc MET14 gene (about 0.6 kb) embraced by SacI and BamHI restriction sites was obtained.

construct overexpression vectors pUP3Sc MET14 and pUP3nonSc-MET14 in which each MET14 gene was expressed under control of glyceraldehyde-3-phosphate dehydrogenase promoter and terminator. Top fermenting yeast, strain KN009F, was transformed by an Sc SSU1 overexpression vector pNI-SSU1 mentioned in Example 12 to prepare strain FOY227 which is an Sc SSU1 overexpressed strain. Strain FOY227 was transformed by the above pUP3ScMET14 and pUP3nonSc-MET14 to prepare strain FOY306 and strain FOY 307 in which Sc MET14 and non-Sc MET14, together with Sc SSU1, are overexpressed, respectively.

Example 16

Quantitative Analysis of Sulfite Production in a fermentation test

Figure 9:
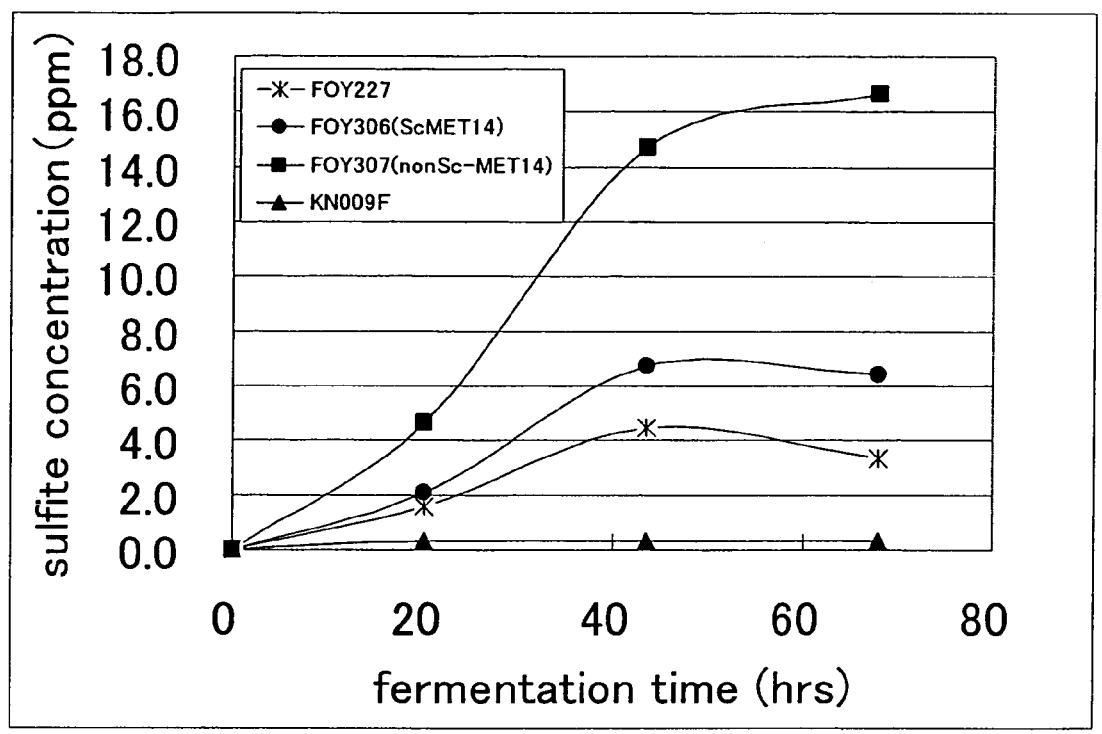
FIG. 9 shows the change of sulfite concentration during fermentation using MET14 overexpressed strains and parental strains (KN009F and FOY227).

Fermentation tests were carried out using strains prepared in Example 15; strain FOY227 which is an Sc SSU1 overexpressed strain, strain FOY306 which is an Sc MET14 overexpressed strain in strain FOY227, strain FOY307 which is a non-Sc MET14 overexpressed strain in strain FOY227 and the parental strain KN009 F under the following condition.
 Original extract: 12.84%
 Fermentation scale: 1.5 liters
 Dissolved oxygen concentration: about 9 ppm
 Fermentation temperature: 25° C. at all times
 Pitching rate: 7.5 g of wet yeast cells/1.5 L of wort As in Example 11, wort was periodically sampled and monitored in cell growth (OD 600), apparent extract and sulfite concentration. With regard to the yeast growth and the consumed amount of extract, there was no difference among the strains. However, with regard to the sulfite production, it was only slightly higher in Sc SSU1 overexpressed strain FOY227 (3.4 ppm at the end of the fermentation), and Sc MET14 and Sc SSU1 overexpressed strain FOY306 (6.4 ppm at the same stage) as compared with that of the parental strain KN009F (0.32 ppm at the same stage), while non-Sc MET14 and Sc SSU1 overexpressed strain FOY307 showed a significant increase (16.6 ppm at the same stage) as shown in FIG. 9.

From the above results, it was found that overexpression of the gene encoding the adenylyl sulfate kinase specific to the bottom fermenting yeast shown in the present invention was effective to increase sufite concentration in beer without changing the fermentation process and the fermentation time. As a result, it is now possible to produce an alcoholic beverage with excellent flavor stability and a longer quality preservation period.

Example 17

Production of the Bottom Fermenting Yeast DNA Microarray

DNA microarray of bottom fermenting yeast was produced based on the DNA sequence information of the ORFs obtained in the above (h) and intergenic DNA sequences located between ORFs deduced from whole genome sequence of strain 34/70.

Production of the DNA Microarray

Based on the DNA sequence information of the following four groups; (1) 22483 regions from the whole genome sequence information of 34/70 strain, (2) 403 *S. cerevisiae* ORFs from SGD which are not identified as Sc type ORFs in 34/70 strain, (3) 27 regions from *S. pastorianus* genes submitted in Genbank, (4) 64 DNA sequences of genes used as internal standard, PM probes (Perfect Match Probe; 25 base long) which are unique against whole genome sequence of the bottom fermenting yeast were designed using GeneChip® (Affymetrix) technology. In order to obtain quantitative and reproducible information, 11 probes and 20 probes were designed for each locus or region of (1), (2), (3) and (4) respectively. To further increase the sensitivity and specificity of the detection, mismatch probes (MM probe) that have sequences identical to the PM probe with the exception of one mismatched base at the central position (i.e. base 13) was also designed.

All of designed PM and MM probes were synthesized and packed in the glass slide (manufactured by Affymetrix) to produce the microarray using GeneChip® technology.
(1) was comprised in;

A) 6307 DNA sequences of non-Sc type ORFs, B) 7640 DNA sequences of Sc type ORFs, C) 28 DNA sequences of mitochondrial ORFs from 34/70 strain, D) 553 DNA sequences which have not been identified as the above ORFs but have some similarity to the proteins of *S. cerevisiae* using NCBI-BlastX homology searching, E) 7955 intergenic DNA sequences between as above A) or B).
(2) was comprised in;

YBL108C-A, YBR074W, YFL061W, YIL165C, YGR291C, YJR052W, YDR223W, YAL025C, YAR073W, YFL057C, YLL015W, YJR105W, YLR299C-A, YNR073C, YDL246C, YHL049C, YAR010C, YKL096W, YBL026W, YMR230W, YAL037C-A, YAL037C-B, YAL037W, YAL063C-A, YAL064C-A, YAL064W, YAL065C, YAL068W-A, YAL069W, YAR009C, YAR020C, YAR042W, YAR047C, YAR053W, YAR060C, YAR061W, YAR062W, YBL027W, YBL040C, YBL068W-A, YBL101W-B, YBL109W, YBL112C, YBR092C, YBR191W-A, YBR219C, YCL019W, YCL029C, YCL065W, YCL066W, YCL068C, YCL069W, YCL073C, YCL074W, YCL075W, YCL076W, YCR035C, YCR036W, YCR038W-A, YCR101C, YCR104W, YCR105W, YCR106W, YCR107W, YCR108C, YDL003W, YDL037C, YDL064W, YDL073W, YDL094C, YDL095W, YDL096C, YDL136W, YDL143W, YDL152W, YDL191W, YDL200C, YDL201W, YDL247W-A, YDL248W, YDR014W, YDR015C, YDR034C-D, YDR039C, YDR045C, YDR098C-B, YDR160W, YDR210C-D, YDR210W-B, YDR215C, YDR225W, YDR261C-D, YDR261W-B, YDR292C, YDR302W, YDR304C, YDR305C, YDR342C, YDR344C, YDR364C, YDR365W-B, YDR427W, YDR433W, YDR471W, YDR510C-A, YDR543C, YDR544C, YEL012W, YEL075W-A, YER039C-A, YER046W-A, YER056C-A, YER060W-A, YER074W, YER138C, YER187W, YER188C-A, YER190C-A, YFL002W-A, YFL014W, YFL019C, YFL020C, YFL030W, YFL031W, YFL051C, YFL052W, YFL053W, YFL054C, YFL055W, YFL056C, YFL063W, YFL065C, YFL066C, YFL067W, YFR012W-A, YGL028C, YGL041C, YGL052W, YGL210W-A, YGL259W, YGL262W, YGL263W, YGR034W, YGR038C-B, YGR089W, YGR107W, YGR109W-A, YIL082W-A, YGR122C-A, YGR146C, YGR148C, YGR161W-B, YGR182C, YGR183C, YGR271C-A, YGR290W, YGR295C, YHL009W-A, YHL009W-B, YHL015W-A, YHL046W-A, YHL047C, YHL048C-A, YHL048W, YHR032C-A, YHR032W-A, YHR039C-A, YHR043C, YHR070C-A, YHR071C-A, YHR071W, YHR141C, YHR165W-A, YHR179W, YHR180C-B, YHR180W-A, YHR182W, YHR193C, YHR193C-A, YHR207C, YHR211W, YHR213W-A, YHR216W, YHR217C, YHR218W-A, YIL029C, YIL052C, YIL069C, YIL148W, YIL171W, YIL174W, YIL176W, YIR018C-A, YIR041W, YIR042C, YIR043C, YIR044C, YJL012C-A, YJL014W, YJL062W-A, YJL136C, YJL175W, YJL222W-B, YJR024C, YJR027W, YJR032W, YJR053W, YJR054W, YJR094W-A, YJR107W, YJR110W, YJR111C, YJR140W-A, YJR151C, YJR152W,

YJR153W, YJR154W, YJR155W, YJR162C, YKL018W, YKL020C, YKL044W, YKL224C, YKL225W, YKR012C, YKR013W, YKR017C, YKR018C, YKR019C, YKR020W, YKR035C, YKR036C, YKR040C, YKR041W, YKR042W, YKR052C, YKR053C, YKR057W, YKR062W, YKR094C, YKR102W, YKR103W, YKR104W, YLL014W, YLL030C, YLL037W, YLL038C, YLL043W, YLL065W, YLR029C, YLR030W, YLR062C, YLR098C, YLR099W-A, YLR107W, YLR139C, YLR140W, YLR142W, YLR144C, YLR145W, YLR154C-G, YLR154W-A, YLR154W-B, YLR154W-C, YLR154W-E, YLR154W-F, YLR155C, YLR156W, YLR157C-B, YLR157W-C, YLR162W, YLR205C, YLR207W, YLR209C, YLR227W-B, YLR236C, YLR237W, YLR238W, YLR245C, YLR251W, YLR271W, YLR278C, YLR287C-A, YLR305C, YLR306W, YLR311C, YLR317W, YLR338W, YLR344W, YLR345W, YLR354C, YLR364W, YLR380W, YLR401C, YLR402W, YLR410W-B, YLR411W, YLR412C-A, YLR412W, YLR413W, YLR448W, YLR460C, YLR461W, YLR463C, YLR465C, YML003W, YML039W, YML073C, YMR087W, YMR143W, YMR175W-A, YMR247W-A, YMR268W-A, YMR324C, YMR325W, YNL020C, YNL035C, YNL054W-B, YNL243W, YNR034W-A, YNR075C-A, YNR077C, YOL038C-A, YOL053W, YOL101C, YOL103W-B, YOL162W, YOL163W, YOL164W, YOL164W-A, YOL165C, YOL166C, YOL166W-A, YOR050C, YOR096W, YOR101W, YOR192C-B, YOR192C-C, YOR225W, YOR235W, YOR343W-B, YOR366W, YOR381W-A, YOR382W, YOR383C, YOR384W, YOR385W, YOR386W, YOR387C, YOR389W, YPL003W, YPL019C, YPL023C, YPL036W, YPL048W, YPL055C, YPL060C-A, YPL175W, YPL194W, YPL197C, YPL257W-B, YPR002C-A, YPR008W, YPR014C, YPR028W, YPR043W, YPR048W, YPR087W, YPR094W, YPR108W, YPR137C-B, YPR161C, YPR162C, YPR163C, YPR164W, YPR165W, YPR166C, YPR167C, YPR168W, YPR169W, YPR169W-A, YPR170C, YPR170W-A, YPR171W, YPR172W, YPR173C, YPR174C, YPR175W, YPR176C, YPR177C, YPR178W, YPR179C, YPR180W, YPR181C, YPR182W, YPR183W, YPR184W, YPR185W, YPR186C, YPR187W, YPR188C, YPR189W, and YPR190C (3) was comprised in;

GenBank Accession No. AY130327, BAA96796.1, BAA96795.1, BAA14032.1, NP_012081.1, NP_009338.1, BAA19915.1, P39711, AY130305, AF399764, AX684850, AB044575, AF114923, AF114915, AF114903, M81158, AJ229060, X12576, X00731, X01963

(4) was comprised in;

GenBank Accession No. J04423.1, J04423.1, J04423.1, J04423.1, J04423.1, J04423.1, J04423.1, X03453.1, X03453.1, L38424.1, L38424.1, L38424.1, X17013.1, X17013.1, X17013.1, M24537.1, M24537.1, M24537.1, X04603.1, X04603.1, X04603.1, K01391.1, K01391.1, K01391.1, J04423.1, J04423.1, J04423.1, J04423.1, J04423.1, J04423.1, J04423.1, X03453.1, X03453.1, L38424.1, L38424.1, L38424.1, X17013.1, X17013.1, X17013.1, M24537.1, M24537.1, M24537.1, X04603.1, X04603.1, X04603.1, V01288.1, V01288.1, V01288.1, X16860.1, X16860.1, X16860.1, L12026.1, L12026.1, L12026.1, Z75578.1, Z75578.1, Z75578.1, Z75578.1, Z75578.1, J01355.1, J01355.1, J01355.1, J01355.1 and J01355.1

Example 18

Identification of Molecular Markers that were Highly Inducible in Zinc Depleted Condition 1. Preparation of mRNA Strain 34/70 was grown overnight in LZMM medium+40 μM zinc sulfate at 30° C. with shaking. LZMM medium contains 0.17% yeast nitrogen base w/o amino acids (manufactured by DIFCO), 0.5% ammonium sulfate, 20 mM sodium citrate (pH 4.2), 125 μM MnCl2, 10 μM FeCl2, 2% maltose, 10 mM EDTA (pH 8.0). Cells were harvested and washed three times with sterile distilled water before inoculation to an optical density (OD600) of 0.25 in 500 ml of 1) zinc depleted medium (LZMM medium), 2) zinc replete medium (LZMM+40 μM zinc sulfate), 3) oxidative stress medium (LZMM+40 μM zinc sulfate+2 mM H2O2), 4) carbon starvation medium (deleting maltose from above LZMM+40 μM zinc sulfate). Cells were grown at 30° C. for 6 hours and harvested for RNA preparation.

Preparation of total RNA was carried out using RNeasy® Mini Kit (manufactured by QIAGEN) according to the attached manual. Preparation of Poly(A)+mRNA from total RNA was carried out using Oligotex Direct mRNA kit (manufactured by QIAGEN) according to the attached manual.

2. Synthesis of Biotin-Labeled cRNA

Synthesis of Biotin-Labeled cRNA was carried out using BioArray HighYield RNA Transcript Labeling Kit (manufactured by Affymetrix) according to the attached manual.

3. Hybridization

5 μg of Biotin-Labeled cRNA, 1.7 μl of 3 nM Control Oligonucleotide B2 (manufactured by Affymetrix), 5 μl of 20× Eukaryotic Hybridization Controls (manufactured by Affymetrix), 1 μl of 10 mg/ml Herring Sperm DNA (manufactured by Affymetrix), 1 μl of 50 mg/ml Acetylated BSA (manufactured by Affymetrix), 50 μl of 2× Hybridization buffer (manufactured by Affymetrix), and water (manufactured by Affymetrix) to give final volume of 100 μl were mixed and hybridized to the DNA microarray according to a Technical Mannual of Affymetrix. After 16 hours of hybridization, hybridization cocktail was removed and the DNA microarray was washed using the GeneChip® Fludics Station (manufactured by Affymetrix), and stained with 600 μl of Streptavidin Phycoerythrin (300 μl of 2× MES Stain Buffer (manufactured by Affymetrix), 24 μl of 50 mg/ml acetylated BSA (manufactured by Affymetrix), 6 μl of 1 mg/ml StreptAvidin-Phycoerythrin (manufactured by Affymetrix), 270 μl of water (manufactured by Affymetrix)) according to a Technical Mannual of Affymetrix.

4. Data Analysis

Detection of the signal intensity of the microarray was carried out using Gene Chip Analysis Basic System and analysis software (GCOS; GeneChip Operating Software 1.0) according to a Technical Mannual of Affymetrix. Normalization was carried out using the All Probe Sets in GCOS to adjust a signal in comparison analysis. The comparison files of gene expression which were compared (1) zinc depleted condition to zinc replete condition, (2) oxidative stress condition to zinc replete condition and (3) carbon starvation condition to zinc replete condition were created using GCOS, respectively. The genes whose expressions were increased by more than 0.3 at signal log ratio only in above comparison (1) were shown in Table 4.

Sc-1159-1_at, Sc-1161-1_at, Sc-5030-1_at, Sc-2123-1_at correspond to Sc YGL258W, Sc YGL256W, Sc YOL154W, Sc YKL175W, respectively. And it is known that these genes are transcriptionally induced in zinc depleted condition (Higgins, V. J. et al., Appl. Environ. Microbiol., 69: 7535-7540(2003)). Lg-4216-1—s—at was designed to correspond to Non-Sc YKL175W whose function was assigned zinc ion transporter activity. It is known that zinc ion transporter is transcriptionally induced in zinc depleted condition.

In conclusion, it is shown that the molecular markers that are highly induced in zinc depleted condition can be identified using the bottom fermenting yeast DNA microarray.

Example 19

Gene Expression Analysis of Brewing Yeast Under Beer Fermenting Condition

Fermentation test using strain 34/70 was carried out under the following condition.
Original extract: 12.84%
Fermentation scale: 2 liters
Dissolved oxygen concentration: about 9 ppm
Fermentation temperature: 15° C.
Pitching rate: 10 g of wet yeast cells/2 L of wort

TABLE 4

| | (1) zinc deplete/zinc replete | | | (2) oxidative stress/zinc replete | | | (3) carbon starvation/zinc replete | | | Annotation | |
|---|---|---|---|---|---|---|---|---|---|---|---|
| Probe set | Signal Log Ratio | Detection | Change | Signal Log Ratio | Detection | Change | Signal Log Ratio | Detection | Change | Gene Name | Type |
| Sc-1159-1 at | 3.1 | P | 1 | −0.6 | A | NC | −0.5 | A | NC | YGL258W | Sc |
| Lg-4570-1 at | 1.2 | P | 1 | 0.1 | P | NC | −0.7 | A | D | YNL254C | Non-Sc |
| Sc-1161-1 at | 1.1 | P | 1 | −1.1 | P | D | −1.2 | P | D | YGL256W | Sc |
| Lg-3847-1 at | 0.9 | P | 1 | −0.6 | P | D | −1.1 | P | D | YGL256W | Non-Sc |
| Sc-2889-1 at | 0.7 | P | 1 | −0.5 | P | D | −1.8 | P | D | YNL254C | Sc |
| Lg-4216-1 s at | 0.6 | P | 1 | −0.6 | P | D | −0.4 | P | D | YKL175W | Non-Sc |
| Sc-5030-1 at | 0.5 | P | 1 | −3.6 | P | D | −3.8 | P | D | YOL154W | Sc |
| Sc-1160-1 at | 0.4 | P | 1 | −1.1 | P | D | −0.9 | P | D | YOL257C | Non-Sc |
| Lg-1751-1 at | 0.4 | P | 1 | −1 | P | D | −0.7 | P | D | YLR209C | Sc |
| Sc-3567-1 at | 0.4 | P | 1 | 0.2 | P | NC | −0.4 | P | NC | YPL148C | Non-Sc |
| Lg-3161-1 at | 0.4 | P | 1 | −0.8 | P | D | −0.9 | P | D | YMR020W | Sc |
| Sc-3984-1 x at | 0.4 | P | 1 | 0.2 | P | NC | −1.3 | P | D | YDL130W | Non-Sc |
| Lg-4390-2 x at | 0.4 | P | 1 | 0.3 | P | NC | −0.5 | P | NC | YLR339C | Sc |
| Sc-4798-1 at | 0.4 | P | 1 | 0.2 | P | NC | −2.3 | P | D | YLR435W | Non-Sc |
| Lg-5145-1 s at | 0.4 | P | 1 | 0.2 | P | NC | −2.3 | P | D | YDR312W | Sc |
| Lg-139-1 at | 0.3 | P | 1 | −0.3 | P | NC | −4.1 | A | D | YBR104W | Non-Sc |
| Lg-467-1 at | 0.3 | P | 1 | 0.1 | P | NC | −2 | P | D | YDR161W | Non-Sc |
| Sc-1412-1 at | 0.3 | P | 1 | 0 | P | NC | −2 | P | D | YGR081C | Non-Sc |
| SLg-961-1 at | 0.3 | P | 1 | 0.2 | P | NC | −1.5 | P | D | YGR103W | Sc |
| Sc-2122-1 at | 0.3 | P | 1 | −0.3 | P | NC | 0.1 | P | NC | YKL176C | Non-Sc |
| Sc-2123-1 at | 0.3 | P | 1 | −0.5 | P | D | −1.1 | P | D | YKL175W | Sc |
| Sc-2209-1 at | 0.3 | P | 1 | 0.2 | P | NC | −1.7 | P | D | YKL072W | Sc |
| Sc-2356-1 at | 0.3 | P | 1 | −0.1 | P | NC | −2.4 | P | D | YLR129W | Sc |
| Lg-1955-1 at | 0.3 | P | 1 | −0.1 | P | NC | 0 | P | NC | YMR096W | Sc |
| Sc-2890-1 at | 0.3 | P | 1 | −0.3 | P | NC | −1.2 | P | D | YNL253W | Non-Sc |
| Lg-2100-1 at | 0.3 | P | 1 | −0.8 | P | D | −1.7 | P | D | YNL217W | Non-Sc |
| Lg-2258-1 at | 0.3 | P | 1 | 0.1 | P | NC | −1.8 | P | D | YOL125W | Non-Sc |
| Sc-3203-1 at | 0.3 | P | 1 | 0.1 | P | NC | −0.8 | P | D | YOL022C | Sc |
| Sc-3651-1 s at | 0.3 | P | 1 | 0.1 | P | NC | −0.1 | P | NC | YPR044C | Sc |
| Lg-2648-1 at | 0.3 | P | 1 | 0.1 | P | NC | −2.1 | P | D | YPR048W | Non-Sc |
| Lg-3014-1 at | 0.3 | P | 1 | −0.7 | P | D | −0.3 | P | NC | YJL055W | Non-Sc |
| Sc-4034-1 at | 0.3 | P | 1 | 0.1 | P | NC | 0.3 | P | NC | YDR017C | Sc |
| Lg-3670-1 at | 0.3 | P | 1 | 0.4 | P | NC | −2.1 | P | D | YDR087C | Non-Sc |
| Sc-4163-1 at | 0.3 | P | 1 | 0.1 | P | NC | −2.5 | M | D | YDR449C | Sc |
| Sc-4365-1 at | 0.3 | P | 1 | 0.3 | P | NC | −1.4 | P | D | YGR145W | Sc |
| Sc-4454-1 at | 0.3 | P | 1 | 0.4 | P | NC | −1.8 | P | D | YHR197W | Sc |
| Lg-4608-2 at | 0.3 | P | 1 | −0.3 | P | D | −1.9 | P | D | YNl112W | Non-Sc |
| Lg-4622-1 at | 0.3 | P | 1 | 0.1 | P | NC | −2.5 | P | D | YNL062C | Non-Sc |
| Sc-5321-1 at | 0.3 | P | 1 | 0.4 | P | NC | −1.1 | P | D | YGR272C | Sc |
| Lg-5125-1 at | 0.3 | P | 1 | 0.2 | P | NC | −2.4 | P | D | YOR101C | Non-Sc |

Signal Log Ratio (2″) indicates the magnitude and direction of a transcript when two arrays are compared. Detection indicates whether a transcript is reliably detected (P; Present) or not detected (A; Absent) based on the Detection p-value calculated by Detection Algorithm with default paramater in GCOS. Change indicates whether a transcript is reliably increased (I; Increase) or decreased (D; Decrease) or not changed (NC; No Change) based on the Change p-value calculated by Change Algorithm with default paramater in GCOS. Gene name indicates where the corresponding probe set was designed. Type indicates whether a gene is Sc ORF (Sc) or Non-Sc ORF (Non-Sc).

Wort was periodically sampled and monitored in cell growth (OD600) (FIG. 12-($a$)) and apparent extract (FIG. 12-($b$)). mRNA was extracted from the cells withdrawn from the fermentation tubes 42 hours after inoculation, biotin labeled and hybridized to the bottom fermenting yeast DNA microarray as described in example 18. Detection of the signal intensity was carried out using a Gene Chip Analysis Basic System and analysis soft ware (GCOS; GeneChip Operating Software 1.0) manufactured by Affymetrix.

There were more than a few genes whose Sc type probe sets and non-Sc type probe sets showed quite different signal intensities. Examples of SSU1 genes and MET14 genes, which are related to sulfite production during beer fermentation are shown in Table 5. In the case of SSU1 genes and MET14 genes of strain 34/70, the expressions of non-Sc type were higher than those of Sc type, by 3.4-fold and 7-fold, respectively.

In order to confirm this difference is due to neither the difference of hybridization efficiency of each probe set nor cross hybridization between Sc and non-Sc type probe sets, comparative genomic hybridization with the bottom fermenting yeast DNA microarray was carried out using strain 34/70, a laboratory strain (*S. cerevisiae*) S288C and *S. carlsbergensis* strain IF011023. The preparation of genomic DNA, hybridization to DNA microarray and detection of the signal intensities were carried out with the method described before. As shown in Table 6, the ratio of signal intensity of non-Sc type to that of Sc type was 1.0 for SSU1 genes and 1.3 for MET14 genes in strain 34/70. This result shows that hybridization efficiencies of Sc and non-Sc probe sets were almost the same.

Furthermore, strain S288C, which doesn't have non-Sc type genes, showed very low signal intensities to non-Sc type probe sets, and strain IF011023, which doesn't have Sc type SSU1 gene and Sc type MET14, showed very low signal intensities to Sc type SSU1 and Sc type MET14 probe sets. These results clearly show that cross hybridization did not occur between Sc and non-Sc type probe sets.

From these results, in strain 34/70, the expressions of non-Sc SSU1 and non-Sc MET14 were significantly higher than those of Sc SSU1 and Sc MET14, respectively. These genes are thought to be candidates which contribute to the high sulfite production ability of bottom fermenting yeasts.

In conclusion, it was demonstrated that gene expression analysis of brewing yeast strains using the bottom fermenting yeast DNA microarray was useful for the selection of gene(s) for functional analysis.

Example 20

Classification of Brewing Strains by Comparative Genomic Hybridization with the Bottom Fermenting Yeast DNA Microarray Preparation of yeast genomic DNA and hybridization to the DNA microarray was carried out as described in (Example 8). Detection of the signal intensity of microarray was carried out using a Gene Chip Analysis Basic System and analysis soft ware (GCOS; GeneChip Operating Software 1.0) manufactured by Affymetrix. The percentage of probes, to which the DNA of brewing yeast hybridized was calculated and the identity between strain 34/70 and the tested strain was estimated as shown in Table 7. Strains BH225, BH232 and BH235 hybridized to more than 99% of both Sc type and non-Sc type probes of the the bottom fermenting yeast DNA microarray. It suggests that these strains are very similar to strain 34/70, and that this microarray is useful for the gene expression analysis of these strains. On the other hand, strain BH212 showed relatively low (97.8 and 97.7% for Sc type and non-Sc type probe, respectively) percentage of hybridization, which means this strain is a little bit different from strain 34/70. From these results, relationship among lager brewing strains can be estimated and classification of lager brewing strains can be carried out.

From the result of the analysis of strain BH212, some loci which showed very low signal intensities were found. They may be lost in strain BH212 or their sequences may be different from those of strain 34/70. In contrast, some loci which showed high signal intensities were also found. These may be high in copy number in strain BH212. Such loci can be selected for functional analysis because they may contribute to the difference of fermentation characteristics between strain BH212 and strain 34/70.

TABLE 5

| | gene | | | |
|---|---|---|---|---|
| | Sc SSU1 | non Sc SSU1 | Sc MET14 | non Sc MET14 |
| | | probe set | | |
| | Sc-3594-1 at | Lg-3333-1 at | Sc-2246-1 at | Lg-1564-1 at |
| signal intensity | 145.2 | 490.4 | 177.3 | 1245.8 |

TABLE 7

| | percentage of hybridized probes | | | | |
|---|---|---|---|---|---|
| | strain No. | | | | |
| | 34/70 | BH225 | BH232 | BH235 | BH212 |
| Sc type | 99.6 | 99.8 | 99.8 | 99.8 | 97.8 |
| non-Sc type | 99.5 | 99.9 | 99.9 | 99.6 | 97.7 |

TABLE 6

| | | gene | | | |
|---|---|---|---|---|---|
| | | Sc SSU1 | non Sc SSU1 | Sc MET14 | non Sc MET14 |
| | | | probe set | | |
| strains | | Sc-3594-1 at | Lg-3333-1 at | Sc-2246-1 at | Lg-1564-1 at |
| 34/70 | signal intensity | 360.9 | 356.8 | 244.2 | 324.8 |
| S288C | | 516.2 | 6.5 | 405.3 | 13.4 |
| S carlsbergensis LEOL1023 | | 8.5 | 746.9 | 6.8 | 508.4 |

Example 21

Detection of Nucleotide Polymorphism

Furthermore, (single) nucleotide polymorphism was detectable by the analysis of comparative genomic hybridization. The sets of oligonucleotides for each probe consist of Perfect Match oligonucleotide (PM) which is identical to the sequence of strain 34/70 and MisMatch oligonucleotide (MM) which contains a single base mismatch in the central position of the oligonucleotide. Genomic DNA of a laboratory strain S288C was hybridized to the bottom fermenting yeast DNA microarray. As shown in Table 8, probes which showed higher (more than 5-fold) signal in MM than in PM had single nucleotide polymorphism.

TABLE 8

| probe | signal of PM probe | signal of MM probe | | |
|---|---|---|---|---|
| Mt-6s at 653 337 | 112.38 | 634.39 | DNA sequence of PM | GAATCAATTAACTTATGGTTTCTTA |
| | | | | \|\|\|\|\|\|\|\|\|\|\|\|\| \|\|\|\|\|\|\|\|\|\|\|\| |
| | | | DNA sequence of tested strain | GAATCAATTAACATATGGTTTCTTA |
| | | | | \|\|\|\|\|\|\|\|\|\|\|\|\|\|\|\|\|\|\|\|\|\|\|\|\| |
| | | | DNA sequence of MM | GAATCAATTAACATATGGTTTCTTA |

A database compiling the data of the whole genome sequences of an industrial yeast or, particularly, of a brewing yeast used for the production of alcoholic beverages such as beer is prepared. Using such a database, genes of brewing yeast are selected, and functions of the genes are analyzed by disruption or overexpression in yeast cells, and find genes participating in the desired brewing character. Furthermore, it is possible to breed yeast strains by controlling the expression of the said genes, and produce an alcohol or an alcoholic beverage where productivity and quality are improved, such as alcoholic beverages with high concentration of sulfite which shows antioxidant activity in the product, excellent flavor stability and a longer quality preservation period.

Based on the database compiling the data of the whole genome sequences of an industrial yeast or, particularly, of a brewing yeast, a DNA array is produced. Using the DNA array, it is possible to analyze functions of the genes, classify industrial yeasts and detect nucleotide polymorphism and soon.

---

What is claimed is:

1. An isolated polypeptide comprising:
    (a) a polypeptide comprising the amino acid sequence of SEQ ID NO: 3; or,
    (b) a polypeptide having an amino acid sequence, wherein in one to 20 amino acid residues are deleted, substituted, added, or a combination thereof, in the amino acid sequence of SEQ ID NO: 3.

2. The isolated polypeptide of claim 1, wherein the polypeptide consists of SEQ ID NO: 3.

3. The isolated polypeptide of claim 1, comprising a polypeptide having an amino acid sequence, wherein one to 10 amino acid residues are deleted, substituted, added, or a combination thereof, in the amino acid sequence of SEQ ID NO: 3.

4. The isolated polypeptide of claim 1, comprising a polypeptide having an amino acid sequence, wherein one to 5 amino acid residues are deleted, substituted, added, or a combination thereof, in the amino acid sequence of SEQ ID NO: 3.

5. The isolated polypeptide of claim 1, comprising a polypeptide having 80% or more of identity to the amino acid sequence of SEQ ID NO: 3.

6. The isolated polypeptide of claim 1, comprising a polypeptide having 95% or more of identity to the amino acid sequence of SEQ ID NO: 3.

* * * * *